(12) United States Patent
Pierce et al.

(10) Patent No.: US 12,331,328 B2
(45) Date of Patent: Jun. 17, 2025

(54) CRISPR/CAS9-MEDIATED EXON-SKIPPING APPROACH FOR USH2A-ASSOCIATED USHER SYNDROME

(71) Applicants: Massachusetts Eye and Ear Infirmary, Boston, MA (US); Editas Medicine, Inc., Cambridge, MA (US)

(72) Inventors: Eric A. Pierce, Boston, MA (US); Carrie Marie Margulies, Newton, MA (US); Nachiket D. Pendse, Quincy, MA (US); Sebastian W. Gloskowski, Malden, MA (US); Qin Liu, Boston, MA (US); Morgan L. Maeder, Cambridge, MA (US)

(73) Assignees: Massachusetts Eye and Ear Infirmary, Boston, MA (US); Editas Medicine, Inc., Cambridge, MA (US)

( * ) Notice: Subject to any disclaimer, the term of this patent is extended or adjusted under 35 U.S.C. 154(b) by 1272 days.

(21) Appl. No.: 17/040,629

(22) PCT Filed: Mar. 25, 2019

(86) PCT No.: PCT/US2019/023934
§ 371 (c)(1),
(2) Date: Sep. 23, 2020

(87) PCT Pub. No.: WO2019/183641
PCT Pub. Date: Sep. 26, 2019

(65) Prior Publication Data
US 2021/0115419 A1     Apr. 22, 2021

Related U.S. Application Data

(60) Provisional application No. 62/794,402, filed on Jan. 18, 2019, provisional application No. 62/647,578, filed on Mar. 23, 2018.

(51) Int. Cl.
*C12N 9/22* (2006.01)
*A61K 48/00* (2006.01)
(Continued)

(52) U.S. Cl.
CPC ............ *C12N 9/22* (2013.01); *A61K 48/0016* (2013.01); *C12N 15/113* (2013.01); *C12N 15/86* (2013.01);
(Continued)

(58) Field of Classification Search
CPC ........ C12N 9/22; C12N 15/113; C12N 15/86; C12N 2310/20; C12N 2320/33;
(Continued)

(56) References Cited

U.S. PATENT DOCUMENTS

2014/0256802 A1   9/2014  Boye et al.
2016/0340661 A1   11/2016 Cong et al.
(Continued)

FOREIGN PATENT DOCUMENTS

CA       2986021         11/2016
WO    WO-2016005514 A1 *  1/2016  ........... C12N 15/113
(Continued)

OTHER PUBLICATIONS

Ferrari et al. 2011. Retinitis Pigmentosa: Genes and Disease Mechanisms. Curr. Genom. 12:238-249 (Year: 2011).*
(Continued)

*Primary Examiner* — Nancy J Leith
*Assistant Examiner* — Ruth Sophia Arieti
(74) *Attorney, Agent, or Firm* — Fish & Richardson P.C.

(57) ABSTRACT

Compositions for use in treating subjects with USH2A-associated retinal and/or cochlear degeneration that result from mutations in exon 13 of the USH2A gene by deletion of exon 13 from the USH2A gene or transcripts, and
(Continued)

methods of use thereof, as well as genetically modified animals and cells.

17 Claims, 28 Drawing Sheets
(5 of 28 Drawing Sheet(s) Filed in Color)
Specification includes a Sequence Listing.

(51) Int. Cl.
　　　*C12N 15/113*　　　(2010.01)
　　　*C12N 15/86*　　　(2006.01)
(52) U.S. Cl.
　　　CPC ...... *C12N 2310/20* (2017.05); *C12N 2320/33* (2013.01); *C12N 2750/14143* (2013.01)
(58) Field of Classification Search
　　　CPC ...... C12N 2750/14143; C12N 15/1138; A61K 48/0016; A61K 9/0019; A01K 2207/15; A01K 2217/072; A01K 2227/105; A01K 2267/0306; A01K 67/0275; C12Y 301/01
　　　See application file for complete search history.

(56) References Cited

U.S. PATENT DOCUMENTS

| | | |
|---|---|---|
| 2017/0073674 A1 | 3/2017 | Maeder et al. |
| 2017/0159052 A1 | 6/2017 | Van Wyk |

FOREIGN PATENT DOCUMENTS

| | | | |
|---|---|---|---|
| WO | WO 2016/089866 | 6/2016 | |
| WO | WO-2016161380 A1 * | 10/2016 | ........... C12N 15/102 |
| WO | WO 2017/095967 | 6/2017 | |
| WO | WO 2018/026976 | 2/2018 | |

OTHER PUBLICATIONS

Lyon (and Wang. 2012. Identifying disease mutations in genomic medicine settings: current challenges and how to accelerate progress. Genome Med. 4:58 (Year: 2012).*
Crane et al. 2021. Gene Therapy to the Retina and the Cochlea. Frontier Neurosci. 15: 652215 (Year: 2021).*
ClinVar. 2024. 1[CHR] and 1:216247153[chrpos37] and 216246494:2000000000[chrpos37]. NCBI. Available online at ncbi.nlm.nih.gov. Accessed Mar. 21, 2024 (Year: 2024).*
Johns Hopkins. 2024. Scoliosis. Available online at Hopkinsmedicine.org. Accessed on Mar. 22, 2024 (Year: 2024).*
Cuzzuol et al. 2024. Usher syndrome: Genetic diagnosis and current therapeutic approaches. World J. Otorhinolaryngol. 11[1]:1-1 (Year: 2024).*
Aartsma-Rus et al., "Theoretic applicability of antisense-mediated exon skipping for Duchenne muscular dystrophy," Hum Mutat., 2009, 30(3):293-299.
Aller et al., "Identification of 14 novel mutations in the long isoform of USH2A in Spanish patients with Usher syndrome type II," J Med Genet., 2006, 43:e55, 6 pages.
Aller et al., "The USH2A c.2299delG mutation: dating its common origin in a Southern European population," Eur J Hum Genet, 2010, 18(7):788-93.
Auslender et al., "Four USH2A founder mutations underlie the majority of Usher syndrome type 2 cases among non-Ashkenazi Jews," Genet Test., 2008, 12(2):289-94.
Bainbridge et al., "Effect of gene therapy on visual function in Leber's congenital amaurosis," N.Engl.J.Med., 2008, 358(21):2231-2239.
Baux et al., "Enrichment of LOVD-USHbases with 152 USH2A Genotypes Defines an Extensive Mutational Spectrum and Highlights Missense Hotspots," Hum. Mutat., 2014, 35(10):1179-1186.
Bennett et al., "AAV2 gene therapy readministration in three adults with congenital blindness," Sci Transl Med., 2012, 4(120):120ra15, 11 pages.
Béroud et al., "Multiexon skipping leading to an artificial DMD protein lacking amino acids from exons 45 through 55 could rescue up to 63% of patients with Duchenne muscular dystrophy," Hum Mutat., 2007, 28(2):196-202.
Besnard et al., "Experience of targeted Usher exome sequencing as a clinical test," Molecular Genetics & Genomic Medicine, 2014, 2(1):30-43.
Bonnet et al., "An innovative strategy for the molecular diagnosis of Usher syndrome identifies causal biallelic mutations in 93% of European patients," European Journal of Human Genetics, 2016, 9 pages.
Boo et al., "A Novel Frameshift Mutation of the USH2A Gene in a Korean Patient with Usher Syndrome Type II," Clinical and Experimental Otorhinolaryngology, 2013, 6(1):41-44, 4 pages.
Bowles et al., "Phase 1 gene therapy for Duchenne muscular dystrophy using a translational optimized AAV vector," Molecular Therapy, 2012, 20(2):443-55.
Cheng et al., "Multiplexed activation of endogenous genes by CRISPR-on, an RNA-guided transcriptional activator system," Cell Res, 2013, 23(10):1163-71.
Cideciyan et al., "Human gene therapy for RPE65 isomerase deficiency activates the retinoid cycle of vision but with slow rod kinetics," Proc. Nat. Acad. Sci., 2008, 105(39):15112-7.
Consugar et al., "Panel-based genetic diagnostic testing for inherited eye diseases is highly accurate and reproducible, and more sensitive for variant detection, than exome sequencing," Genet Med., 2015, 17(4):253-261.
Davis et al., "TTC21B contributes both causal and modifying alleles across the ciliopathy spectrum," Nat Genet, 2011, 43(3):189-96.
Dreyer et al., "Identification of novel USH2A mutations: implications for the structure of USH2A protein," European Journal of Human Genetics, Aug. 2000:500-506, 7 pages.
Dreyer et al., "A common ancestral origin of the frequent and widespread 2299delG USH2A mutation," Am. J. Hum. Genet., 2001, 69:228-234.
Dreyer et al., "Spectrum of USH2A mutations in Scandinavian patients with Usher syndrome type II," Hum. Mutat., Mar. 2008, 29(3):451, 15 pages.
Extended European Search Report in European Appln. No. 19772564.1, dated Nov. 30, 2021, 9 pages.
Fuster-García et al., "USH2A Gene Editing Using the CRISPR System," Mol Ther Nucleic Acids, Aug. 2017:529-541.
Grati et al., "Localization of PDZD7 to the stereocilia ankle-link associates this scaffolding protein with the Usher syndrome protein network," J Neurosci, 2012, 32(41):14288-93.
Hartong et al., "Retinitis pigmentosa," Lancet, 2006, 368(9549):1795-809.
Horvath et al., "Diversity, Activity, and Evolution of CRISPR Loci in *Streptococcus thermophilus*," J Bacteriol., 2008, 190:1401-1412.
International Preliminary Report on Patentability in International Appln. No. PCT/US2019/023934, dated Oct. 8, 2020, 14 pages.
International Search Report and Written Opinion in International Appln. No. PCT/US2019/023934, dated Aug. 28, 2019, 11 pages.
Inui et al., "Rapid generation of mouse models with defined point mutations by the CRISPR/Cas9 system," Sci Rep, Apr. 2014:5396, 8 pages.
Jacobson et al., "Gene therapy for leber congenital amaurosis caused by RPE65 mutations: safety and efficacy in 15 children and adults followed up to 3 years," Arch Ophthalmol., 2012, 130(1):9-24.
Jaijo et al., "Microarray-based mutation analysis of 183 Spanish families with Usher syndrome," Invest Ophthalmol Vis Sci., Mar. 2010, 51(3):1311-1317.
Jelcick et al., "Genetic variations strongly influence phenotypic outcome in the mouse retina," PLoS One, 2011, 6(7):e21858, 13 pages.
Kalinec et al., "Establishment and characterization of conditionally immortalized organ of corti cell lines," Cell Biol Int, 1999, 23(3):175-84.

(56) References Cited

OTHER PUBLICATIONS

Kelley et al., "The developing organ of Corti contains retinoic acid and forms supernumerary hair cells in response to exogenous retinoic acid in culture," Development, 1993, 119(4):1041-1053.
Kemaladewi et al., "Exon Snipping in Duchenne Muscular Dystrophy," Trends Mol Med, 2016, 22(3):187-9.
Kim et al., "Digenome-seq: genome-wide profiling of CRISPR-Cas9 off-target effects in human cells," Nat. Methods, Feb. 12, 2015:237-243, 8 pages.
Le Quesne Stabej et al., "Comprehensive sequence analysis of nine Usher syndrome genes in the UK National Collaborative Usher Study," J Med Genet., 2012, 49:27-36.
Lenassi et al., "A detailed clinical and molecular survey of subjects with nonsyndromic USH2A retinopathy reveals an allelic hierarchy of disease-causing variants," Eur J Hum Genet, 2015, 23(10):1318-27.
Lentz et al., "Usher Syndrome Type II," GeneReviews®, R.A. Pagon et al., Editors. 1993, University of Washington, Seattle: Seattle WA.
Lentz, "Advances in Drug Therapy for Usher Syndrome," Presented at Usher Syndrome 7th Annual Family Conference, Usher Syndrome Coalition, New Orleans, LA, Jul. 11, 2015, 27 pages.
Leroy et al., "Spectrum of mutations in USH2A in British patients with Usher syndrome type II," Exp Eye Res., 2001, 72(5):503-9.
Liu et al., "The retinitis pigmentosa 1 protein is a photoreceptor microtubule-associated protein," J Neurosci, 2004, 24(29):6427-36.
Liu et al., "The severity of retinal degeneration in Rp1h gene-targeted mice is dependent on genetic background," Invest Ophthalmol Vis Sci, 2009, 50(4):1566-74.
Liu et al., "Usherin is required for maintenance of retinal photoreceptors and normal development of cochlear hair cells," Proc Natl Acad Sci USA, 2007, 104(11):4413-8.
Long et al., "Postnatal genome editing partially restores dystrophin expression in a mouse model of muscular dystrophy," Science, 2016, 351(6271):400-3.
Lu et al., "Cell transplantation to arrest early changes in an ush2a animal model," Invest Ophthalmol Vis Sci, 2010, 51(4):2269-76.
Maclachlan et al., "Preclinical safety evaluation of AAV2-sFLT01—a gene therapy for age-related macular degeneration," Molecular Therapy, 2011, 19(2):326-34.
Maerker et al., "A novel Usher protein network at the periciliary reloading point between molecular transport machineries in vertebrate photoreceptor cells," Hum Mol Genet., 2008, 17(1):71-86.
Maguire et al., "Age-dependent effects of RPE65 gene therapy for Leber's congenital amaurosis: a phase 1 dose-escalation trial," Lancet, 2009, 374(9701):1597-605.
Maguire et al., "Safety and efficacy of gene transfer for Leber's congenital amaurosis," N Engl J Med., 2008, 358(21):2240-8.
Mashiko et al., "Feasibility for a large scale mouse mutagenesis by injecting CRISPR/Cas plasmid into zygotes," Dev Growth Differ, Jan. 2014, 56(1):122-9.
Matsuda et al., "Controlled expression of transgenes introduced by in vivo electroporation," Proc Natl Acad Sci USA, Jan. 2007, 104(3):1027-32.
Millan et al., "An update on the genetics of usher syndrome," J Ophthalmol, 2011, 2011:417217, 8 pages.
Nathwani et al., "Adenovirus-associated virus vector-mediated gene transfer in hemophilia B," N Engl J Med., 2011, 365(25):2357-65, 9 pages.
Nelson et al., "In vivo genome editing improves muscle function in a mouse model of Duchenne muscular dystrophy," Science, 2016, 351(6271):403-7.
Ousterout et al., "Multiplex CRISPR/Cas9-based genome editing for correction of dystrophin mutations that cause Duchenne muscular dystrophy," Nat Commun., Jun. 2015:6244, 13 pages.
Pendse et al., "Abstract #: 895: Evaluation of therapeutic potential of human USH2A gene lacking exon 13 (USH2A-ΔEx13) for restoring ciliogenesis," Abstract, Presented at 21st Annual Meeting of the American Society of Gene and Cell Therapy, Chicago, IL, May 16-19, 2018; Molecular Therapy, 2018, 26(5S1):409, 1 page.
Pendse et al., "CRISPR-Cas based evaluation of the therapeutic potential for USH2A associated diseases," Abstract, Presented at American Society of Gene & Cell Therapy 22nd Annual Meeting, Washington, D.C., Apr. 29-May 2, 2019; 1 page.
Pendse et al., "In Vivo Assessment of Potential Therapeutic Approaches for USH2A-Associated Diseases," Adv Exp Med Biol., 2019, 1185:91-96.
Pennings et al., "Evaluation of visual impairment in Usher syndrome 1b and Usher syndrome 2a," Acta Ophthalmol Scand., Apr. 2004, 82(2): 18 pages.
Platt et al., "CRISPR-Cas9 knockin mice for genome editing and cancer modeling," Cell, Oct. 2014, 159(2):440-55.
Ran et al., "In vivo genome editing using *Staphylococcus aureus* Cas9," Nature, 2015, 520(7546):186-91, 18 pages.
Reiners et al., "Scaffold protein harmonin (USH1C) provides molecular links between Usher syndrome type 1 and type 2," Hum Mol Genet., 2005, 14(24):3933-43.
Rong et al., "Novel and Recurrent MYO7A Mutations in Usher Syndrome Type 1 and Type 2," PLoS One, May 2014, 9(5):e97808, 9 pages.
Saihan et al., "Update on Usher syndrome," Curr Opin Neurol, 2009, 22(1):19-27.
Sandberg et al., "Disease course in patients with autosomal recessive retinitis pigmentosa due to the USH2A gene," Invest Ophthalmol Vis Sci, 2008, 49(12):5532-9.
Senis et al., "CRISPR/Cas9-mediated genome engineering: an adeno-associated viral (AAV) vector toolbox," Biotechnol J, Nov. 2014, 9(11):1402-12.
Seyedahmadi et al., "Comprehensive screening of the USH2A gene in Usher syndrome type II and non-syndromic recessive retinitis pigmentosa," Experimental Eye Research, Aug. 2004, 79(2):167-173.
Slijkerman et al., "Antisense Oligonucleotide-based Splice Correction for USH2A-associated Retinal Degeneration Caused by a Frequent Deep-intronic Mutation," Mol Ther Nucleic Acids, 2016, 5(10):e381, 10 pages.
Sorusch et al., "Characterization of the ternary Usher syndrome SANS/ush2a/whirlin protein complex," Human Molecular Genetics, Jan. 2017, 26(6):1157-1172.
Suzuki et al., "In vivo genome editing via CRISPR/Cas9 mediated homology-independent targeted integration," Nature, 2016, 540(7631):144-149, 24 pages.
Swiech et al., "In vivo interrogation of gene function in the mammalian brain using CRISPR-Cas9," Nat Biotechnol, 2015, 33(1):102-6, 9 pages.
Tabebordbar et al., "In vivo gene editing in dystrophic mouse muscle and muscle stem cells," Science, 2016, 351(6271):407-11.
Tsai et al., "GUIDE-seq enables genome-wide profiling of off-target cleavage by CRISPR-Cas nucleases," Nat Biotechnol, 2015, 33(2):187-97, 12 pages.
Tsai et al., "Open-source guideseq software for analysis of GUIDE-seq data," Nat Biotechnol, 2016, 34(5):483.
Van Wijk et al., "Abstract: Antisense Oligonucleotide-induced Skipping of USH2A exon13 Restores Visual Function in Zebrafish," Invest. Ophthalmol. Vis. Sci., Jun. 2017, 58:2490, 2 pages.
Van Wijk et al., "Identification of 51 novel exons of the Usher syndrome type 2A (USH2A) gene that encode multiple conserved functional domains and that are mutated in patients with Usher syndrome type II," Am J Hum Genet, 2004, 74(4):738-44.
Vijayakumar et al., "Rescue of peripheral vestibular function in Usher syndrome mice using a splice-switching antisense oligonucleotide," Hum Mol Genet., 2017, 26(18):3482-3494.
Vona et al., "Targeted next-generation sequencing of deafness genes in hearing-impaired individuals uncovers informative mutations," Genet Med., Dec. 2014, 16(12):945-953.
Wang et al., "One-step generation of mice carrying mutations in multiple genes by CRISPR/Cas-mediated genome engineering," Cell, 2013, 153(4):910-8.
Weston et al., "Genomic Structure and Identification of Novel Mutations in Usherin, the Gene Responsible for Usher Syndrome Type IIa," Am. J. Hum. Genet., 2000, 66(4):1199-1210.

(56) References Cited

OTHER PUBLICATIONS

Xu et al., "Seven novel mutations in the long isoform of the USH2A gene in Chinese families with nonsyndromic retinitis pigmentosa and Usher syndrome Type II," Mol Vis., 2011, 17:1537-1552.
Yan et al., "Mutation analysis in the long isoform of USH2A in American patients with Usher Syndrome type II," J Hum Genet, 2009, 54(12):732-8.
Young et al., "A Single CRISPR-Cas9 Deletion Strategy that Targets the Majority of DMD Patients Restores Dystrophin Function in hiPSC-Derived Muscle Cells," Cell Stem Cell, 2016, 18(4):533-40, 9 pages.
Zhang et al., "Knockdown of ttc26 disrupts ciliogenesis of the photoreceptor cells and the pronephros in zebrafish," Mol Biol Cell, 2012, 23(16):3069-78.
Zhang et al., "Processing-Independent CRISPR RNAs Limit Natural Transformation in Neisseria meningitidis, " Mol Cell., 2013, 50:488-503.
Zou et al., "Deletion of PDZD7 disrupts the Usher syndrome type 2 protein complex in cochlear hair cells and causes hearing loss in mice," Hum Mol Genet, 2014, 23(9):2374-90.
Zou et al., "Individual USH2 proteins make distinct contributions to the ankle link complex during development of the mouse cochlear stereociliary bundle," Hum Mol Genet., Dec. 2015, 24(24):6944-57.
Zou et al., "Whirlin replacement restores the formation of the USH2 protein complex in whirlin knockout photoreceptors," Invest Ophthalmol Vis Sci, Apr. 2011, 52(5):2343-51.
Office Action in Australian Appln. No. 2019237541, mailed on Nov. 15, 2024, 5 pages.
Bornert et al., "Analysis of the functional consequences of targeted exon deletion in COL7A1 reveals prospects for dystrophic epidermolysis bullosa therapy," Molecular Therapy, Jul. 2016, 24(7): 1302-1311.
Devoy et al., "Genomically humanised mice: technologies and promise," Nature Reviews Genetics, Dec. 2011, 13(1):14-20.
Extended European Search Report in European Appln. No. 24220658.9, mailed on May 13, 2025, 10 pages.
Pendse et al., "Exon 13-skipped USH2A protein retains functional integrity in mice, suggesting an exo-skipping therapeutic approach to treat USH2A-associated disease," bioRxiv preprint, posted on Feb. 4, 2020, 34 pages.

\* cited by examiner

D NGS Analysis

| Clone | Variants | Sequence with InDels |
|---|---|---|
| Parent 4 | P1 (3bp) | TGCACCATTGGGAATGC------GGAGGGGTGgacacgggggtggctacctggacatcggcaatgtgg |
| Parent 4 | P2 (13bp) | TGCACCATTGGGAATGCAGTACTGCTg-------------gacacgggggtggctacctggacatcggcaatgtgg |
| Parent 4 | P3 | TGCACCATTGGGAATGCAGTACTGCTGAACGGAGGGGTGgacacgggggtggctacctggacatcggcaatgtgg |

| Clone | Variants | Sequence with InDels | NGS |
|---|---|---|---|
| Clone 17 | P1 (20bp) | TTGGGAATGCAGTACTGCTG--------------------gacacggggtggctacc | 21,712 |
| Clone 17 | P2 (7bp) | TTGGGAATGCAGTACTGC-------AGGGGTGgacacggggtggctacc | 21,388 |
| Clone 17 | P3 (13bp) | TTGGGAATGC-------------GGAGGGGTGgacacggggtggctacc | 20,541 |
| Clone J | P1 (7bp) | TTGGGAATGCAGTACTG-------GAGGGGTGgacacggggtggctacc | 36,600 |
| Clone J | P2 (1bp) | TTGGGAATGCAGTACTGCTGAA-GGAGGGGTGgacacggggtggctacc | 22,613 |

FIG. 2D

| Guide Name | Sequence | PAM |
|---|---|---|
| mUSH2A Intron 11 A | ACCTCCGAGAGGACCCCTCC | AGG |
| mUSH2A Intron 11 B | ATTTAGCTCTACTAAGCGAG | AGG |
| mUSH2A Intron 11 C | GGATGATTCGTGACTGCTTG | AGG |
| mUSH2A Intron 12 A | ACGTCAAATAGCTCGGTTTGGA | TGG |
| mUSH2A Intron 12 C | GGGGAAAGGAGCCACTTTAG | AGG |
| mUSH2A Intron 12 D | GGTATCATAAGGATCCATCT | AGG |

C

D

SEQUENCE LISTING

<160> NUMBER OF SEQ ID NOS: 189

<210> SEQ ID NO 1
<211> LENGTH: 18241

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
tgtttgctct gcagaatact ttacctgggc acccaagtct tccttccagc attcctgctg    60
ctacagccta tttgctgagt aaccaggggt tacagcagcg ttgccaggca acgagggaca   120
gcggtcctgt tgaagagcca tttgtcacac tgaggggact ggttgaaatg caataaagaa   180
atgataccag cagctactca tgtcttcgcc attgctaaga acgtcgttgg tattaccta    240
ctctgagaac gtgtctgcag tttccagaaa atggagtatc gcaacatcac ttaaagtacc   300
ctgcttcaaa gtattgctgg caagtggcgt gggcctgatt atttatttag aaatgcttta   360
tcaggaggag aatgcttttt tgtaaacatg aattgcccag ttctttcatt gggctctggc   420
ttcttgtttc aggtcattga atgttgatc tttgcctatt ttgcttcaat atccttgact    480
gagtcacgag gtcttttccc aaggctggag aacgtgggag ctttcaagaa agtttccatc   540
gtgccaaccc aagcagtatg tggactccca gaccgaagca ctttttgtca cagctctgct   600
gctgctgaaa gtattcagtt ctgtacccag cggttttgta ttcaggattg cccatacaga   660
tcttcacacc ctacctacac tgcccttttc tcagcaggcc tcagtagctg catcacacca   720
gacaagaatg atctgcatcc taacgccat agcaattctg caagttttat ttttggaaat   780
cacaagagct gcttttcttc tcctccttct ccaaagctga tggcatcatt taccttagct   840
gtatggctga aacctgagca acaaggtgta atgtgtgtta tagaaaagac agtagatggg   900
cagattgtgt tcaaacttac aatatctgag aaagagacca tgttttatta tcgcacagta   960
aatggtttgc aacctccaat aaaagtaatg acactgggga gaattcttgt gaagaaatgg  1020
attcatctta gtgtgcaggt gcatcagaca aaaatcagct tctttatcaa tggcgtggag  1080
aaggatcata caccttttcaa tgcaagaact ctaagtggtt caattacaga ttttgcatct  1140
ggtactgtgc aaataggaca gagttaaat ggtttagagc agtttgtcgg aagaatgcaa   1200
gattttcgat taccaagt ggcacttaca acagagaga ttctggaagt cttctctgga    1260
gatcttctca gattgcatgc ccaatcacat tgccgttgcc ctggcagcca cccgcgggtc  1320
caccctttgg cacagcggta ctgcattcct aatgatgcag gagacacagc tgataataga  1380
gtgtcacggt tgaatcctga agcccatcct ctctctttg tcaatgataa tgatgttggt   1440
acttcatggg tttcaaatgt gtttacaaac attacacagc ttaatcaagg agtgactatt  1500
tcagttgatt tggaaatgg acagtatcag gtgttttata ttatcattca gttcttagt    1560
ccacaaccaa cggaaataag gattcaaagg aagaaggaaa atagtttaga ttgggaggac  1620
tggcaatat ttgccaggaa ttgtggtgct tttggaatga aaaacaatgg agatttggaa   1680
aaacctgatt ctgtcaactg tcttcagctt ccaatttta ctccatattc ccgtggcaat   1740
gtcacattta gcatcctgac acctggacca aattatcgtc ctggatacaa taacttctat  1800
aatacccccat ctcttcaaga gttcgtaaaa gccacgcaaa taaggtttca ttttcatggg  1860
cagtactata caactgagac tgctgttaac ctcagacaca gatattatgc agtggacgaa  1920
atcaccatta gtgggagatg tcagtgccat ggtcatgccg ataactgcga cacaacaagc  1980
cagccatata gatgcctctg ctcccaggag agcttcactg aaggacttca ttgtgatcgc  2040
tgcttgcctc tttataatga caagcctttc cgccaaggtg atcaagttta cgctttcaat  2100
tgtaaacctt gtcaatgcaa cagccattcc aaaagctgcc attacaacat ctctgtagac  2160
```

```
ccatttcctt ttgagcactt cagaggggga ggaggagttt gtgatgattg tgagcataac      2220
actacaggaa ggaactgtga gctgtgcaag gattactttt tccgacaagt tggtgcagat      2280
ccttcggcca tagatgtttg caaaccctgt gactgtgata cagttggcac tagaaatggt      2340
agcattcttt gtgatcagat tggaggacag tgtaattgta agagacacgt gtctggcagg      2400
cagtgcaatc agtgccagaa tggattctac aatctacaag agttggatcc tgatggctgc      2460
agtccctgta actgcaatac ctctgggaca gtggatggag atattacctg tcaccaaaat      2520
tcaggccagt gcaagtgcaa agcaaacgtt attggttttt atatttctcc aggcaatgcc      2580
actggctgcc tgccatgctc atgccataca actggtgcag ttaatcacat ctgtaatagc      2640
ctgactggtc agtgtgtttg ccaagatgct tccattgctg ggcaacgttg tgaccaatgc      2700
aaagaccatt actttggatt tgatcctcag actggaagat gtcagccttg taattgtcat      2760
ctctcaggag ccttgaatga aacctgtcac ttggtcacag gccagtgttt ctgtaaacaa      2820
tttgtcactg gctcaaagtg tgatgcttgt gttcccagtg caagccactt ggatgtcaac      2880
aatctattgg gttgcagcaa aactccattc cagcaacctc cgcccagagg acaagttcaa      2940
agttcttctg ctatcaatct ctcctggagt ccacctgatt ctccaaatgc ccactggctt      3000
acttacagtt tactcaggga tggttttgaa atctacacaa cagaggatca atacccatac      3060
agtattcaat acttcttaga cacagacctg ttaccatata ccaaatattc ctattacatt      3120
gagaccacca atgtgcatgg ttcaacaagg agtgtagctg tcacttacaa gacaaaacca      3180
ggggtcccag agggaaactt gactttaagt tatatcattc ctattggctc agactctgtg      3240
acacttacct ggacaacact ctcaaatcaa tctggtccca tagagaaata tattttgtcc      3300
tgtgcccctt tggctggtgg tcagccatgt gtttcctacg aaggtcatga acctcagct      3360 accatctgga atctggttcc atttgccaag tacgattttt ctgtacaggc gtgtactagc      3420
gggggctgtt tacacagctt gcccattaca gtgaccacag cccaggcccc tccccaaaga      3480
ctaagtccac ctaagatgca gaaaatcagt tctacagaac ttcatgtaga atggtctcca      3540
ccagcggaac taaatggaat aattataaga tatgaactat acatgagaag actgagatct      3600
actaaagaaa ccacatctga ggaaagtcga gttttttcaga gcagtggttg gctcagtcct      3660
cattcatttg tagaatcggc caatgaaaat gcattaaaac ctcctcaaac aatgacaacc      3720
atcactggct tggagccata caccaagtat gagttcagag tcttagctgt gaatatggct      3780
ggaagtgtgt cttctgcctg ggtctcagaa agaacgggag aatcagcacc tgtattcatg      3840
atccctcctt cagtctttcc cctctcttcg tactctctca atatctcctg ggagaagcca      3900
gcagataatg ttacaagagg aaaagttgtg gggtatgaca tcaatatgct ttctgaacaa      3960
tcacctcaac agtctattcc catggcgttt tcacagctgt tgcacactgc taaatcccaa      4020
gaactatctt acactgtaga aggactgaaa ccttatagga tatatgagtt tactattact      4080
ctctgcaatt cagttggttg tgtgaccagt gcttcgggag caggacaaac tttagcagca      4140
gcaccagcac aactgaggcc acctctggtt aaaggaatca acagcacaac aatccatctt      4200
aagtggtttc cacctgaaga actgaatgga ccctctccta tatatcagct ggaaaggaga      4260
gagtcatctc taccagctct gatgaccacg atgatgaaag gaatccgttt cataggaaat      4320
gggtattgta aatttcccag ctccactcac ccagtcaata cagacttcac tggcattaag      4380
gccagctttc gaacaaaagt gcctgaaggt ttgattgtct ttgcagcatc acctggcaat      4440
caggaagagt attttgcact tcagttgaag aagggacgtc tttatttctc ttttgatcct      4500
```

```
caggggtcac cagtggaagt aactacaact aatgatcatg gcaaacaata tagtgatgga      4560
aaatggcatg aaataattgc tattaggcat caggcttttg gccaaatcac tctggatggg      4620
atatatacag gttcctctgc catcctgaat ggtagtactg ttattggaga taacacagga      4680
gtctttctgg gagggctccc gcgaagttat accatcctca ggaaggatcc tgagataatc      4740
caaaaaggtt ttgtgggctg tctcaaggat gtacatttta tgaagaatta caatccgtca      4800
gctatttggg aacctctgga ttggcagagt tctgaagaac aaatcaacgt gtataacagc      4860
tgggagggat gtcccgcttc attaaatgag ggagctcagt cctaggagca gggttcctg       4920 gaacttcatc catatatgtt tcatggtgga atgaactttg agatttcctt taagttcaga      4980
actgaccaat taaatggatt gcttcttttc gtttataaca aagatggacc tgattttctt      5040
gctatggagc tgaaaagtgg aatattgacc ttccggttaa ataccagtct tgcctttaca      5100
caagtggatc tattgctggg gctatcctat tgtaatggaa agtggaataa agtcattatt      5160
aaaaaggaag gctctttcat atcagcaagt gtgaatggac tgatgaagca tgcatcggag      5220 tccgagacc agccactggt ggtgaattca ccagtttatg tgggaggaat cccacaggaa       5280
ctgctgaact cttatcaaca tttgtgtttg gaacaaggtt tcggtggttg catgaaggat      5340
gttaaattta cacggggtgc tgtcgttaac ttggcatctg tgtccagcgg tgctgtcaga      5400
gtcaatctgg atggatgcct atcaactgac agtgctgtta actgcagggg aaatgactcc      5460
atcctggttt accaggaaaa agagcagagt gtttacgagg tggtctcca gccttttaca       5520 gaatacctgt atcgagtgat agcctcgcat gaaggaggtt cagtatatag tgattggagt      5580
cgaggacgta acacaggagc agctccacaa agtgtgccaa ctccctcaag agtccgcagc      5640
ttaaatggat acagcattga ggtgacctgg gatgaacctg ttgtcagagg tgtaattgag      5700
aagtacattc tgaaagccta tagtgaggac agcacccgtc caccccgcat gccctctgcc      5760
agtgctgaat ttgtcaatac aagcaacctc acaggcatat tgacaggctt gctacccttc      5820
aaaaactatg cagtaaccct aactgcttgc actttggctg gctgtactga gagctcacat      5880
gcattgaaca tctctactcc acaagaagcc ccacaagagg ttcagccacc agtagccaaa      5940
tcccttccca gttctttgct gctctcctgg aacccaccca aaaaggcaaa tggtattata      6000
actcagtact gtttatacat ggatgggagg ctgatctatt caggcagtga ggagaactac      6060
acagtcacag atttagcagt atttacaccc caccagtttc tactaagtgc atgcacacat      6120
gtgggctgta caaacagttc ctgggtccta ctgtacacag cacagctgcc accagaacac      6180
gtggattccc cagttctgac tgtcctggat tctagaacta tacacataca gtggaaacaa      6240
ccaagaaaaa taagtgggat tctggaacgc tatgtattat atatgtcaaa ccatacacat      6300
gattttacaa tttggagtgt catctataac agtacagaac ttttccagga tcatatgcta      6360
caatacgttt tacctggtaa taaatatctc atcaagctgg gagcttgcac aggtggtggg      6420
tgcacagtga gtgaggccag tgaggcccta actgacgagg acatacccga aggcgtgcca      6480 gccccccaaag cccactcata ttcacctgac tcctttaatg tctcctggac tgagcctgaa      6540
tatccgaatg gtgttatcac gagttatgga ttatatctag atggtatatt aatccacaat      6600
tcctcagaac tcagctatcg tgcttacgga tttgctcctt ggagtttaca ttccttcaga      6660
gtccaagcat gcacggccaa aggttgtgct ctgggcccac tggtggaaaa tcgaactcta      6720
gaagctcctc ctgaaggaac agtaaatgtg tttgtcaaaa cacagggatc ccggaaagcc      6780
cacgtgaggt gggaagcacc ttttcgcccct aatggactct taacacactc agtccttttc      6840
actgggatat tctatgtaga cccagtaggt aataactaca cccttctgaa tgtcacaaaa      6900
```

```
gtcatgtaca gcggagaaga gacaaacctt tgggtgctca tcgatgggct ggttccttt    6960
accaactata ctgtacaagt gaatatttca aatagccaag gcagcttgat aactgatcct    7020
ataacaattg caatgcctcc aggagctcca gatggcgtgc tgcctcccag gctttcatct    7080
gccactccaa ccagtcttca ggttgtctgg tctacaccag ctcgtaataa cgctcctggc    7140
tctcccagat accaactcca gatgaggtct ggcgactcca cccatggatt tctagagtta    7200
ttttccaatc cttctgcatc gttaagctat gaagtgagtg atctccaacc gtacacagag    7260
tatatgtttc ggttggttgc ctccaatgga tttggcagtg cacatagttc ttggattcca    7320
ttcatgaccg cagaggacaa acctggacct gtagttcctc cgattcttct ggatgtgaag    7380
tcaagaatga tgttggtcac ctggcagcat cctagaaaat ccaatggggt tattacccat    7440
tataacattt atctcatgg ccgtctatac ttgagaactc ctggaaatgt cactaattgc     7500
acagtgatgc atttacaccc atacactgcc tataagtttc aggtagaagc ctgcacttca    7560
aaaggatgtt ccctttcacc agagtcccag actgtatgga cactcccagg ggcaccggaa    7620
gggatcccaa gtccagagct gttctctgat actccaacat ctgtgattat atcttggcaa    7680
cccctaccc accccaatgg cttggtgag aatttcacaa ttgagagaag agtcaaagga      7740
aaggaagaag ttactaccct ggtgactctc ccgaggagtc attccatgag gtttattgac    7800
aagacttctg ctcttagccc atggacaaaa tatgaatatc gggtactgat gagcactctt    7860
catggaggca caaacagcag tgcttgggta gaagttacca caagaccctc acgacctgct    7920
ggggtgcagc cacctgtggt gacagtgctg gaacccgatg cagtccaggt cacttggaaa    7980
cccccactca tccagaacgg agacatactt agctatgaga ttcacatgcc tgaccctcac    8040
atcactttaa ccaatgtgac ttccgcagtg ttaagtcaaa aagttactca tctgattcct    8100
ttcactaatt attctgtcac cattgttgct tgctcagggg gtaatgggta ccttggaggg    8160
tgcacagaga gtttacctac ctatgttacc actcacccca ccgtacctca gaatgttggc    8220
ccattgtctg tgattccact aagtgaatca tatgttgtga tttcttggca accaccatcc    8280
aagccaaatg gacctaattt gagatatgag cttctgagac gtaaaatcca gcagccactt    8340
gcatcaaatc ccccagaaga tttaaatcgg tggcacaata tttattcagg aactcagtgg    8400
ctttatgaag ataagggtct tagcaggttt acaacctatg aatatatgct cttcgtacac    8460
aacagtgtgg gttttacacc gagccgagaa gtgactgtga caacgttagc tggtcttcca    8520
gagagaggag ccaatctcac tgcgagtgtc cttaaccaca cagccatcga cgtgaggtgg    8580
gctaaaccaa ctgttcaaga cctacaaggt gaagttgaat attacacact ttttggagt     8640
tctgctacct caaacgactc tctaaaaatc ttgccagatg taaactctca tgtcattggc    8700
cacctaaagc caaacacaga gtattggatc tttatctctg tcttcaatgg agtccacagc    8760
atcaacagtg caggacttca tgcaaccact tgcgatgggg agcctcaggg catgcttcct    8820
ccagaggttg tcatcatcaa cagtacagct gtacgtgtca tctggacatc tccttcaaac    8880
ccaaatggtg ttgtcactga gtattctatc tatgtaaata ataagctcta caagactgga    8940
atgaatgtgc ctgggtcgtt tattctgaga gacctgtctc ccttcactat ctatgacatt    9000
caggttgaag tctgcacaat atatgcctgc gtgaaaagca atggaaccca aattaccact    9060
gtggaagaca ctccaagtga tataccaaca cccacaattc gtggcatcac ttcaagatct    9120
cttcaaattg attgggtgtc tccacggaag ccaaatggca tcattcttgg atatgatctc    9180
ctatggaaaa catggtatcc atgcgctaaa actcaaaagt tagtgcagga tcagagtgat    9240
```

```
gagctctgca aggcagtgag gtgtcaaaaa cctgaatcta tctgtggaca catttgctat    9300
tcttctgaag ctaaggtttg ttgtaacgga gtgctctata accccaagcc tggacatcgc    9360
tgttgtgaag aaaagtatat cccgtttgtt ctgaattcta ctggagtttg ttgtggtggc    9420
cgaatacagg aggcacaacc aaatcatcag tgctgctctg gtattacgc tagaattcta     9480
ccaggtgaag tatgctgtcc agatgaacag cacaatcggg tttctgttgg cattggtgat    9540
tcctgctgtg gcagaatgcc gtactccacc tcaggaaacc agatttgctg tgctgggagg    9600
cttcatgatg gccatggcca gaagtgctgt ggcagacaga ttgtgagcaa cgatttagag    9660
tgttgtggtg gagaagaagg agtggtgtac aatcgccttc caggtatgtt ctgttgtggg    9720
caggattatg tgaatatgtc agataccata tgctgctcag cttccagtgg agagtctaaa    9780
gcacatatta aaagaatga cccggtgcca gtaaaatgct gtgagactga acttattcca     9840
aagagccaga aatgctgtaa tggagttgga tataatcctt tgaaatatgt ttgctctgac    9900
aagatttcaa ctggaatgat gatgaaggaa accaaagagt gcaggatcct ctgcccagca    9960
tctatggaag ccacagaaca ttgtggcagg tgtgacttca actttaccag ccacatttgc   10020
actgtgataa gagggtctca caattccaca gggaaggcat caattgaaga aatgtgttca   10080
tctgccgaag aaaccattca tacagggagt gtaaacacgt actcttacac agatgtgaac   10140
ctcaagccct acatgacata tgagtacagg atttctgcct ggaacagcta tgggcgagga   10200
ctcagcaaag ctgtgagagc cagaacaaaa gaagatgtgc ctcaaggagt gagtcccct    10260
acgtggacca aaatagacaa tcttgaagat acaattgtct taaactggag aaaacctata   10320
caatcaaatg gtcctattat ttactacatc cttcttcgaa atggaattga acgttttcgg   10380
ggaacatcac tgagcttctc tgataaagag ggaattcaac catttcagga atattcatat   10440
cagctgaaag cttgcacggt tgctggctgt gccaccagta gcaaggtagt tgcagctact   10500
acccaaggag ttccggagag catcctgcca ccaagcatca cagccctaag tgcagtggct   10560
ctgcatctga gctggagtgt ccctgagaaa tcaaacggcg tcattaaaga gtaccagatc   10620
aggcaggttg ggaaaggtct catccacact gacaccactg acaggagaca gcatacggtc   10680
acaggtctcc agccatacac caactacagc ttcactctta cagcttgtac atctgctggg   10740
tgcacttcaa gcgagccttt tctaggtcag acactgcagg cagctcctga aggagtttgg   10800
gtgacacctc gacacattat catcaattct acaacagtgg aattatattg gagtctgcca   10860
gaaaagccca atggcctcgt ttctcaatat caattgagtc gtaatggaaa cttgcttttc   10920
ctgggtggca gtgaggagca gaatttcact gataaaaacc tggagcccaa tagcagatac   10980
acttacaagt tagaagtcaa aactggaggt ggcagcagtg ctagtgatga ttacattgtt   11040
caaacaccta tgtcaacacc agaagaaatc tatcctccat ataatatcac agtaattggg   11100
ccttattcta tatttgtagc ttggatacca ccagggatcc tcatcccga aattcctgtg    11160
gagtacaatg tcttactcaa tgatggaagt gtaaccctc tggccttctc cgttggtcat    11220
catcaatcca cccttctgga aaatttgact ccattcacac agtatgagat aaggatacaa   11280
gcatgtcaaa atggaagttg tggagttagc agtaggatgt tgtcaaaac acctgaagca    11340
gccccaatgg atcttaattc tcctgttctt aaggcactgg ggtcagcttg catagagatt   11400
aagtggatgc cacctgaaaa accaaatgga atcatcatca actactttat ttacagacgc   11460
cctgctggca ttgaagagga gtctgtttta tttgtctggt cagaaggagc ccttgaattt   11520
atggatgaag gagacaccct gaggcctttc acactctacg aatatcgggt cagagcctgt   11580
aactccaagg gttcagtgga gagtctgtgg tcattaacac aaactctgga agctccacct   11640
```

```
caagatttc cagctccttg ggctcaagcc acgagtgctc attcagttct gttgaattgg    11700
acaaagccag aatctcccaa tggcattatc tcccattacc gtgtggtcta ccaggagaga    11760
cccgacgatc ctacatttaa cagccctacc gtgcatgctt tcacagtgaa gggaacaagc    11820
catcaagccc acctgtacgg gttagaacca ttcacaacat atcgcattgg tgttgtggct    11880
gcaaaccatg caggagaaat tttaagccct tggactctga ttcaaacctt agaatcttcc    11940
ccaagtggac tgagaaactt tatagtagaa cagaaagaga atggccgggc attgctacta    12000
cagtggtcag aacctatgag aaccaatggt gtgattaaga catacaacat cttcagtgac    12060
gggttcctgg agtactctgg tttgaatcgt cagtttctct tccgccgcct ggatcctttc    12120
actctctaca cactgaccct ggaggcctgc accagagcag gttgtgcaca ctcggcgcct    12180
cagcctctgt ggacagatga agcccctcca gactctcagc tggctcctac tgtccactct    12240
gtgaagtcca ccagtgttga gctgagctgg tctgagcctg ttaacccaaa tggaaaaata    12300
attcgctatg aagtgattcg cagatgcttc gagggaaaag cttggggaaa tcagacgatc    12360
caggccgacg agaaaattgt tttcacagaa tataacactg aaaggaatac atttatgtat    12420
aatgacacag gtttgcaacc atggacgcag tgtgaatata aaatctacac ttggaattca    12480
gctgggcata cctgtagctc ttggaatgtg gtgaggacat tgcaagcacc tccagaaggt    12540
ctctctccac ctgtgatatc ctatgttct atgaatcccc aaaaactgct gatttcctgg    12600
atcccaccag aacagtctaa tggtattatc cagtcctata ggcttcaaag gaatgaaatg    12660
ctctatcctt ttagctttga tcctgtgact ttcaattaca ctgatgaaga gcttcttcct    12720
ttttccacct atagctatgc actccaagcc tgcacgagtg gaggatgctc caccagcaaa    12780
cccaccagca tcacaactct ggaggctgct ccatcagaag tcagccctcc agatctttgg    12840
gccgtcagtg ccactcaaat gaatgtatgt tggtcaccgc ccacagtgca aaatggaaag    12900
attactaaat atttagttag atatgataat aaagagtccc ttgctggcca gggcctgtgc    12960
ctgctggttt cccacctgca gccttactct cagtataact tctcccttgt agcctgcacg    13020
aatggaggtt gcacagctag tgtgtcaaaa tctgcctgga caatggaggc cctgccagag    13080
aacatggact ctccaacatt gcaagtcaca ggctcagaat caatagaaat cacctggaaa    13140
cctccaagaa acccaaatgg ccagatcaga agttatgaac ttaggaggga tggaaccatt    13200
gtatatacag gcttggaaac acgctatcgt gattttactc tcaccccagg tgtggagtat    13260
agctacacag taactgccag caacagccaa ggggtattt tgagtcctct tgtcaaagat    13320
cgaaccagcc cctcagcacc ctcagggatg aacctccaa aattgcaggc cagggtcct    13380 caggagatct tagtgaactg ggaccctcca gtgagaacaa atggtgatat catcaattat    13440
accctcttca tccgtgaact atttgaaaga gaaactaaaa tcatacacat aaacacaact    13500
cataattctt ttggtatgca gtcatatata gtaaaccagc tgaagccatt tcacaggtat    13560
gaaatacgaa ttcaagcgtg caccaccctg ggatgtgcat caagtgactg gacattcata    13620
cagacccctg agattgcacc tttgatgcaa cccctccac atctggaggt acaaatggct    13680
ccaggaggat tccagccaac tgtttctctt ttgtggacag accgctgca gccaaatgga    13740 aaagttttgt attcgaatt atacagaaga caaatagcaa ctcagcctag aaaatccaat    13800
ccagtcctaa tctataacgg aagctcaaca tctttatag attccgaact attgcctttc    13860
acagagtatg agtatcaggt ctgggcagtg aattctgcag aaaagccccc cagtagctgg    13920
acatggtgca gaaccgggcc agccccacca gaaggtctca gagccccac gttccatgtg    13980
```

```
atctcttcta cccaagcagt ggtcaacatc agtgccctg ggaagcccaa cgggatcgtc    14040
agtctctaca ggctgttctc cagcagcgcc catggggctg agacagtgct atccgaaggc    14100
atggccaccc agcagactct ccatggcctt caagccttca ctaactactc tattggagta    14160
gaggcctgca cctgcttcaa ctgttgcagc aaaggaccga cagctgaact gagaacccat    14220
cctgccccac cctcaggact gtcctctcca caaatcggga cgctggcctc aaggacggcc    14280
tccttccggt ggagtccccc catgttcccc aatggtgtca ttcacagcta tgaactccaa    14340
ttccacgtgg cttgccctcc tgactcagcc ctccctgta ctcccagcca aatagaaaca    14400
aagtacacgg ggctggggca gaaagccagc cttgggggtc tccagcccta caccacatac    14460
aagctgagag tggtggcaca acgaggtg ggcagtacgg cttccgagtg gatcagtttc    14520
accacccaaa aagaattgcc tcagtaccga gccccatttt cggtggacag caatttgtct    14580
gtggtgtgtg tgaactggag tgacaccttc ctcctgaacg ccaactgaa ggagtacgtg    14640 ttaaccgacg gagggcgacg cgtgtacagc ggcttggaca ccaccctcta cataccgaga    14700
acggcggaca aaaccttctt tttccaggtc atctgcacga ctgacgaagg aagtgttaag    14760
acgccgttga tccaatatga tacctctact ggacttggct tggtcctaac aactcctggg    14820
aaaaagaagg gatcgcggag caaaagcaca gagttctaca gcgagctgtg gttcatagtg    14880
ttaatggcga tgctgggctt gatcttgttg gccatttttc tgtccctgat actacaaaga    14940
aaaatccaca aagagccata tatcagagaa agacctccct tggtacctct tcagaagagg    15000
atgtctccat tgaatgttta cccaccgggg gaaaaccata tggggttagc cgataccaaa    15060
attccccggt ctgggacacc tgtgagtatc cgcagcaacc ggagtgcatg tgtcctgcgc    15120
atcccgagtc aaaaccaaac cagcctaacc tactcccagg gttctcttca ccgcagcgtc    15180
agccagctca tggacattca agacaagaaa gtcttgatgg acaactcact gtgggaagcc    15240
atcatgggcc acaacagtgg actgtatgtg gatgaagagg acctgatgaa cgccatcaag    15300
gatttcagct cagtgactaa ggaacgcacc acattcacag acacccacct gtaaaggatg    15360
gaaacccaga agacgtaacc ctggaatgca aggtctgcac ccatttcctc ctgggttatc    15420
actcacacat cataaatgct gaaaagccat tgtttattat cctataattc tttaaagaaa    15480
tgatgactgt ttttgaaagt gttccttcct aatagaggtc taagaaatga tattttctc    15540 atcttaaatg agagagaata ttcatatgaa aatacttgat ttgctcttat tttgtagaag    15600
acaaagaagt atgtaattgt cacttggttc tgtttggcag tgatgctcct ggttaactga    15660
ataatcagtg gcaatttcaa gatggctcac agttgttaga agtagtaagt tagttactgg    15720
ctcaaaaatg attctgttga aaggatgtca ctgctgttca tttctatctg ccatttctgt    15780
cagggttgac acaatcctgc aagaatagtt attctaatga tcacagctgc taaatgaatc    15840
ccaaactttg caccaggtcg acaaactttt ctgaaggttc tatttattta ccatacatag    15900
ggttacttac caaactttt gacaaggctg aaggttctat ttatttacaa tacatagggt    15960
tactcaccaa acttttgac aaggcaacac ataacttaca cataaatgtc tctgttcttg    16020
catttatgaa ttttccaaaa atctaaggag taaacagctt atttatacat tttgaggaga    16080
aaacaaagtg tttcactagg aacacctcta cttgaaccaa tgttttatt tcatatattt    16140 tatagttttg aaactagttt ctcataaaat tctgtcaatt cactgaatat cagagaatac    16200
tgacatcttc aacctagcac atttcaaatg gaaactactg ttctatttgc aatattaggc    16260
tgcgtgaaat tttaaaagga aaaatgtatc tgttccttct agcattaaca tatatacatg    16320
tagagacaag actataccta tgtgtatata tatgtatatc atgtatatat tactctgcac    16380
```

```
tatatcccc tttttggag aactagccat tattttagcc acagaatcag taagaacaga    16440
tgatatgcaa cagtaccaat tacggttcaa aaatgtctgt cacctgctct agttggatta    16500
caaagtcatt ggtgaaagtc ctatggcaag aaaaattttc ttgcaaatca tccacataaa    16560
atcagatatt taaatttgtt cttcatggaa aacagagtaa gaaaacctct tgtcttcctt    16620
catccttaaa ggtctttgtg accccaggaa aatattgact ctgtctaaca cacaatagtc    16680
acaatacttt ttgtgaatct acaaccagag acaggcaaaa acttgtaaag taagggatag    16740
tcttacttat tctgcctgaa aacaatgtat taccccaggg cccaacagta aaagattgtg    16800 gacttttttgg gtattgagat ttcatctagc tctgtgagag agcagctcct cagactgacc    16860
aactcctaga caaagtttgc caaccataag tgtcaaaagc acaggccagt attaagcaga    16920
agttctacca ccttattaga actgctataa acaaaagcat ctgaaataat tgtgcacatc    16980
tggcagtgac tgtagaaaat acgaaatata tatttctcgc caagttttta tactttctga    17040
aatgaaaaca taggattgac tagtttactg gttttttattc ccatatgccg attctgggac    17100
aataaagttg tttaaagctg gcacaaataa gcattaacca aggctgtgtc cacctttctgt    17160 gagctactta aggtatatag gaaaggagtg gtcacaaact tgcatcctaa tccttggtgg    17220
actcttctaa gaatacagtt tgctagtcac aaagaatagt ctacaaatat gctttgctag    17280
gttcagaaga ttgagtttat cctgatttttt gaaaaattaa ccaggtatct ttatcactgt    17340 gtattttcc aagcacagta taaaattta acaacgcaca aaaaaataca gaactgcagg    17400 ggatttttatc ttggatcatt atccatttaa tcatctaatt agacatgaac tcagttagct    17460
gaatcattta cattttgact ccatagctta gggcagacag aagcctgtat ggcttctgcc    17520
cagaactctg tcccctgcta catgtctaag tttacttgta tttatttcag agaagaactc    17580
taagatgttg ctttgctact ttaagtggta ttgcgtgcca agcctctatt atacaaacca    17640
tgcagactcg cctctagaga ttctgattcg gttgatctgg ggtgtgtggc tgaggcatca    17700
gtacttttta aagcttccag gtgttctaat gttgagaccc actgatgttc cacaatctgg    17760
aagaaatcat gtacaggaat aatatgctat gcacagggac tatgctcctt ggctcacccc    17820
ttctccctta taacaatga gcagttcttg atgaacctct ttaaatttaa atctcctgac    17880 tcacattta ccaattgtac atgccacatt ctcagcttac gaactaccat gttttgttat    17940
tcttaatatc aactgtttgg taagagtaca gttgttttta tacactctaa gaaatgtgtt    18000
tataatctac tgtaatttcc actaaatgga acccaaatat taatgttatg gtaccatata    18060
ctgatgtaaa aatcatgctg gcatccatga acacaccggt aaataaaaca tagtccaagt    18120
ggaagaattc attaataagg aacttttaat tatgtcacaa atgaatagtt ggtttccaat    18180
gcacaaatat catgtaaact aatctaaaga tggtttgctt aataaatatt tgaatgtgac    18240
c                                                                    18241

<210> SEQ ID NO 2
<211> LENGTH: 4988
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asn Cys Pro Val Leu Ser Leu Gly Ser Gly Phe Leu Phe Gln Val
1               5                   10                  15
```

```
Ile Glu Met Leu Ile Phe Ala Tyr Phe Ala Ser Ile Ser Leu Thr Glu
             20                  25                  30

Ser Arg Gly Leu Phe Pro Arg Leu Glu Asn Val Gly Ala Phe Lys Lys
             35                  40                  45

Val Ser Ile Val Pro Thr Gln Ala Val Cys Gly Leu Pro Asp Arg Ser
         50                  55                  60

Thr Phe Cys His Ser Ala Ala Ala Glu Ser Ile Gln Phe Cys Thr
65                  70                  75                  80

Gln Arg Phe Cys Ile Gln Asp Cys Pro Tyr Arg Ser Ser His Pro Thr
                 85                  90                  95

Tyr Thr Ala Leu Phe Ser Ala Gly Leu Ser Ser Cys Ile Thr Pro Asp
             100                 105                 110

Lys Asn Asp Leu His Pro Asn Ala His Ser Asn Ser Ala Ser Phe Ile
             115                 120                 125

Phe Gly Asn His Lys Ser Cys Phe Ser Ser Pro Pro Ser Pro Lys Leu
             130                 135                 140

Met Ala Ser Phe Thr Leu Ala Val Trp Leu Lys Pro Glu Gln Gln Gly
145                 150                 155                 160

Val Met Cys Val Ile Glu Lys Thr Val Asp Gly Gln Ile Val Phe Lys
                 165                 170                 175

Leu Thr Ile Ser Glu Lys Glu Thr Met Phe Tyr Tyr Arg Thr Val Asn
             180                 185                 190

Gly Leu Gln Pro Pro Ile Lys Val Met Thr Leu Gly Arg Ile Leu Val
             195                 200                 205

Lys Lys Trp Ile His Leu Ser Val Gln Val His Gln Thr Lys Ile Ser
210                 215                 220

Phe Phe Ile Asn Gly Val Glu Lys Asp His Thr Pro Phe Asn Ala Arg
225                 230                 235                 240

Thr Leu Ser Gly Ser Ile Thr Asp Phe Ala Ser Gly Thr Val Gln Ile
                 245                 250                 255

Gly Gln Ser Leu Asn Gly Leu Glu Gln Phe Val Gly Arg Met Gln Asp
             260                 265                 270

Phe Arg Leu Tyr Gln Val Ala Leu Thr Asn Arg Glu Ile Leu Glu Val
         275                 280                 285

Phe Ser Gly Asp Leu Leu Arg Leu His Ala Gln Ser His Cys Arg Cys
290                 295                 300

Pro Gly Ser His Pro Arg Val His Pro Leu Ala Gln Arg Tyr Cys Ile
305                 310                 315                 320

Pro Asn Asp Ala Gly Asp Thr Ala Asp Asn Arg Val Ser Arg Leu Asn
                 325                 330                 335

Pro Glu Ala His Pro Leu Ser Phe Val Asn Asp Asn Asp Val Gly Thr
             340                 345                 350

Ser Trp Val Ser Asn Val Phe Thr Asn Ile Thr Gln Leu Asn Gln Gly
         355                 360                 365

Val Thr Ile Ser Val Asp Leu Glu Asn Gly Gln Tyr Gln Val Phe Tyr
     370                 375                 380

Ile Ile Ile Gln Phe Phe Ser Pro Gln Pro Thr Glu Ile Arg Ile Gln
385                 390                 395                 400

Arg Lys Lys Glu Asn Ser Leu Asp Trp Glu Asp Trp Gln Tyr Phe Ala
                 405                 410                 415

Arg Asn Cys Gly Ala Phe Gly Met Lys Asn Asn Gly Asp Leu Glu Lys
             420                 425                 430

Pro Asp Ser Val Asn Cys Leu Gln Leu Ser Asn Phe Thr Pro Tyr Ser
```

```
                435                 440                 445
Arg Gly Asn Val Thr Phe Ser Ile Leu Thr Pro Gly Pro Asn Tyr Arg
450                 455                 460

Pro Gly Tyr Asn Asn Phe Tyr Asn Thr Pro Ser Leu Gln Glu Phe Val
465                 470                 475                 480

Lys Ala Thr Gln Ile Arg Phe His Phe His Gly Gln Tyr Tyr Thr Thr
                485                 490                 495

Glu Thr Ala Val Asn Leu Arg His Arg Tyr Tyr Ala Val Asp Glu Ile
                500                 505                 510

Thr Ile Ser Gly Arg Cys Gln Cys His Gly His Ala Asp Asn Cys Asp
                515                 520                 525

Thr Thr Ser Gln Pro Tyr Arg Cys Leu Cys Ser Gln Glu Ser Phe Thr
                530                 535                 540

Glu Gly Leu His Cys Asp Arg Cys Leu Pro Leu Tyr Asn Asp Lys Pro
545                 550                 555                 560

Phe Arg Gln Gly Asp Gln Val Tyr Ala Phe Asn Cys Lys Pro Cys Gln
                565                 570                 575

Cys Asn Ser His Ser Lys Ser Cys His Tyr Asn Ile Ser Val Asp Pro
                580                 585                 590

Phe Pro Phe Glu His Phe Arg Gly Gly Gly Val Cys Asp Asp Cys
                595                 600                 605

Glu His Asn Thr Thr Gly Arg Asn Cys Glu Leu Cys Lys Asp Tyr Phe
610                 615                 620

Phe Arg Gln Val Gly Ala Asp Pro Ser Ala Ile Asp Val Cys Lys Pro
625                 630                 635                 640

Cys Asp Cys Asp Thr Val Gly Thr Arg Asn Gly Ser Ile Leu Cys Asp
                645                 650                 655

Gln Ile Gly Gly Gln Cys Asn Cys Lys Arg His Val Ser Gly Arg Gln
                660                 665                 670

Cys Asn Gln Cys Gln Asn Gly Phe Tyr Asn Leu Gln Glu Leu Asp Pro
                675                 680                 685

Asp Gly Cys Ser Pro Cys Asn Cys Asn Thr Ser Gly Thr Val Asp Gly
                690                 695                 700

Asp Ile Thr Cys His Gln Asn Ser Gly Gln Cys Lys Cys Lys Ala Asn
705                 710                 715                 720

Val Ile Gly Phe Tyr Ile Ser Pro Gly Asn Ala Thr Gly Cys Leu Pro
                725                 730                 735

Cys Ser Cys His Thr Thr Gly Ala Val Asn His Ile Cys Asn Ser Leu
                740                 745                 750

Thr Gly Gln Cys Val Cys Gln Asp Ala Ser Ile Ala Gly Gln Arg Cys
                755                 760                 765

Asp Gln Cys Lys Asp His Tyr Phe Gly Phe Asp Pro Gln Thr Gly Arg
                770                 775                 780

Cys Gln Pro Cys Asn Cys His Leu Ser Gly Ala Leu Asn Glu Thr Cys
785                 790                 795                 800

His Leu Val Thr Gly Gln Cys Phe Cys Lys Gln Phe Val Thr Gly Ser
                805                 810                 815

Lys Cys Asp Ala Cys Val Pro Ser Ala Ser His Leu Asp Val Asn Asn
                820                 825                 830

Leu Leu Gly Cys Ser Lys Thr Pro Phe Gln Gln Pro Pro Arg Gly
                835                 840                 845

Gln Val Gln Ser Ser Ser Ala Ile Asn Leu Ser Trp Ser Pro Pro Asp
850                 855                 860
```

-continued

```
Ser Pro Asn Ala His Trp Leu Thr Tyr Ser Leu Leu Arg Asp Gly Phe
865                 870                 875                 880

Glu Ile Tyr Thr Thr Glu Asp Gln Tyr Pro Tyr Ser Ile Gln Tyr Phe
                885                 890                 895

Leu Asp Thr Asp Leu Leu Pro Tyr Thr Lys Tyr Ser Tyr Tyr Ile Glu
            900                 905                 910

Thr Thr Asn Val His Gly Ser Thr Arg Ser Val Ala Val Thr Tyr Lys
        915                 920                 925

Thr Lys Pro Gly Val Pro Glu Gly Asn Leu Thr Leu Ser Tyr Ile Ile
    930                 935                 940

Pro Ile Gly Ser Asp Ser Val Thr Leu Thr Trp Thr Thr Leu Ser Asn
945                 950                 955                 960

Gln Ser Gly Pro Ile Glu Lys Tyr Ile Leu Ser Cys Ala Pro Leu Ala
                965                 970                 975

Gly Gly Gln Pro Cys Val Ser Tyr Glu Gly His Glu Thr Ser Ala Thr
            980                 985                 990

Ile Trp Asn Leu Val Pro Phe Ala Lys Tyr Asp Phe Ser Val Gln Ala
        995                 1000                1005

Cys Thr Ser Gly Gly Cys Leu His Ser Leu Pro Ile Thr Val Thr
    1010                1015                1020

Thr Ala Gln Ala Pro Pro Gln Arg Leu Ser Pro Lys Met Gln
    1025                1030                1035

Lys Ile Ser Ser Thr Glu Leu His Val Glu Trp Ser Pro Pro Ala
    1040                1045                1050

Glu Leu Asn Gly Ile Ile Ile Arg Tyr Glu Leu Tyr Met Arg Arg
    1055                1060                1065

Leu Arg Ser Thr Lys Glu Thr Ser Glu Glu Ser Arg Val Phe
    1070                1075                1080

Gln Ser Ser Gly Trp Leu Ser Pro His Ser Phe Val Glu Ser Ala
    1085                1090                1095

Asn Glu Asn Ala Leu Lys Pro Pro Gln Thr Met Thr Thr Ile Thr
    1100                1105                1110

Gly Leu Glu Pro Tyr Thr Lys Tyr Glu Phe Arg Val Leu Ala Val
    1115                1120                1125

Asn Met Ala Gly Ser Val Ser Ala Trp Val Ser Glu Arg Thr
    1130                1135                1140

Gly Glu Ser Ala Pro Val Phe Met Ile Pro Ser Val Phe Pro
    1145                1150                1155

Leu Ser Ser Tyr Ser Leu Asn Ile Ser Trp Glu Lys Pro Ala Asp
    1160                1165                1170

Asn Val Thr Arg Gly Lys Val Val Gly Tyr Asp Ile Asn Met Leu
    1175                1180                1185

Ser Glu Gln Ser Pro Gln Gln Ser Ile Pro Met Ala Phe Ser Gln
    1190                1195                1200

Leu Leu His Thr Ala Lys Ser Gln Glu Leu Ser Tyr Thr Val Glu
    1205                1210                1215

Gly Leu Lys Pro Tyr Arg Ile Tyr Glu Phe Thr Ile Thr Leu Cys
    1220                1225                1230

Asn Ser Val Gly Cys Val Thr Ser Ala Ser Gly Ala Gly Gln Thr
    1235                1240                1245

Leu Ala Ala Ala Pro Ala Gln Leu Arg Pro Pro Leu Val Lys Gly
    1250                1255                1260
```

-continued

```
Ile Asn Ser Thr Thr Ile His Leu Lys Trp Phe Pro Pro Glu Glu
1265                1270                1275
Leu Asn Gly Pro Ser Pro Ile Tyr Gln Leu Glu Arg Arg Glu Ser
1280                1285                1290
Ser Leu Pro Ala Leu Met Thr Thr Met Met Lys Gly Ile Arg Phe
1295                1300                1305
Ile Gly Asn Gly Tyr Cys Lys Phe Pro Ser Ser Thr His Pro Val
1310                1315                1320
Asn Thr Asp Phe Thr Gly Ile Lys Ala Ser Phe Arg Thr Lys Val
1325                1330                1335
Pro Glu Gly Leu Ile Val Phe Ala Ala Ser Pro Gly Asn Gln Glu
1340                1345                1350
Glu Tyr Phe Ala Leu Gln Leu Lys Lys Gly Arg Leu Tyr Phe Leu
1355                1360                1365
Phe Asp Pro Gln Gly Ser Pro Val Glu Val Thr Thr Thr Asn Asp
1370                1375                1380
His Gly Lys Gln Tyr Ser Asp Gly Lys Trp His Glu Ile Ile Ala
1385                1390                1395
Ile Arg His Gln Ala Phe Gly Gln Ile Thr Leu Asp Gly Ile Tyr
1400                1405                1410
Thr Gly Ser Ser Ala Ile Leu Asn Gly Ser Thr Val Ile Gly Asp
1415                1420                1425
Asn Thr Gly Val Phe Leu Gly Gly Leu Pro Arg Ser Tyr Thr Ile
1430                1435                1440
Leu Arg Lys Asp Pro Glu Ile Ile Gln Lys Gly Phe Val Gly Cys
1445                1450                1455
Leu Lys Asp Val His Phe Met Lys Asn Tyr Asn Pro Ser Ala Ile
1460                1465                1470
Trp Glu Pro Leu Asp Trp Gln Ser Ser Glu Glu Gln Ile Asn Val
1475                1480                1485
Tyr Asn Ser Trp Glu Gly Cys Pro Ala Ser Leu Asn Glu Gly Ala
1490                1495                1500
Gln Phe Leu Gly Ala Gly Phe Leu Glu Leu His Pro Tyr Met Phe
1505                1510                1515
His Gly Gly Met Asn Phe Glu Ile Ser Phe Lys Phe Arg Thr Asp
1520                1525                1530
Gln Leu Asn Gly Leu Leu Leu Phe Val Tyr Asn Lys Asp Gly Pro
1535                1540                1545
Asp Phe Leu Ala Met Glu Leu Lys Ser Gly Ile Leu Thr Phe Arg
1550                1555                1560
Leu Asn Thr Ser Leu Ala Phe Thr Gln Val Asp Leu Leu Leu Gly
1565                1570                1575
Leu Ser Tyr Cys Asn Gly Lys Trp Asn Lys Val Ile Ile Lys Lys
1580                1585                1590
Glu Gly Ser Phe Ile Ser Ala Ser Val Asn Gly Leu Met Lys His
1595                1600                1605
Ala Ser Glu Ser Gly Asp Gln Pro Leu Val Val Asn Ser Pro Val
1610                1615                1620
Tyr Val Gly Gly Ile Pro Gln Glu Leu Leu Asn Ser Tyr Gln His
1625                1630                1635
Leu Cys Leu Glu Gln Gly Phe Gly Gly Cys Met Lys Asp Val Lys
1640                1645                1650
Phe Thr Arg Gly Ala Val Val Asn Leu Ala Ser Val Ser Ser Gly
```

-continued

```
               1655                1660                1665

Ala Val Arg Val Asn Leu Asp Gly Cys Leu Ser Thr Asp Ser Ala
        1670                1675                1680

Val Asn Cys Arg Gly Asn Asp Ser Ile Leu Val Tyr Gln Gly Lys
        1685                1690                1695

Glu Gln Ser Val Tyr Glu Gly Gly Leu Gln Pro Phe Thr Glu Tyr
        1700                1705                1710

Leu Tyr Arg Val Ile Ala Ser His Glu Gly Ser Val Tyr Ser
        1715                1720                1725

Asp Trp Ser Arg Gly Arg Thr Thr Gly Ala Ala Pro Gln Ser Val
        1730                1735                1740

Pro Thr Pro Ser Arg Val Arg Ser Leu Asn Gly Tyr Ser Ile Glu
        1745                1750                1755

Val Thr Trp Asp Glu Pro Val Val Arg Gly Val Ile Glu Lys Tyr
        1760                1765                1770

Ile Leu Lys Ala Tyr Ser Glu Asp Ser Thr Arg Pro Pro Arg Met
        1775                1780                1785

Pro Ser Ala Ser Ala Glu Phe Val Asn Thr Ser Asn Leu Thr Gly
        1790                1795                1800

Ile Leu Thr Gly Leu Leu Pro Phe Lys Asn Tyr Ala Val Thr Leu
        1805                1810                1815

Thr Ala Cys Thr Leu Ala Gly Cys Thr Glu Ser Ser His Ala Leu
        1820                1825                1830

Asn Ile Ser Thr Pro Gln Glu Ala Pro Gln Glu Val Gln Pro Pro
        1835                1840                1845

Val Ala Lys Ser Leu Pro Ser Ser Leu Leu Ser Trp Asn Pro
        1850                1855                1860

Pro Lys Lys Ala Asn Gly Ile Ile Thr Gln Tyr Cys Leu Tyr Met
        1865                1870                1875

Asp Gly Arg Leu Ile Tyr Ser Gly Ser Glu Glu Asn Tyr Thr Val
        1880                1885                1890

Thr Asp Leu Ala Val Phe Thr Pro His Gln Phe Leu Leu Ser Ala
        1895                1900                1905

Cys Thr His Val Gly Cys Thr Asn Ser Ser Trp Val Leu Leu Tyr
        1910                1915                1920

Thr Ala Gln Leu Pro Pro Glu His Val Asp Ser Pro Val Leu Thr
        1925                1930                1935

Val Leu Asp Ser Arg Thr Ile His Ile Gln Trp Lys Gln Pro Arg
        1940                1945                1950

Lys Ile Ser Gly Ile Leu Glu Arg Tyr Val Leu Tyr Met Ser Asn
        1955                1960                1965

His Thr His Asp Phe Thr Ile Trp Ser Val Ile Tyr Asn Ser Thr
        1970                1975                1980

Glu Leu Phe Gln Asp His Met Leu Gln Tyr Val Leu Pro Gly Asn
        1985                1990                1995

Lys Tyr Leu Ile Lys Leu Gly Ala Cys Thr Gly Gly Cys Thr
        2000                2005                2010

Val Ser Glu Ala Ser Glu Ala Leu Thr Asp Glu Asp Ile Pro Glu
        2015                2020                2025

Gly Val Pro Ala Pro Lys His Ser Tyr Ser Pro Asp Ser Phe
        2030                2035                2040

Asn Val Ser Trp Thr Glu Pro Glu Tyr Pro Asn Gly Val Ile Thr
        2045                2050                2055
```

```
Ser Tyr Gly Leu Tyr Leu Asp Gly Ile Leu Ile His Asn Ser Ser
    2060                2065                2070

Glu Leu Ser Tyr Arg Ala Tyr Gly Phe Ala Pro Trp Ser Leu His
    2075                2080                2085

Ser Phe Arg Val Gln Ala Cys Thr Ala Lys Gly Cys Ala Leu Gly
    2090                2095                2100

Pro Leu Val Glu Asn Arg Thr Leu Glu Ala Pro Glu Gly Thr
    2105                2110                2115

Val Asn Val Phe Val Lys Thr Gln Gly Ser Arg Lys Ala His Val
    2120                2125                2130

Arg Trp Glu Ala Pro Phe Arg Pro Asn Gly Leu Leu Thr His Ser
    2135                2140                2145

Val Leu Phe Thr Gly Ile Phe Tyr Val Asp Pro Val Gly Asn Asn
    2150                2155                2160

Tyr Thr Leu Leu Asn Val Thr Lys Val Met Tyr Ser Gly Glu Glu
    2165                2170                2175

Thr Asn Leu Trp Val Leu Ile Asp Gly Leu Val Pro Phe Thr Asn
    2180                2185                2190

Tyr Thr Val Gln Val Asn Ile Ser Asn Ser Gln Gly Ser Leu Ile
    2195                2200                2205

Thr Asp Pro Ile Thr Ile Ala Met Pro Pro Gly Ala Pro Asp Gly
    2210                2215                2220

Val Leu Pro Pro Arg Leu Ser Ser Ala Thr Pro Thr Ser Leu Gln
    2225                2230                2235

Val Val Trp Ser Thr Pro Ala Arg Asn Asn Ala Pro Gly Ser Pro
    2240                2245                2250

Arg Tyr Gln Leu Gln Met Arg Ser Gly Asp Ser Thr His Gly Phe
    2255                2260                2265

Leu Glu Leu Phe Ser Asn Pro Ser Ala Ser Leu Ser Tyr Glu Val
    2270                2275                2280

Ser Asp Leu Gln Pro Tyr Thr Glu Tyr Met Phe Arg Leu Val Ala
    2285                2290                2295

Ser Asn Gly Phe Gly Ser Ala His Ser Ser Trp Ile Pro Phe Met
    2300                2305                2310

Thr Ala Glu Asp Lys Pro Gly Pro Val Val Pro Ile Leu Leu
    2315                2320                2325

Asp Val Lys Ser Arg Met Met Leu Val Thr Trp Gln His Pro Arg
    2330                2335                2340

Lys Ser Asn Gly Val Ile Thr His Tyr Asn Ile Tyr Leu His Gly
    2345                2350                2355

Arg Leu Tyr Leu Arg Thr Pro Gly Asn Val Thr Asn Cys Thr Val
    2360                2365                2370

Met His Leu His Pro Tyr Thr Ala Tyr Lys Phe Gln Val Glu Ala
    2375                2380                2385

Cys Thr Ser Lys Gly Cys Ser Leu Ser Pro Glu Ser Gln Thr Val
    2390                2395                2400

Trp Thr Leu Pro Gly Ala Pro Glu Gly Ile Pro Ser Pro Glu Leu
    2405                2410                2415

Phe Ser Asp Thr Pro Thr Ser Val Ile Ile Ser Trp Gln Pro Pro
    2420                2425                2430

Thr His Pro Asn Gly Leu Val Glu Asn Phe Thr Ile Glu Arg Arg
    2435                2440                2445
```

```
Val Lys Gly Lys Glu Glu Val Thr Thr Leu Val Thr Leu Pro Arg
2450                2455                2460

Ser His Ser Met Arg Phe Ile Asp Lys Thr Ser Ala Leu Ser Pro
2465                2470                2475

Trp Thr Lys Tyr Glu Tyr Arg Val Leu Met Ser Thr Leu His Gly
2480                2485                2490

Gly Thr Asn Ser Ser Ala Trp Val Glu Val Thr Thr Arg Pro Ser
2495                2500                2505

Arg Pro Ala Gly Val Gln Pro Pro Val Thr Val Leu Glu Pro
2510                2515                2520

Asp Ala Val Gln Val Thr Trp Lys Pro Pro Leu Ile Gln Asn Gly
2525                2530                2535

Asp Ile Leu Ser Tyr Glu Ile His Met Pro Asp Pro His Ile Thr
2540                2545                2550

Leu Thr Asn Val Thr Ser Ala Val Leu Ser Gln Lys Val Thr His
2555                2560                2565

Leu Ile Pro Phe Thr Asn Tyr Ser Val Thr Ile Val Ala Cys Ser
2570                2575                2580

Gly Gly Asn Gly Tyr Leu Gly Gly Cys Thr Glu Ser Leu Pro Thr
2585                2590                2595

Tyr Val Thr Thr His Pro Thr Val Pro Gln Asn Val Gly Pro Leu
2600                2605                2610

Ser Val Ile Pro Leu Ser Glu Ser Tyr Val Val Ile Ser Trp Gln
2615                2620                2625

Pro Pro Ser Lys Pro Asn Gly Pro Asn Leu Arg Tyr Glu Leu Leu
2630                2635                2640

Arg Arg Lys Ile Gln Gln Pro Leu Ala Ser Asn Pro Pro Glu Asp
2645                2650                2655

Leu Asn Arg Trp His Asn Ile Tyr Ser Gly Thr Gln Trp Leu Tyr
2660                2665                2670

Glu Asp Lys Gly Leu Ser Arg Phe Thr Thr Tyr Glu Tyr Met Leu
2675                2680                2685

Phe Val His Asn Ser Val Gly Phe Thr Pro Ser Arg Glu Val Thr
2690                2695                2700

Val Thr Thr Leu Ala Gly Leu Pro Glu Arg Gly Ala Asn Leu Thr
2705                2710                2715

Ala Ser Val Leu Asn His Thr Ala Ile Asp Val Arg Trp Ala Lys
2720                2725                2730

Pro Thr Val Gln Asp Leu Gln Gly Glu Val Glu Tyr Tyr Thr Leu
2735                2740                2745

Phe Trp Ser Ser Ala Thr Ser Asn Asp Ser Leu Lys Ile Leu Pro
2750                2755                2760

Asp Val Asn Ser His Val Ile Gly His Leu Lys Pro Asn Thr Glu
2765                2770                2775

Tyr Trp Ile Phe Ile Ser Val Phe Asn Gly Val His Ser Ile Asn
2780                2785                2790

Ser Ala Gly Leu His Ala Thr Thr Cys Asp Gly Glu Pro Gln Gly
2795                2800                2805

Met Leu Pro Pro Glu Val Val Ile Ile Asn Ser Thr Ala Val Arg
2810                2815                2820

Val Ile Trp Thr Ser Pro Ser Asn Pro Asn Gly Val Val Thr Glu
2825                2830                2835

Tyr Ser Ile Tyr Val Asn Asn Lys Leu Tyr Lys Thr Gly Met Asn
```

```
               2840                2845                2850
Val Pro Gly Ser Phe Ile Leu Arg Asp Leu Ser Pro Phe Thr Ile
    2855                2860                2865
Tyr Asp Ile Gln Val Glu Val Cys Thr Ile Tyr Ala Cys Val Lys
    2870                2875                2880
Ser Asn Gly Thr Gln Ile Thr Thr Val Glu Asp Thr Pro Ser Asp
    2885                2890                2895
Ile Pro Thr Pro Thr Ile Arg Gly Ile Thr Ser Arg Ser Leu Gln
    2900                2905                2910
Ile Asp Trp Val Ser Pro Arg Lys Pro Asn Gly Ile Ile Leu Gly
    2915                2920                2925
Tyr Asp Leu Leu Trp Lys Thr Trp Tyr Pro Cys Ala Lys Thr Gln
    2930                2935                2940
Lys Leu Val Gln Asp Gln Ser Asp Glu Leu Cys Lys Ala Val Arg
    2945                2950                2955
Cys Gln Lys Pro Glu Ser Ile Cys Gly His Ile Cys Tyr Ser Ser
    2960                2965                2970
Glu Ala Lys Val Cys Cys Asn Gly Val Leu Tyr Asn Pro Lys Pro
    2975                2980                2985
Gly His Arg Cys Cys Glu Glu Lys Tyr Ile Pro Phe Val Leu Asn
    2990                2995                3000
Ser Thr Gly Val Cys Cys Gly Gly Arg Ile Gln Glu Ala Gln Pro
    3005                3010                3015
Asn His Gln Cys Cys Ser Gly Tyr Tyr Ala Arg Ile Leu Pro Gly
    3020                3025                3030
Glu Val Cys Cys Pro Asp Glu Gln His Asn Arg Val Ser Val Gly
    3035                3040                3045
Ile Gly Asp Ser Cys Cys Gly Arg Met Pro Tyr Ser Thr Ser Gly
    3050                3055                3060
Asn Gln Ile Cys Cys Ala Gly Arg Leu His Asp Gly His Gly Gln
    3065                3070                3075
Lys Cys Cys Gly Arg Gln Ile Val Ser Asn Asp Leu Glu Cys Cys
    3080                3085                3090
Gly Gly Glu Glu Gly Val Val Tyr Asn Arg Leu Pro Gly Met Phe
    3095                3100                3105
Cys Cys Gly Gln Asp Tyr Val Asn Met Ser Asp Thr Ile Cys Cys
    3110                3115                3120
Ser Ala Ser Ser Gly Glu Ser Lys Ala His Ile Lys Lys Asn Asp
    3125                3130                3135
Pro Val Pro Val Lys Cys Cys Glu Thr Glu Leu Ile Pro Lys Ser
    3140                3145                3150
Gln Lys Cys Cys Asn Gly Val Gly Tyr Asn Pro Leu Lys Tyr Val
    3155                3160                3165
Cys Ser Asp Lys Ile Ser Thr Gly Met Met Met Lys Glu Thr Lys
    3170                3175                3180
Glu Cys Arg Ile Leu Cys Pro Ala Ser Met Glu Ala Thr Glu His
    3185                3190                3195
Cys Gly Arg Cys Asp Phe Asn Phe Thr Ser His Ile Cys Thr Val
    3200                3205                3210
Ile Arg Gly Ser His Asn Ser Thr Gly Lys Ala Ser Ile Glu Glu
    3215                3220                3225
Met Cys Ser Ser Ala Glu Glu Thr Ile His Thr Gly Ser Val Asn
    3230                3235                3240
```

-continued

```
Thr Tyr Ser Tyr Thr Asp Val Asn Leu Lys Pro Tyr Met Thr Tyr
3245                3250                3255

Glu Tyr Arg Ile Ser Ala Trp Asn Ser Tyr Gly Arg Gly Leu Ser
3260                3265                3270

Lys Ala Val Arg Ala Arg Thr Lys Glu Asp Val Pro Gln Gly Val
3275                3280                3285

Ser Pro Pro Thr Trp Thr Lys Ile Asp Asn Leu Glu Asp Thr Ile
3290                3295                3300

Val Leu Asn Trp Arg Lys Pro Ile Gln Ser Asn Gly Pro Ile Ile
3305                3310                3315

Tyr Tyr Ile Leu Leu Arg Asn Gly Ile Glu Arg Phe Arg Gly Thr
3320                3325                3330

Ser Leu Ser Phe Ser Asp Lys Glu Gly Ile Gln Pro Phe Gln Glu
3335                3340                3345

Tyr Ser Tyr Gln Leu Lys Ala Cys Thr Val Ala Gly Cys Ala Thr
3350                3355                3360

Ser Ser Lys Val Val Ala Ala Thr Thr Gln Gly Val Pro Glu Ser
3365                3370                3375

Ile Leu Pro Pro Ser Ile Thr Ala Leu Ser Ala Val Ala Leu His
3380                3385                3390

Leu Ser Trp Ser Val Pro Glu Lys Ser Asn Gly Val Ile Lys Glu
3395                3400                3405

Tyr Gln Ile Arg Gln Val Gly Lys Gly Leu Ile His Thr Asp Thr
3410                3415                3420

Thr Asp Arg Arg Gln His Thr Val Thr Gly Leu Gln Pro Tyr Thr
3425                3430                3435

Asn Tyr Ser Phe Thr Leu Thr Ala Cys Thr Ser Ala Gly Cys Thr
3440                3445                3450

Ser Ser Glu Pro Phe Leu Gly Gln Thr Leu Gln Ala Ala Pro Glu
3455                3460                3465

Gly Val Trp Val Thr Pro Arg His Ile Ile Ile Asn Ser Thr Thr
3470                3475                3480

Val Glu Leu Tyr Trp Ser Leu Pro Glu Lys Pro Asn Gly Leu Val
3485                3490                3495

Ser Gln Tyr Gln Leu Ser Arg Asn Gly Asn Leu Leu Phe Leu Gly
3500                3505                3510

Gly Ser Glu Glu Gln Asn Phe Thr Asp Lys Asn Leu Glu Pro Asn
3515                3520                3525

Ser Arg Tyr Thr Tyr Lys Leu Glu Val Lys Thr Gly Gly Gly Ser
3530                3535                3540

Ser Ala Ser Asp Asp Tyr Ile Val Gln Thr Pro Met Ser Thr Pro
3545                3550                3555

Glu Glu Ile Tyr Pro Pro Tyr Asn Ile Thr Val Ile Gly Pro Tyr
3560                3565                3570

Ser Ile Phe Val Ala Trp Ile Pro Pro Gly Ile Leu Ile Pro Glu
3575                3580                3585

Ile Pro Val Glu Tyr Asn Val Leu Leu Asn Asp Gly Ser Val Thr
3590                3595                3600

Pro Leu Ala Phe Ser Val Gly His His Gln Ser Thr Leu Leu Glu
3605                3610                3615

Asn Leu Thr Pro Phe Thr Gln Tyr Glu Ile Arg Ile Gln Ala Cys
3620                3625                3630
```

-continued

```
Gln Asn Gly Ser Cys Gly Val Ser Ser Arg Met Phe Val Lys Thr
    3635                3640                3645

Pro Glu Ala Ala Pro Met Asp Leu Asn Ser Pro Val Leu Lys Ala
    3650                3655                3660

Leu Gly Ser Ala Cys Ile Glu Ile Lys Trp Met Pro Pro Glu Lys
    3665                3670                3675

Pro Asn Gly Ile Ile Ile Asn Tyr Phe Ile Tyr Arg Arg Pro Ala
    3680                3685                3690

Gly Ile Glu Glu Glu Ser Val Leu Phe Val Trp Ser Glu Gly Ala
    3695                3700                3705

Leu Glu Phe Met Asp Glu Gly Asp Thr Leu Arg Pro Phe Thr Leu
    3710                3715                3720

Tyr Glu Tyr Arg Val Arg Ala Cys Asn Ser Lys Gly Ser Val Glu
    3725                3730                3735

Ser Leu Trp Ser Leu Thr Gln Thr Leu Glu Ala Pro Pro Gln Asp
    3740                3745                3750

Phe Pro Ala Pro Trp Ala Gln Ala Thr Ser Ala His Ser Val Leu
    3755                3760                3765

Leu Asn Trp Thr Lys Pro Glu Ser Pro Asn Gly Ile Ile Ser His
    3770                3775                3780

Tyr Arg Val Val Tyr Gln Glu Arg Pro Asp Asp Pro Thr Phe Asn
    3785                3790                3795

Ser Pro Thr Val His Ala Phe Thr Val Lys Gly Thr Ser His Gln
    3800                3805                3810

Ala His Leu Tyr Gly Leu Glu Pro Phe Thr Thr Tyr Arg Ile Gly
    3815                3820                3825

Val Val Ala Ala Asn His Ala Gly Glu Ile Leu Ser Pro Trp Thr
    3830                3835                3840

Leu Ile Gln Thr Leu Glu Ser Ser Pro Ser Gly Leu Arg Asn Phe
    3845                3850                3855

Ile Val Glu Gln Lys Glu Asn Gly Arg Ala Leu Leu Leu Gln Trp
    3860                3865                3870

Ser Glu Pro Met Arg Thr Asn Gly Val Ile Lys Thr Tyr Asn Ile
    3875                3880                3885

Phe Ser Asp Gly Phe Leu Glu Tyr Ser Gly Leu Asn Arg Gln Phe
    3890                3895                3900

Leu Phe Arg Arg Leu Asp Pro Phe Thr Leu Tyr Thr Leu Thr Leu
    3905                3910                3915

Glu Ala Cys Thr Arg Ala Gly Cys Ala His Ser Ala Pro Gln Pro
    3920                3925                3930

Leu Trp Thr Asp Glu Ala Pro Pro Asp Ser Gln Leu Ala Pro Thr
    3935                3940                3945

Val His Ser Val Lys Ser Thr Ser Val Glu Leu Ser Trp Ser Glu
    3950                3955                3960

Pro Val Asn Pro Asn Gly Lys Ile Ile Arg Tyr Glu Val Ile Arg
    3965                3970                3975

Arg Cys Phe Glu Gly Lys Ala Trp Gly Asn Gln Thr Ile Gln Ala
    3980                3985                3990

Asp Glu Lys Ile Val Phe Thr Glu Tyr Asn Thr Glu Arg Asn Thr
    3995                4000                4005

Phe Met Tyr Asn Asp Thr Gly Leu Gln Pro Trp Thr Gln Cys Glu
    4010                4015                4020

Tyr Lys Ile Tyr Thr Trp Asn Ser Ala Gly His Thr Cys Ser Ser
```

```
              4025                4030               4035

Trp Asn Val Val Arg Thr Leu Gln Ala Pro Pro Glu Gly Leu Ser
    4040                4045               4050

Pro Pro Val Ile Ser Tyr Val Ser Met Asn Pro Gln Lys Leu Leu
    4055                4060               4065

Ile Ser Trp Ile Pro Pro Glu Gln Ser Asn Gly Ile Ile Gln Ser
    4070                4075               4080

Tyr Arg Leu Gln Arg Asn Glu Met Leu Tyr Pro Phe Ser Phe Asp
    4085                4090               4095

Pro Val Thr Phe Asn Tyr Thr Asp Glu Glu Leu Leu Pro Phe Ser
    4100                4105               4110

Thr Tyr Ser Tyr Ala Leu Gln Ala Cys Thr Ser Gly Gly Cys Ser
    4115                4120               4125

Thr Ser Lys Pro Thr Ser Ile Thr Thr Leu Glu Ala Ala Pro Ser
    4130                4135               4140

Glu Val Ser Pro Pro Asp Leu Trp Ala Val Ser Ala Thr Gln Met
    4145                4150               4155

Asn Val Cys Trp Ser Pro Pro Thr Val Gln Asn Gly Lys Ile Thr
    4160                4165               4170

Lys Tyr Leu Val Arg Tyr Asp Asn Lys Glu Ser Leu Ala Gly Gln
    4175                4180               4185

Gly Leu Cys Leu Leu Val Ser His Leu Gln Pro Tyr Ser Gln Tyr
    4190                4195               4200

Asn Phe Ser Leu Val Ala Cys Thr Asn Gly Gly Cys Thr Ala Ser
    4205                4210               4215

Val Ser Lys Ser Ala Trp Thr Met Glu Ala Leu Pro Glu Asn Met
    4220                4225               4230

Asp Ser Pro Thr Leu Gln Val Thr Gly Ser Glu Ser Ile Glu Ile
    4235                4240               4245

Thr Trp Lys Pro Pro Arg Asn Pro Asn Gly Gln Ile Arg Ser Tyr
    4250                4255               4260

Glu Leu Arg Arg Asp Gly Thr Ile Val Tyr Thr Gly Leu Glu Thr
    4265                4270               4275

Arg Tyr Arg Asp Phe Thr Leu Thr Pro Gly Val Glu Tyr Ser Tyr
    4280                4285               4290

Thr Val Thr Ala Ser Asn Ser Gln Gly Gly Ile Leu Ser Pro Leu
    4295                4300               4305

Val Lys Asp Arg Thr Ser Pro Ser Ala Pro Ser Gly Met Glu Pro
    4310                4315               4320

Pro Lys Leu Gln Ala Arg Gly Pro Gln Glu Ile Leu Val Asn Trp
    4325                4330               4335

Asp Pro Pro Val Arg Thr Asn Gly Asp Ile Ile Asn Tyr Thr Leu
    4340                4345               4350

Phe Ile Arg Glu Leu Phe Glu Arg Glu Thr Lys Ile Ile His Ile
    4355                4360               4365

Asn Thr Thr His Asn Ser Phe Gly Met Gln Ser Tyr Ile Val Asn
    4370                4375               4380

Gln Leu Lys Pro Phe His Arg Tyr Glu Ile Arg Ile Gln Ala Cys
    4385                4390               4395

Thr Thr Leu Gly Cys Ala Ser Ser Asp Trp Thr Phe Ile Gln Thr
    4400                4405               4410

Pro Glu Ile Ala Pro Leu Met Gln Pro Pro Pro His Leu Glu Val
    4415                4420               4425
```

```
Gln Met Ala Pro Gly Gly Phe Gln Pro Thr Val Ser Leu Leu Trp
    4430            4435            4440

Thr Gly Pro Leu Gln Pro Asn Gly Lys Val Leu Tyr Tyr Glu Leu
    4445            4450            4455

Tyr Arg Arg Gln Ile Ala Thr Gln Pro Arg Lys Ser Asn Pro Val
    4460            4465            4470

Leu Ile Tyr Asn Gly Ser Ser Thr Ser Phe Ile Asp Ser Glu Leu
    4475            4480            4485

Leu Pro Phe Thr Glu Tyr Glu Tyr Gln Val Trp Ala Val Asn Ser
    4490            4495            4500

Ala Gly Lys Ala Pro Ser Ser Trp Thr Trp Cys Arg Thr Gly Pro
    4505            4510            4515

Ala Pro Pro Glu Gly Leu Arg Ala Pro Thr Phe His Val Ile Ser
    4520            4525            4530

Ser Thr Gln Ala Val Val Asn Ile Ser Ala Pro Gly Lys Pro Asn
    4535            4540            4545

Gly Ile Val Ser Leu Tyr Arg Leu Phe Ser Ser Ser Ala His Gly
    4550            4555            4560

Ala Glu Thr Val Leu Ser Glu Gly Met Ala Thr Gln Gln Thr Leu
    4565            4570            4575

His Gly Leu Gln Ala Phe Thr Asn Tyr Ser Ile Gly Val Glu Ala
    4580            4585            4590

Cys Thr Cys Phe Asn Cys Cys Ser Lys Gly Pro Thr Ala Glu Leu
    4595            4600            4605

Arg Thr His Pro Ala Pro Pro Ser Gly Leu Ser Ser Pro Gln Ile
    4610            4615            4620

Gly Thr Leu Ala Ser Arg Thr Ala Ser Phe Arg Trp Ser Pro Pro
    4625            4630            4635

Met Phe Pro Asn Gly Val Ile His Ser Tyr Glu Leu Gln Phe His
    4640            4645            4650

Val Ala Cys Pro Pro Asp Ser Ala Leu Pro Cys Thr Pro Ser Gln
    4655            4660            4665

Ile Glu Thr Lys Tyr Thr Gly Leu Gly Gln Lys Ala Ser Leu Gly
    4670            4675            4680

Gly Leu Gln Pro Tyr Thr Thr Tyr Lys Leu Arg Val Val Ala His
    4685            4690            4695

Asn Glu Val Gly Ser Thr Ala Ser Glu Trp Ile Ser Phe Thr Thr
    4700            4705            4710

Gln Lys Glu Leu Pro Gln Tyr Arg Ala Pro Phe Ser Val Asp Ser
    4715            4720            4725

Asn Leu Ser Val Val Cys Val Asn Trp Ser Asp Thr Phe Leu Leu
    4730            4735            4740

Asn Gly Gln Leu Lys Glu Tyr Val Leu Thr Asp Gly Gly Arg Arg
    4745            4750            4755

Val Tyr Ser Gly Leu Asp Thr Thr Leu Tyr Ile Pro Arg Thr Ala
    4760            4765            4770

Asp Lys Thr Phe Phe Phe Gln Val Ile Cys Thr Thr Asp Glu Gly
    4775            4780            4785

Ser Val Lys Thr Pro Leu Ile Gln Tyr Asp Thr Ser Thr Gly Leu
    4790            4795            4800

Gly Leu Val Leu Thr Thr Pro Gly Lys Lys Lys Gly Ser Arg Ser
    4805            4810            4815
```

```
Lys Ser Thr Glu Phe Tyr Ser Glu Leu Trp Phe Ile Val Leu Met
    4820                4825                4830

Ala Met Leu Gly Leu Ile Leu Leu Ala Ile Phe Leu Ser Leu Ile
    4835                4840                4845

Leu Gln Arg Lys Ile His Lys Glu Pro Tyr Ile Arg Glu Arg Pro
    4850                4855                4860

Pro Leu Val Pro Leu Gln Lys Arg Met Ser Pro Leu Asn Val Tyr
    4865                4870                4875

Pro Pro Gly Glu Asn His Met Gly Leu Ala Asp Thr Lys Ile Pro
    4880                4885                4890

Arg Ser Gly Thr Pro Val Ser Ile Arg Ser Asn Arg Ser Ala Cys
    4895                4900                4905

Val Leu Arg Ile Pro Ser Gln Asn Gln Thr Ser Leu Thr Tyr Ser
    4910                4915                4920

Gln Gly Ser Leu His Arg Ser Val Ser Gln Leu Met Asp Ile Gln
    4925                4930                4935

Asp Lys Lys Val Leu Met Asp Asn Ser Leu Trp Glu Ala Ile Met
    4940                4945                4950

Gly His Asn Ser Gly Leu Tyr Val Asp Glu Glu Asp Leu Met Asn
    4955                4960                4965

Ala Ile Lys Asp Phe Ser Ser Val Thr Lys Glu Arg Thr Thr Phe
    4970                4975                4980

Thr Asp Thr His Leu
    4985

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggaatgcagt actgctgaac gg                                              22

<210> SEQ ID NO 4
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tgcaccattg ggaatgcgga ggggtggaca cgggggtggc tacctggaca tcggcaatgt     60
gg                                                                    62

<210> SEQ ID NO 5
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgcaccattg ggaatgcagt actgctggac acggggtgg ctacctggac atcggcaatg     60
tgg                                                                   63
```

<210> SEQ ID NO 6
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgcaccattg ggaatgcagt actgctgaac ggaggggtgg acacgggggt ggctacctgg    60
acatcggcaa tgtgg                                                     75

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ttgggaatgc agtactgctg gacacggggg tggctacc                            38

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttgggaatgc agtactgcag gggtggacac gggggtggct acc                      43

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ttgggaatgc ggaggggtgg acacgggggt ggctacc                             37

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttgggaatgc agtactggag gggtggacac gggggtggct acc                      43

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttgggaatgc agtactgctg aaggaggggt ggacacgggg gtggctacc                49

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
acctccgaga ggacccctcc agg                                            23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atttagctct actaagcgag agg                                            23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggatgattcg tgactgcttg agg                                            23

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
acgtcaaata gctcggtttg gatgg                                          25

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggggaaagga gccactttag agg                                            23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggtatcataa ggatccatct agg                                            23

```
<210> SEQ ID NO 18
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tcctcacctt ttaaatatat tttatcttta gggcttaggt gtgatcattg caattttg        58

<210> SEQ ID NO 19
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tcctcacctt ttaaatatat tttatcttta gggcttaggt gtgatcgttg caattttg        58

<210> SEQ ID NO 20
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tcctcacctt ttaaatatat tttatcttta gggcttaggt gtgatcgttg caattttg        58

<210> SEQ ID NO 21
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 21
nnnnnnnnnn nnnnnnnnnn guuuuaguac ucuggaaaca gaaucuacua aaacaaggca       60
aaaugccgug uuuaucucgu caacuuguug gcgagauuuu uu                        102

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Lys Lys Lys Arg Lys Val
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                               peptide

<400> SEQUENCE: 23

Pro Lys Lys Lys Arg Arg Val
1               5

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Arg Pro Ala Ala Thr Lys Lys Ala Gly Gln Ala Lys Lys Lys Lys
1               5                   10                  15

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tagcaataaa ggatcgttta ttttcattgg aagcgtgtgt tggttttttg atcaggcgcg    60

<210> SEQ ID NO 26
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(24)
<223> OTHER INFORMATION: a, c, t, g, unknown or other
<220> FEATURE:
<221> NAME/KEY: misc_feature
<222> LOCATION: (1)..(24)
<223> OTHER INFORMATION: /note="This region may encompass 16-24
      nucleotides"

<400> SEQUENCE: 26
nnnnnnnnnn nnnnnnnnnn nnnngtttta gtactctgga aacagaatct actaaaacaa    60
ggcaaaatgc cgtgtttatc tcgtcaactt gttggcgaga ttttt                   106

<210> SEQ ID NO 27
<211> LENGTH: 106
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(24)
<223> OTHER INFORMATION: a, c, u, g, unknown or other
<220> FEATURE:
<221> NAME/KEY: misc_feature
<222> LOCATION: (1)..(24)
<223> OTHER INFORMATION: /note="This region may encompass 16-24
      nucleotides"

<400> SEQUENCE: 27
nnnnnnnnnn nnnnnnnnnn nnnnguuuua guacucugga aacagaaucu acuaaaacaa    60
```
ggcaaaaugc cguguuuauc ucgucaacuu guuggcgaga uuuuuu        106

<210> SEQ ID NO 28
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(24)
<223> OTHER INFORMATION: a, c, t, g, unknown or other
<220> FEATURE:
<221> NAME/KEY: misc_feature
<222> LOCATION: (1)..(24)
<223> OTHER INFORMATION: /note="This region may encompass 16-24
      nucleotides"

<400> SEQUENCE: 28
nnnnnnnnnn nnnnnnnnnn nnnngttata gtactctgga aacagaatct actataacaa        60
ggcaaaatgc cgtgtttatc tcgtcaactt gttggcgaga tttttt        106

<210> SEQ ID NO 29
<211> LENGTH: 106
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(24)
<223> OTHER INFORMATION: a, c, u, g, unknown or other
<220> FEATURE:
<221> NAME/KEY: misc_feature
<222> LOCATION: (1)..(24)
<223> OTHER INFORMATION: /note="This region may encompass 16-24
      nucleotides"

<400> SEQUENCE: 29
nnnnnnnnnn nnnnnnnnnn nnnnguuaua guacucugga aacagaaucu acuauaacaa        60
ggcaaaaugc cguguuuauc ucgucaacuu guuggcgaga uuuuuu        106

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gagagcatga tttatattaa        20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggccccctat ggcattgctt        20

<210> SEQ ID NO 32

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gtcctttttt attttcctta                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gtgatggata cattaattag                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggatatttgg aaactatcta                                               20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gcatatcatt taatttcaat                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gtagaaaagc atttcctaaa                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gtcagctgat aactattttt                                               20

<210> SEQ ID NO 38
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gtacttatca tgtttttggg                                             20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gaaaagcatt tcctaaactg g                                           21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gcatatcatt taatttcaat a                                           21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggagagcatg atttatatta a                                           21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gaacttattc attctgtcta g                                           21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gttatttaaa ttcatggata t                                           21

<210> SEQ ID NO 44
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 44
ggcatatcat ttaatttcaa t                                                    21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45 gcccccctatg gcattgcttg t                                                   21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ggtccttttt tattttcctt a                                                    21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ggtgatggat acattaatta g                                                    21

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gttatttaaa ttcatggata tt                                                   22

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gtttgtgtct cgtctatctt ga                                                   22

<210> SEQ ID NO 50
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 50
gataaaaggg tattacaagg ca                                              22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggccccctat ggcattgctt gt                                              22

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggcatatcat ttaatttcaa ta                                              22

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gaaaagcatt tcctaaactg ga                                              22

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gaatttaaat aactcactgc                                                 20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gcttttctac atatgagttc                                                 20

<210> SEQ ID NO 56
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 56
gatgatacga acacaaaata                                                    20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggattaaacc aaaaattgcc                                                    20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ggagtacaca tatacatttt                                                    20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gttaaagaac ttgccttcat                                                    20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gtgctcattt aaaattatag                                                    20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gcagtgagtt atttaaattc                                                    20

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
gatgtttaat aaaaggttaa g                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gtgatggata cattaattag c                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gataaaatat atttaaaagg t                                              21

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gtaaggttat tctaaaagat aa                                             22

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gaacttgcct tcattggagt tc                                             22

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggtgatggat acattaatta gc                                             22

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 68
gaaattaaat gatatgcctt ag                                          22

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gaaggcaagt tctttaacag tg                                          22

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gataaaatag aggagcatac aa                                          22

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gtccccttct gagagagaga                                             20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ggtctatccc tctcccaatt                                             20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ggggtctatc cctctcccaa                                             20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gaaagataag tttgtatata                                           20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gccatatacc catgtagaga                                           20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gaggtaaagt ccccttctga                                           20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ggtggccata tacccatgta                                           20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ggaccactgc agtcaggact                                           20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gaagccacaa accagaaaca                                           20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gaagttacct aagttaacaa                                          20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gtagaaattg agtctcaatt                                          20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gtaatcagtg tcaaccaggt                                          20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gtggtaagta tcccagaaga                                          20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gagaggtaaa gtccccttct                                          20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gtagaattat aaacaatttc                                          20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86

```
ggtaaagtcc ccttctgaga                                             20
```

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87

```
gggtctatcc ctctcccaat                                             20
```

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88

```
gagagaggta aagtcccctt                                             20
```

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89

```
gtaaagtccc cttctgagag a                                           21
```

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90

```
gggtctatcc ctctcccaat t                                           21
```

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91

```
gggtggccat atcccatgt a                                            21
```

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92

```
gctatatgtt ctagttttat a                                           21
```

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gatataaata cagtaatgat t                                            21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gagacaaatg aatatgtatc a                                            21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ggccatatac ccatgtagag a                                            21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gagtcaattc gaattttcct c                                            21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ggtggtaagt atcccagaag a                                            21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gtagaagcca caaaccagaa a                                            21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ggtagaatta taaacaattt c                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gtcaatttta ttttccagag a                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ggaaagataa gtttgtatat a                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ggggtctatc cctctcccaa t                                              21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gtgtaagatc aaagagacaa g                                              21

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gtccccttct gagagagaga ga                                             22

```
<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gatataaata cagtaatgat tt                                                  22

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ggggtctatc cctctcccaa tt                                                  22

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ggctatatgt tctagtttta ta                                                  22

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gtgtagaaat tgagtctcaa tt                                                  22

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gagagaggta aagtcccctt ct                                                  22

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ggtaaagtcc ccttctgaga ga                                                  22

<210> SEQ ID NO 111
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gccgatcgga tttatttcat aa                                              22

<210> SEQ ID NO 112
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gatttttaaa aaactgttaa aa                                              22

<210> SEQ ID NO 113
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gccatatacc catgtagaga aa                                              22

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gagaagttac ctaagttaac aa                                              22

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gtgtaatcag tgtcaaccag gt                                              22

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gtcaatttta ttttccagag aa                                              22

<210> SEQ ID NO 117
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gagaggtaaa gtccccttct ga                                              22

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gaggtaaagt cccttctga ga                                               22

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gtatatggcc accctatgtc cc                                              22

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gtctccataa tcttcctgtc tt                                              22

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gttaaatagt tatatatgtg                                                 20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gaccactgca gtcaggactc                                                 20

<210> SEQ ID NO 123
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 123
gtaagatcaa agagacaaga                                                    20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gggtgtcacg tacttataaa                                                    20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gagacaagaa ggaattgatg                                                    20

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gatttacttc aagtgtagaa a                                                  21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gtccttctcc ttaggttttt a                                                  21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gcatggccca attatcctag g                                                  21

<210> SEQ ID NO 129
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 129
gtgtgatttg cttgccagag a                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gaagttacct aagttaacaa a                                              21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ggaccactgc agtcaggact c                                              21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ggggtgtcac gtacttataa a                                              21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gttaattgat tgcaaatttg a                                              21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gaggtaacca accaaacaaa a                                              21

<210> SEQ ID NO 135
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 135
gtgtaagatc aaagagacaa ga                                              22

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ggtccttctc cttaggtttt ta                                              22

<210> SEQ ID NO 137
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gttataattt ctagaggaaa at                                              22

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gtacgtgaca cccctggcca ca                                              22

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gttttttaaa aatcagatca ac                                              22

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gtcctgtcag ccaatattag ct                                              22

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 141
gccaatatta gctctgagtt at                                              22

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gattaacctg aaggtaaaaa ga                                              22

<210> SEQ ID NO 143
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
tattttatct ttagggctta gg                                              22

<210> SEQ ID NO 144
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
aaatatattt tatctttagg gc                                              22

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
taaatatatt ttatctttag gg                                              22

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ccttttaaat atattttatc tt                                              22

<210> SEQ ID NO 147
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
accttttaaa tatattttat ct                                                22

<210> SEQ ID NO 148
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
caccttttaa atatatttta tc                                                22

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gatcacacct aagccctaaa ga                                                22

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tgatcacacc taagccctaa ag                                                22

<210> SEQ ID NO 151
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
atgatcacac ctaagcccta aa                                                22

<210> SEQ ID NO 152
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
gcaatgatca cacctaagcc ct                                                22

<210> SEQ ID NO 153
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 153
tgcaatgatc acacctaagc cc                                              22

<210> SEQ ID NO 154
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ttgcaatgat cacacctaag cc                                              22

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
attgcaatga tcacacctaa gc                                              22

<210> SEQ ID NO 156
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ccttttaaat atattttatc tt                                              22

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
attttatctt tagggcttag g                                               21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
aatatatttt atctttaggg c                                               21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
```
aaatatattt tatctttagg g         21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
cttttaaata tattttatct t         21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ccttttaaat atattttatc t         21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
accttttaaa tatattttat c         21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
atcacaccta agccctaaag a         21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
gatcacacct aagccctaaa g         21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
tgatcacacc taagccctaa a                                              21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
caatgatcac acctaagccc t                                              21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gcaatgatca cacctaagcc c                                              21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
tgcaatgatc acacctaagc c                                              21

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ttgcaatgat cacacctaag c                                              21

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
cttttaaata tatttatct t                                               21

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ttttatcttt agggcttagg                                                20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
atatatttta tctttagggc                                              20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
aatatatttt atctttaggg                                              20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ttttaaatat attttatctt                                              20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
cttttaaata tattttatct                                              20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ccttttaaat atattttatc                                              20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
tcacacctaa gccctaaaga                                              20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
atcacaccta agccctaaag                                                   20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gatcacacct aagccctaaa                                                   20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
aatgatcaca cctaagccct                                                   20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
caatgatcac acctaagccc                                                   20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
gcaatgatca cacctaagcc                                                   20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
tgcaatgatc acacctaagc                                                   20

```
<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ttttaaatat attttatctt                                                   20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ttttatcttt agggcttagg                                                   20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
aatatatttt atctttaggg                                                   20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
aaattgcaat gatcacacct                                                   20

<210> SEQ ID NO 188
<211> LENGTH: 264
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188
aaggtcgggc aggaagaggg cctatttccc atgattcctt catatttgca tatacgatac        60
aaggctgtta gagagataat tagaattaat ttgactgtaa acacaaagat attagtacaa       120
aatacgtgac gtagaaagta ataatttctt gggtagtttg cagttttaaa attatgtttt       180
aaaatggact atcatatgct taccgtaact tgaaagtatt tcgatttctt ggctttatat       240
atcttgtgga aaggacgaaa cacc                                              264
```

```
<210> SEQ ID NO 189
<211> LENGTH: 40
<212> TYPE: DNA
<213> ORGANISM: Mus sp.

<400> SEQUENCE: 189
attgggaatg cagtactgct gaacggaggg gtggacacgg                              40
```

CRISPR/CAS9-MEDIATED EXON-SKIPPING APPROACH FOR USH2A-ASSOCIATED USHER SYNDROME

CLAIM OF PRIORITY

This application is a 371 U.S. National Stage entry of PCT/US2019/023934, filed on Mar. 25, 2019, which claims the benefit of U.S. Provisional Patent Application Ser. Nos. 62/647,578, filed on Mar. 23, 2018, and 62/794,402, filed on Jan. 18, 2019. The entire contents of the foregoing are hereby incorporated by reference.

SEQUENCE LISTING

The instant application contains a Sequence Listing that has been submitted electronically in ASCII format and is hereby incorporated by reference in its entirety. Said ASCII copy, created on Apr. 17, 2019, is named 00633-0251WO1_SL.txt and is 114,495 bytes in size.

TECHNICAL FIELD

Described herein are compositions for use in treating subjects with USH2A-associated retinal and/or cochlear degeneration that result from mutations in exon 13 of the USH2A gene by deletion of exon 13 from the USH2A gene or transcripts, and methods of use thereof, as well as genetically modified animals and cells.

BACKGROUND

The USH2A gene encodes the transmembrane protein Usherin. Usherin localizes mainly at the periciliary region of mammalian photoreceptors and at the stereocilia or hair bundle of the inner ear hair cells (see, e.g., Maerker et al., Hum Mol Genet. 2008 Jan. 1; 17 (1): 71-86; Liu et al., Proc Natl Acad Sci USA. 2007 Mar. 13; 104 (11): 4413-8). The Usherin protein has a large extracellular domain that is proposed to interact with basement membrane collagen IV and fibronectin via laminin domains (see, e.g., Maerker et al., 2008; Reiners et al., Hum Mol Genet. 2005 Dec. 15; 14 (24): 3933-43). Usherin also interacts with other proteins of USH1 and USH2 complex to form Usher networks (Human Molecular Genetics, 26, 1157-1172).

Mutations in USH2A are the most common cause of both Usher syndrome type II and autosomal recessive retinitis pigmentosa (arRP), accounting for approximately 17% of the recessive RP cases [1, 2]. The impairment of both vision and hearing in Usher syndrome results in a reduced ability of the individual to perceive, communicate, and extract vital information from the environment [3]. Longitudinal regression analysis has showed that the disease course for patients with USH2A mutations can be rapidly progressive, particularly with respect to losing visual field and mobility [4].

SUMMARY

The c.2299delG mutation in exon13 of the USH2A gene is a single basepair deletion that results in a frameshift and premature stop codon, truncating the protein at exon 132 and truncates protein causing ciliary defects. Exon 13 encodes amino acids 723-936, which span 4 of 8 Laminin EGF-like domains in the protein. As not all of these domains appear to be necessary for proper protein function, complete removal of exon 13 can be used to correct the disease phenotype by restoring the proper reading frame of the gene. Exons 12 and 14 are in frame with each other so deletion of exon 13 by a dual-cut approach, in which one gRNA directs a double-strand break to intron 12 and a second gRNA directs a double-strand break to intron 13, is hypothesized to lead to direct splicing of exon 12 to exon 14, thus generating an in-frame coding sequence lacking several of the Laminin EGF-like domains. Alternatively, disrupting the exon 13 splice acceptor site using a single gRNA, would provide similar results. As the protein lacking exon 13 retains functionality, this approach could also be applied to other exon 13 mutations, e.g., as known in the art, e.g., as shown in Table A.

Provided herein are nucleic acids comprising sequences encoding a Cas9 protein, and a first gRNA, and a second gRNA, wherein the first and second gRNAs are targeted to sequences flanking exon 13 of an usherin (USH2A) gene of the subject, preferably wherein the target sequence of the first gRNA is in the 3' 1500 base pairs (bp) of intron 12, and the target sequence of the second gRNA is in the 5' 1500 bp of intron 13 of the USH2A gene. In some embodiments, the first gRNA comprises a target sequence shown in Table 1 or 6A, and/or wherein the second gRNA comprises a target sequence shown in Table 2 or 6B. In some embodiments, the gRNAs comprise In12_307 with In13_318; In12_307 with In13_322; In12_307 with In13_323; In12_307 with In13_327; In12_307 with In13_328; In12_321 with In13_318; In12_321 with In13_322; In12_321 with In13_323; In12_321 with In13_327; or In12_321 with In13_328.

Also provided herein are nucleic acids comprising sequences encoding a Cas9 protein, and a gRNA targeted to a splice acceptor site for exon 13 of an USH2A gene of the subject. In humans, the splice acceptor site is TAGG where TAG is in intron 12 and G is in exon 13. In some embodiments, the gRNA comprises a target sequence shown in Table 3.

In some embodiments, the nucleic acid encodes S. aureus Cas9, preferably wherein the nucleic acid comprises a Cas9 coding sequence according to SEQ ID NO: 10 or encodes a Cas9 comprising the sequence of SEQ ID NO: 11 of WO 2018/026976.

In some embodiments, the sequences encoding Cas9 comprises a nuclear localization signal, e.g., a C-terminal nuclear localization signal and/or an N-terminal nuclear localization signal; and/or wherein the sequences encoding Cas9 comprises a polyadenylation signal.

In some embodiments, the gRNA is a unimolecular S. aureus gRNA comprising SEQ ID NO:7 or SEQ ID NO: 8 of WO 2018/026976, or the corresponding two-part modular S. aureus gRNA, wherein the crRNA component comprises the underlined section and the tracrRNA component comprises the double underlined section of SEQ ID NO:7 or SEQ ID NO:8 of WO 2018/026976.

In some embodiments, the nucleic acid comprises a viral delivery vector. In some embodiments, the viral delivery vector comprises a promoter for Cas9, preferably a CMV, EFS, or hGRK1 promoter. In some embodiments, the viral delivery vector comprises an adeno-associated virus (AAV) vector.

In some embodiments, the nucleic acid comprises: (i) a first guide RNA comprising a targeting domain sequence selected from the group listed in Table 1 or 6a and a second guide RNA comprising a targeting domain sequence selected from the group listed in Table 2 or 6b, or a single guide RNA comprising a targeting domain sequence selected from the group listed in Table 3; (ii) a first and a second inverted terminal repeat sequence (ITR); and (iii) a promoter for driving expression of the Cas9 selected from the group consisting of a CMV, an EFS, or an hGRK1 promoter. In some embodiments, the gRNAs comprise In12_307 with In13_318; In12_307 with In13_322; In12_307 with In13_323; In12_307 with In13_327; In12_307 with In13_328; In12_321 with In13_318; In12_321 with In13_322; In12_321 with In13_323; In12_321 with In13_327; or In12_321 with In13_328.

Also provided are the nucleic acids described herein for use in therapy, for use in preparation of a medicament; and/or for use in a method of treating a subject who has a condition associated with a mutation in exon 13 of USH2A gene.

In some embodiments, the condition is Usher Syndrome type 2 or autosomal recessive retinitis pigmentosa (arRP). In some embodiments, the AAV vector is delivered to a retina of a subject by injection, such as by subretinal injection, or is delivered to the inner ear of a subject by injection, e.g., through the round window.

Also provided herein are transgenic non-human mammal, e.g., a mouse, wherein the genome of the mouse comprises a mouse USH2A gene lacking exon 12 or a mutation in a splice acceptor site for exon 12 of the USH2A gene, and wherein the cells of the mouse express an usherin protein lacking exon 12; and/or wherein the genome of the mouse comprises a human USH2A gene lacking exon 13 or a mutation in a splice acceptor site for exon 13 of the USH2A gene, and wherein the cells of the mouse express an usherin protein lacking exon 13.

Also provided herein are cells, tissue, or organ (e.g., an eye or cochlea) obtained from the transgenic non-human mammals described herein.

Also provided herein are isolated cells, wherein the genome of the cells comprises a human USH2A gene lacking exon 13 or a mutation in a splice acceptor site for exon 13 of the USH2A gene, and wherein the cells express a human usherin protein lacking exon 13, and wherein the cells do not express a functional mouse usherin protein.

In some embodiments, the cell is a cultured mouse cochlear cell. In some embodiments, the cultured mouse cochlear cell is an Oc-K1 cell.

In addition, provided herein is an isolated human usherin protein lacking exon 13, e.g., comprising SEQ ID NO:2, and a nucleic acid encoding the isolated human usherin protein.

In some embodiments, a CRISPR-Cas9 method of altering a cell described herein comprises forming a first double strand break within intron 12 of the human USH2A gene and a forming a second double strand within intron 13 of the human USH2A gene. In various embodiments described herein, the first double strand break is generated using a gRNA targeting domain sequence selected from Table 1 and the second double strand break is generated using a gRNA targeting domain sequence selected from Table 2.

In some embodiments described herein, a CRISPR-Cas9 method of altering a cell is described, which method comprises the step of forming a first double strand break between nucleotides 216,232,137 to 216,246,584 of chromosome 1 and the step of forming a second double strand break between nucleotides 216,247,227 and 216,250,902 of chromosome 1, wherein the first and second double strand breaks are repaired by NHEJ in a manner that results in the removal of exon 13 of the USH2A gene on chromosome 1. In some embodiments, the step of forming the first strand break comprises contacting the cell with a gRNA which comprises a targeting domain sequence selected from Table 1 and the step of forming the second strand break comprises contacting the cell with a gRNA which comprises a targeting domain sequence selected from Table 2. In various embodiments, a gRNA is configured to form a complex with a Cas9 molecule.

In further embodiments, a CRISPR-Cas9 method of altering a cell is described, which method comprises the step of forming a first double strand break between nucleotides 216,248,383 to 216,248,639 of chromosome 1 and the step of forming a second double strand break between nucleotides 216,245,292 and 216,246,542 of chromosome 1, wherein the first and second double strand breaks are repaired by NHEJ in a manner that results in the removal of exon 13 of the USH2A gene on chromosome 1. In some embodiments, the step of forming the first strand break comprises contacting the cell with a gRNA selected from Table 6a and the step of forming the second strand break comprises contacting the cell with a gRNA selected from Table 6b. In various embodiments, the gRNAs selected from Tables 6a and 6b are configured to form a first and second complex with a Cas9 molecule, respectively.

In various embodiments described herein, the cell is from a subject suffering from Usher syndrome type 2A. In some embodiments, the cell is a retinal cell or a photoreceptor cell. In some embodiments, the photoreceptor cell is a cone photoreceptor cell or a cone cell, a rod photoreceptor cell or a rod cell or a macular cone photoreceptor cell.

In some embodiments, a method of altering a cell comprises contacting the cell with a recombinant viral particle comprising:
  (a) a nucleotide sequence encoding a first gRNA molecule comprising a targeting domain sequence selected from Table 1;
  (b) a nucleotide sequence encoding a second gRNA molecule comprising a targeting domain sequence selected from Table 2; and
  (c) a nucleotide sequence encoding a Cas9 molecule;
wherein said viral particle is capable of delivery to a non-dividing cell, and wherein said contacting results in removal of exon 13 of human USH2A gene.

In some embodiments, the viral particle is an AAV viral particle.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIGS. 2A-2D: Generation of null Ush2a cell model in OC-k1 cells. 2A. Schematic illustration of sgRNA (SEQ ID NO:3) for targeting the exon 5 of Ush2a gene on mouse chromosome 1 (SEQ ID NO: 189). 2B. The percentage of in-frame (15%) and out-of-frame (85%) indels introduced by NHEJ in cells transfected with U6-sgRNA and CAG-SpCas9-P2A-GFP plasmids. 2C. Examples of T7E1 assay for individual cell clones after transfection with Cas9/sgRNA. 2D. Allele sequences at the target region of Ush2a gene in clone 4, 17 and J (SEQ ID NOs: 4-11).

DETAILED DESCRIPTION

Figures 1A, 1B:
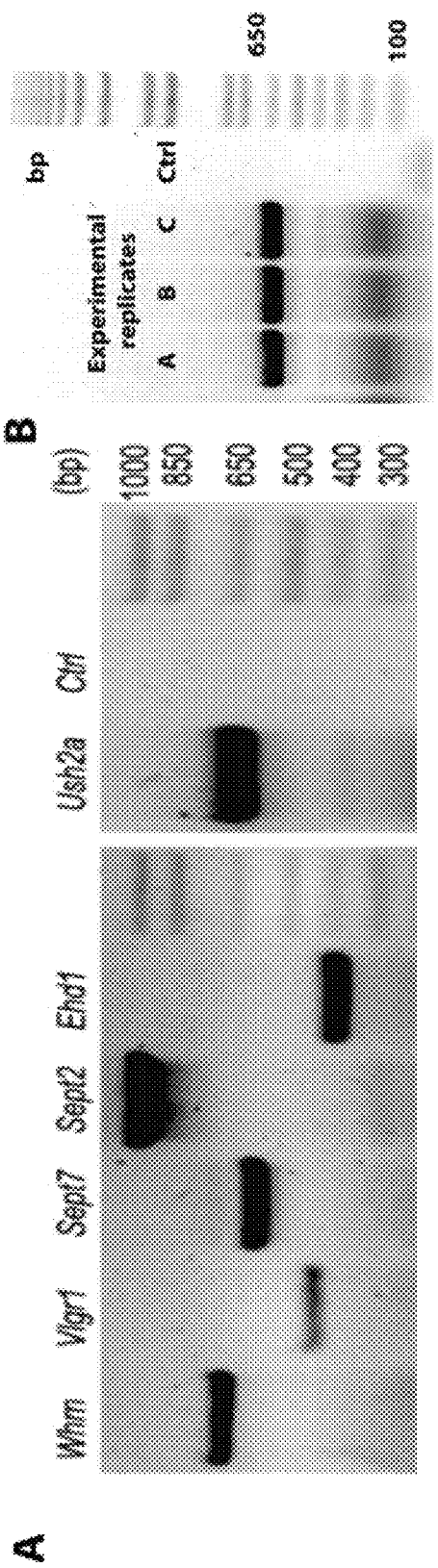
FIGS. 1A-1D: Expression of Ush2a in OC-k1 cells. 1A. RT-PCR assay shows the expression of Ush2a and other cilia proteins, including Whrn, Vlgr1, Sept7, Sept2 and Ehd1, in the OC-k1 cells. 1B. Three experimental replicates of RT-PCR for Ush2a gene in OC-k1 cells. 1C. Ush2a protein detected by anti-Ush2a antibody in OC-1 cells in green. Primary cilia in the OC-k1 cells were labeled with acetylated alpha tubulin in red. 1D. Merged images of 1C, showing that Ush2a protein is localized at the base of primary cilia.

Despite the success of clinical and pre-clinical studies of AAV mediated gene augmentation therapy for multiple genetic types of inherited retinal degeneration [5-13], developing gene therapy for the USH2A form of arRP has been challenging, because the large size of the USH2A coding sequence (CDS15602 bp, 5202aa) far exceeds the packaging capacity of commonly used AAV viral delivery vectors. The present methods overcome these translational barriers by using a Cas9 gene editing approach for USH2A associated arRP [14, 15]. The CRISPR/Cas system is capable of maintaining the edited gene under its endogenous regulatory elements by directly altering the genomic DNA, thereby avoiding ectopic expression and abnormal gene production that may occur with conventional viral-mediated gene augmentation therapies [14, 15].

The usherin protein encoded by USH2A (GenBank Acc No. NC_000001.11, Reference GRCh38.p7 Primary Assembly, Range 215622894-216423396, complement; SEQ ID NO:1) is a transmembrane protein anchored in the photoreceptor plasma membrane (van Wijk, E., et al., Am J Hum Genet, 2004. 74 (4): p. 738-44; Grati, M., et al., J Neurosci, 2012. 32 (41): p. 14288-93). Its extracellular portion, which accounts for over 96% of the length of the protein and projects into the periciliary matrix, is thought to have an important structural and a possible signaling role for the long-term maintenance of photoreceptors (van Wijk, E., et al., Am J Hum Genet, 2004. 74 (4): p. 738-44; Grati, M., et al., J Neurosci, 2012. 32 (41): p. 14288-93). Two isoforms of USH2A have been described. Isoform b (GenBank Acc.

No. NM_206933.2 (transcript) and NP_996816.2 (protein)) is most abundantly expressed in retina and is used as the canonical, standard sequence in the literature and in this application. Usherin is a protein with a high degree of homologous domain structures (Liu, X., et al., Proc Natl Acad Sci USA, 2007. 104 (11): p. 4413-8). Intracellularly, a PDZ domain has been identified to bind whirlin, whereas extracellularly, several domains are present and in most cases in a repetitive fashion, including 10 Laminin EGF-like (LE) domains and 35 Fibronectin type 3 (FN3) domains. These repetitive domains comprise over 78% of the protein structure combined. The most common mutation c.2299delG, p.Glu767fs in USH2A gene, which causes approximately 15%-30% of USH2A cases is USA [19, 20], is located in exon 13 that encodes LE domain 5 (aa 747-794) (Liu, X., et al., Proc Natl Acad Sci USA, 2007. 104 (11): p. 4413-8). Given the high degree of repetitive regions in usherin, it was hypothesized that an usherin protein that lacks one or more of the repetitive domains would retain partial or complete structural integrity and function, such that the abbreviated USH2A can serve as a therapeutic strategy for Usher syndrome type II and autosomal recessive retinitis pigmentosa (arRP) by skipping the mutant exon in USH2A gene.

As shown herein, Ush2a lacking exon 12 and with exons 11 and 13 fused in frame is expressed and localized correctly in the mouse retina and cochlea. When the Ush2a-ΔEx12 allele was expressed on an Ush2a null background, the Ush2a-ΔEx12 protein appeared to rescue the impaired hair cell structure and auditory function as shown by ABR, as compared to Ush2 $^{-/-}$ mice and also showed early signs of at least partial rescue of retinal phenotype. Without wishing to be bound by theory, this data supports the use of the present compositions and methods to restore sight and/or hearing, e.g., at least partially restore sight and/or hearing, in a subject who has Usher syndrome, e.g., associated with a mutation in exon 13 of USH2A gene. Thus a CRISPR/Cas9-based exon-skipping gene editing strategy to restore the reading frame of USH2A by deleting exon 13 holds therapeutic potential for the treatment of USH2A patients.

In one embodiment, an Ush2A nucleic acid molecule includes a nucleotide sequence that is at least about 85% or more identical to the entire length of SEQ ID NO: 1. In some embodiments, the nucleotide sequence is at least about 90%, 91%, 92%, 93%, 94%, 95%, 96%, 97%, 98%, 99% or 100% identical to SEQ ID NO:1.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. In another embodiment, the percent identity of two amino acid sequences can be assessed as a function of the conservation of amino acid residues within the same family of amino acids (e.g., positive charge, negative charge, polar and uncharged, hydrophobic) at corresponding positions in both amino acid sequences (e.g., the presence of an alanine residue in place of a valine residue at a specific position in both sequences shows a high level of conservation, but the presence of an arginine residue in place of an aspartate residue at a specific position in both sequences shows a low level of conservation).

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Methods of Treatment

CRISPR/Cas-based exon-skipping has been successfully used for restoring the expression of functional dystrophin and dystrophic muscle function in the Duchene muscular dystrophy mouse model [21-25]. The methods described herein include methods for the treatment of disorders associated with mutations in exon 13 of the USH2A gene. Exemplary mutations, including 12 nonsense or frameshift mutations and 7 missense mutations on exon 13 (LOVD database), as shown in Table A, such as the most common missense mutation c.2276G>T.

TABLE A

Reported mutations on exon 13 of USH2A gene

| DNA change | Times | Protein change | Nature | Protein domain | References |
|---|---|---|---|---|---|
| c.2209C > T | 19 | p.(Arg737*) | Stop | Laminin EGF-like 4 (694-746) | Auslender et al., 2008 |
| c.2242C > T | 2 | p.(Gln748*) | Stop | Laminin EGF-like 5 (747-794) | Pennings et al., 2004 |
| c.2276G > T | 173 | p.(Cys759Phe) | Missense | Laminin EGF-like 5 (747-794) | Dreyer et al., 2000 |
| c.2299delG | 597 | p.(Glu767Serfs*21) | frameshift | Laminin EGF-like 5 (747-794) | Dreyer et al., 2001 |
| c.2310delA | 1 | p.(Glu771Lysfs*17) | frameshift | Laminin EGF-like 5 (747-794) | Boo et al., 2013 |
| c.2391_2392delTG | 2 | p.(Cys797*) | Stop | Laminin EGF-like 6 (795-846) | Baux et al., 2014 |
| c.2431A > T | 1 | p.(Lys811*) | Stop | Laminin EGF-like 6 (795-846) | Bonnet et al., 2016 |
| c.2431_2432delAA | 5 | p.(Lys811Aspfs*11) | frameshift | Laminin EGF-like 6 (795-846) | Jaijo et al., 2010 |

TABLE A-continued

Reported mutations on exon 13 of USH2A gene

| DNA change | Times | Protein change | Nature | Protein domain | References |
|---|---|---|---|---|---|
| c.2440C > T | 2 | p.(Gln814*) | Stop | Laminin EGF-like 6 (795-846) | Vona et al., 2014 |
| c.2525dup | 1 | p.(Leu843Profs*8) | frameshift | Laminin EGF-like 6 (795-846) | Dreyer et al., 2008 |
| c.2541C > A | 1 | p.(Cys847*) | Stop | Laminin EGF-like 7 (847-899) | Weston et al., 2000 |
| c.2610C > A | 19 | p.(Cys870*) | Stop | Laminin EGF-like 7 (847-899) | Le Quesne Stabej et al., 2012 |
| c.2755C > T | 3 | p.(Gln919*) | Stop | Laminin EGF-like 8 (900-950) | Baux et al., 2014 |
| c.2761delC | 1 | p.(Leu921Cysfs*46) | frameshift | Laminin EGF-like 8 (900-950) | Seyedahmadi et al., 2004 |
| c.2176T > C | 1 | p.(Cys726Arg) | Missense | Laminin EGF-like 4 (694-746) | Besnard, Garcia-Garcia et al., 2014 |
| c.2236C > G | 1 | p.(Pro746Ala) | Missense | Laminin EGF-like 4 (694-746) | Le Quesne Stabej et al., 2012 |
| c.2296T > C | 4 | p.(Cys766Arg) | Missense | Laminin EGF-like 5 (747-794) | — |
| c.2332G > T | 3 | p.(Asp778Tyr) | Missense | Laminin EGF-like 5 (747-794) | Aller et al., 2006 |
| c.2776C > T | 1 | p.(Arg926Cys) | Missense | Laminin EGF-like 8 (900-950) | Zhao et al., 2014 |
| c.2802T > G | 15 | p.(Cys934Trp) | Missense | Laminin EGF-like 8 (900-950) | Xu et al., 2011 |

In some embodiments, the disorder is Usher syndrome, e.g., type 2 Usher syndrome. Subjects with type 2 Usher syndrome typically have moderate to severe hearing loss at birth, and vision that becomes progressively impaired starting in adolescence. In some embodiments, the disorder is autosomal recessive retinitis pigmentosa (arRP). Generally, the methods include administering a therapeutically effective amount of a genome editing system as described herein, to a subject who is in need of, or who has been determined to be in need of, such treatment. The term "genome editing system" refers to any system having RNA-guided DNA editing activity. Genome editing systems of the present disclosure include at least two components adapted from naturally occurring CRISPR systems: a gRNA and an RNA-guided nuclease. These two components form a complex that is capable of associating with a specific nucleic acid sequence in a cell and editing the DNA in or around that nucleic acid sequence, for example by making one or more of a single-strand break (an SSB or nick), a double-strand break (a DSB) and/or a base substitution. See, e.g., WO2018/026976 for a full description of genome editing systems.

As used in this context, to "treat" means to ameliorate at least one symptom of the disorder associated with mutations in exon 13 of the USH2A gene. Often, these mutations result in hearing loss and/or loss of sight; thus, a treatment comprising administration of a therapeutic gene editing system as described herein can result in a reduction in hearing impairment and/or visual impairment; a reduction in the rate of progression of hearing loss and/or vision loss; and/or a return or approach to normal hearing and/or vision. Hearing and vision can be tested using known methods, e.g., electroretinogram, optical coherence tomography, videonystagmography, and audiology testing.

The methods can be used to treat any subject (e.g., a mammalian subject, preferably a human subject) who has a mutation in exon 13 of the USH2A gene, e.g., the c.2299delG mutation or c.2276G>T mutation, e.g., in one or both alleles of USH2A. As used herein, an "allele" is one of a pair or series of genetic variants of a polymorphism (also referred to as a mutation) at a specific genomic location. As used herein, "genotype" refers to the diploid combination of alleles for a given genetic polymorphism. A homozygous subject carries two copies of the same allele and a heterozygous subject carries two different alleles. Methods for identifying subjects with such mutations are known in the art; see, e.g., Yan et al., J Hum Genet. 2009 December; 54 (12): 732-738; Leroy et al., Exp Eye Res. 2001 May; 72 (5): 503-9; or Consugar et al., Genet Med. 2015 April; 17 (4): 253-261. For example, gel electrophoresis, capillary electrophoresis, size exclusion chromatography, sequencing, and/or arrays can be used to detect the presence or absence of the allele or genotype. Amplification of nucleic acids, where desirable, can be accomplished using methods known in the art, e.g., PCR. In one example, a sample (e.g., a sample comprising genomic DNA), is obtained from a subject. The DNA in the sample is then examined to identify or detect the presence of an allele or genotype as described herein. The allele or genotype can be identified or determined by any method described herein, e.g., by Sanger sequencing or Next Generation Sequencing (NGS). Since the exon 13 is 643 bp in size, thus the genotyping of the patients with exon 13 mutations is simple and straight forward using Sanger sequencing or NGS. Other methods can include hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular mutation (also referred to as a polymorphic variant).

Other methods of nucleic acid analysis can include direct manual sequencing (Church and Gilbert, Proc. Natl. Acad.

Sci. USA 81:1991-1995 (1988); Sanger et al., Proc. Natl. Acad. Sci. USA 74:5463-5467 (1977); Beavis et al., U.S. Pat. No. 5,288,644); automated fluorescent sequencing; single-stranded conformation polymorphism assays (SSCP) (Schafer et al., Nat. Biotechnol. 15:33-39 (1995)); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., Proc. Natl. Acad. Sci. USA 86:232-236 (1989)); denaturing high performance liquid chromatography (DHPLC, Underhill et al., Genome Res. 7:996-1005 (1997)); infrared matrix-assisted laser desorption/ionization (IR-MALDI) mass spectrometry (WO 99/57318); mobility shift analysis (Orita et al., Proc. Natl. Acad. Sci. USA 86:2766-2770 (1989)); restriction enzyme analysis (Flavell et al., Cell 15:25 (1978); Geever et al., Proc. Natl. Acad. Sci. USA 78:5081 (1981)); quantitative real-time PCR (Raca et al., Genet Test 8 (4): 387-94 (2004)); heteroduplex analysis; chemical mismatch cleavage (CMC) (Cotton et al., Proc. Natl. Acad. Sci. USA 85:4397-4401 (1985)); RNase protection assays (Myers et al., Science 230:1242 (1985)); use of polypeptides that recognize nucleotide mismatches, e.g., *E. coli* mutS protein; allele-specific PCR, and combinations of such methods. See, e.g., Gerber et al., U.S. Patent Publication No. 2004/0014095 which is incorporated herein by reference in its entirety.

Figure 9:
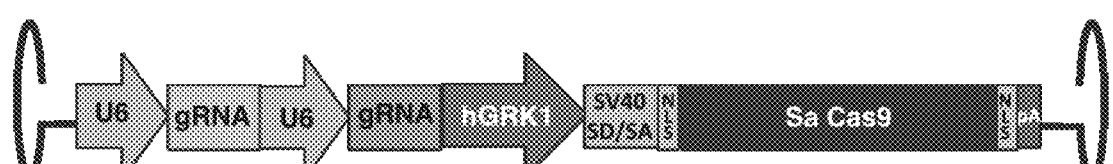
FIG. 9. Schematic illustration of an exemplary AAV vector to deliver SaCas9 and gRNAs. U6, human U6 promoter; hGRK1, human photoreceptor-specific rhodopsin kinase promoter; SV40 SD/SA, SV40 intron sequence; NLS, nuclear localization signal; pA, polyadenylation signal.

In certain aspects, the present disclosure provides AAV vectors encoding CRISPR/Cas9 genome editing systems, and on the use of such vectors to treat USH2A associated disease. Exemplary AAV vector genomes are schematized in FIG. 9, which illustrates certain fixed and variable elements of these vectors: inverted terminal repeats (ITRs), one or two gRNA sequences and promoter sequences to drive their expression, a Cas9 coding sequence and another promoter to drive its expression (an exemplary construct for use in the Method Two described herein would be the same as that illustrated in FIG. 9, but with only 1 gRNA and U6). Each of these elements is discussed in detail herein. Although FIG. 9 shows a single vector used to deliver a Cas9 and two gRNAs, in some embodiments a plurality of vectors are used, e.g., wherein one vector is used to deliver Cas9, and another vector or vectors is used to deliver one or more gRNAs (e.g., one vector for one gRNA, one vector for two gRNAs, or two vectors for each of two gRNAs).

RNA-Guided Nucleases/Cas9

Various RNA-guided nucleases can be used in the present methods, e.g., as described in WO 2018/026976. In some embodiments, the RNA-guided nuclease used in the present methods and compositions is a *S. aureus* Cas9 or a *S. pyogenes* cas9. In some embodiments of this disclosure a Cas9 sequence is modified to include two nuclear localization sequences (NLSs) (e.g., PKKKRKV (SEQ ID NO:22) at the C- and N-termini of the Cas9 protein, and a mini-polyadenylation signal (or Poly-A sequence). An exemplary NLS is SV40 large T antigen NLS (PKKKRRV (SEQ ID NO: 23)) and nucleoplasmin NLS (KRPAATKKAGQAKKKK (SEQ ID NO:24)). Other NLSs are known in the art; see, e.g., Cokol et al., EMBO Rep. 2000 Nov. 15; 1 (5): 411-415; Freitas and Cunha, Curr Genomics. 2009 December; 10 (8): 550-557. An exemplary polyadenylation signal is TAGCAATAAAGGATCGTTTATTTTCATTGGAAGCGTGTG TTGGTTTTTTGATCAGGCGCG (SEQ ID NO:25)). Exemplary *S. aureus* Cas9 sequences (both nucleotide and peptide) are described in Table 4 of WO 2018/026976, e.g., SEQ ID NOs 10 and 11 therein.

Guide RNAS

Figure 8:
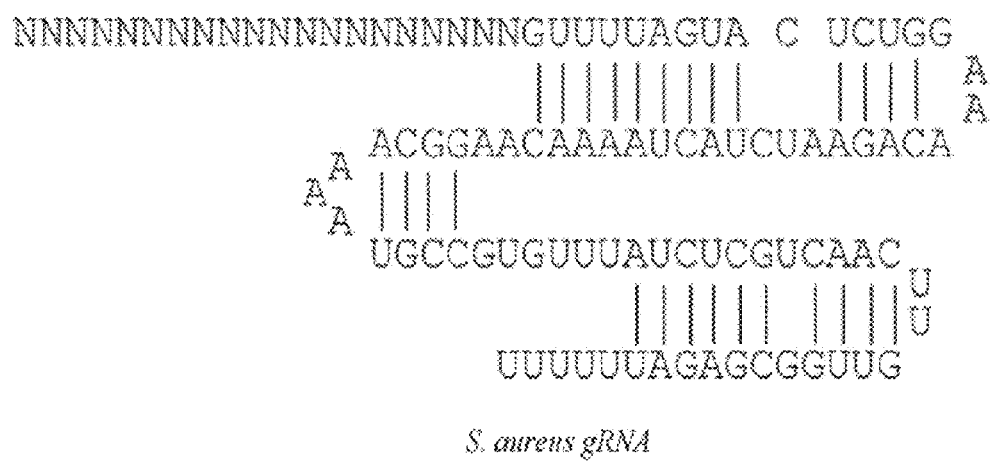
FIG. 8 schematically depicts a gRNA used in certain embodiments of the disclosure (SEQ ID NO:21).

In some embodiments, the gRNAs used in the present disclosure can be unimolecular or modular, as described below. An exemplary unimolecular *S. aureus* gRNA is shown in FIG. 8, and exemplary DNA and RNA sequences corresponding to unimolecular *S. aureus* gRNAs are shown below:

```
DNA:
                                              (SEQ ID NO: 26)
[N16-24]GTTTTAGTACTCTGgaaaCAGAATCTACTAAAACAAGGCAA AATGCCGTGTTTATCTCGTCAACTTGTTGGCGAGATTTTTT
and RNA:
                                              (SEQ ID NO: 27)
[N16-24]GUUUUAGUACUCUGgaaaCAGAAUCUACUAAAACAAGGC

AAAAUGCCGUGUUUAUCUCGUCAACUUGUUGGCGAGAUUUUUU.

DNA:
                                              (SEQ ID NO: 28)
[N16-24]GTTATAGTACTCTGgaaaCAGAATCTACTATAACAAGGCAA AATGCCGTGTTTATCTCGTCAACTTGTTGGCGAGATTTTTT
and RNA:
                                              (SEQ ID NO: 29)
[N16-24]GUUAUAGUACUCUGgaaaCAGAAUCUACUAUAACAAGG CAAAAuGCCGUGUUUAUCUCGUCAACUUGUUGGCGAGAUUUUUU.
```

It should be noted that, while FIG. 8 depicts a targeting domain of 20 nucleotides, the targeting domain can have any suitable length. As indicated by the "N16-24" notation in the sequences above, gRNAs used in the various embodiments of this disclosure preferably include targeting domains of between 16 and 24 (inclusive) bases in length at their 5' ends, and optionally include a 3' U6 termination sequence as illustrated.

The gRNA in FIG. 8 is depicted as unimolecular, but in some instances modular guides can be used. In the exemplary unimolecular gRNA sequences above, a 5' portion corresponding to a crRNA (bold) is connected by a GAAA linker (lower case) to a 3' portion corresponding to a tracrRNA. Skilled artisans will appreciate that two-part modular gRNAs can be used that correspond to the bold and double underlined sections.

Either one of the gRNAs presented above can be used with any of targeting sequences in tables 1-3, and two gRNAs in a pair do not necessarily include the same backbone sequence. Additionally, skilled artisans will appreciate that the exemplary gRNA designs set forth herein can be modified in a variety of ways, which are described below or are known in the art; the incorporation of such modifications is within the scope of this disclosure.

Method One: Dual-gRNA Deletion of Exon 13

Described herein are two approaches for treating subjects with mutations in exon 13 of USH2A. The first makes use of dual-gRNAs for deletion of exon 13. Two gRNAs (one in intron 12, one in intron 13) are used in combination to cut out a segment of DNA including exon 13. In addition to deleting this segment, it may also be inverted and reinserted. In the present studies, inversion of the exon was seen as commonly as deletion, and the inverted version was equally functional; without wishing to be bound by theory, the rearrangement may remove the functional splice sites, so the protein still lacks exon 13 and thus corrects the phenotype.

In some embodiments, this approach uses *Staphylococcus aureus* Cas9 (SaCas9) and corresponding gRNAs. SaCas9 is one of several smaller Cas9 orthologues that are suited for viral delivery (Horvath et al., J Bacteriol 190, 1401-1412 (2008); Ran et al., Nature 520, 186-191 (2015); Zhang et al., Mol Cell 50, 488-503 (2013)). The wild type recognizes a longer NNGRRT PAM that is expected to occur once in every 32 bps of random DNA; or the alternative NNGRRA PAM. Preferably, the 5' base of each gRNA is a G, and the protospacer is length 20, 21 or 22 nucleotides, and the target sequence falls in the 3' 1500 bp of intron 12 or 5' 1500 bp of intron 13.

The methods can include using two gRNAs, one that targets intron 12, and one that targets intron 13. The genomic coordinates of introns 12 and 13 are provided in the following table.

|  | Genomic Coordinates | Focused Genomic Coordinates |
|---|---|---|
| Intron 12 | Chr 1: 216,232,137-216,246,584 | Chr 1: 216,248,383-216,248,639 |
| Intron 13 | Chr 1: 216,247,227-216,250,902 | Chr 1: 216,245,292-216,246,542 |

Tables 1 and 2 provide exemplary sequences for the gRNAs in exons 12 and 13, respectively. Note that in the sequences provided herein, the actual gRNA would have U in place of T.

TABLE 1

Exemplary Guide RNAs for approach 1: Intron 12

| gRNA Name | gRNA sequence | SEQ ID NO: | Length | Strand | hg38 coordinates |
|---|---|---|---|---|---|
| in12_67 | GAGAGCATGATTTATATTAA | 30. | 20 | − | chr1:216248081-216248101 |
| in12_68 | GGCCCCTATGGCATTGCTT | 31. | 20 | − | chr1:216247344-216247364 |
| in12_69 | GTCCTTTTTATTTTCCTTA | 32. | 20 | − | chr1:216248638-216248658 |
| in12_70 | GTGATGGATACATTAATTAG | 33. | 20 | + | chr1:216247802-216247822 |
| in12_71 | GGATATTTGGAAACTATCTA | 34. | 20 | − | chr1:216248361-216248381 |
| in12_72 | GCATATCATTTAATTTCAAT | 35. | 20 | + | chr1:216248619-216248639 |
| in12_73 | GTAGAAAAGCATTTCCTAAA | 36. | 20 | + | chr1:216248500-216248520 |
| in12_74 | GTCAGCTGATAACTATTTTT | 37. | 20 | + | chr1:216247938-216247958 |
| in12_75 | GTACTTATCATGTTTTTGGG | 38. | 20 | − | chr1:216247777-216247797 |
| in12_76 | GAAAAGCATTTCCTAAACTGG | 39. | 21 | + | chr1:216248503-216248524 |
| in12_77 | GCATATCATTTAATTTCAATA | 40. | 21 | + | chr1:216248619-216248640 |
| in12_78 | GGAGAGCATGATTTATATTAA | 41. | 21 | − | chr1:216248081-216248102 |
| in12_79 | GAACTTATTCATTCTGTCTAG | 42. | 21 | − | chr1:216247663-216247684 |
| in12_80 | GTTATTTAAATTCATGGATAT | 43. | 21 | − | chr1:216248375-216248396 |
| in12_81 | GGCATATCATTTAATTTCAAT | 44. | 21 | + | chr1:216248618-216248639 |
| in12_82 | GCCCCTATGGCATTGCTTGT | 45. | 21 | − | chr1:216247342-216247363 |
| in12_83 | GGTCCTTTTTATTTTCCTTA | 46. | 21 | − | chr1:216248638-216248659 |
| in12_84 | GGTGATGGATACATTAATTAG | 47. | 21 | + | chr1:216247801-216247822 |
| in12_85 | GTTATTTAAATTCATGGATATT | 48. | 22 | − | chr1:216248374-216248396 |
| in12_86 | GTTTGTGTCTCGTCTATCTTGA | 49. | 22 | − | chr1:216247274-216247296 |
| in12_87 | GATAAAAGGGTATTACAAGGCA | 50. | 22 | + | chr1:216248288-216248310 |
| in12_88 | GGCCCCTATGGCATTGCTTGT | 51. | 22 | − | chr1:216247342-216247364 |
| in12_89 | GGCATATCATTTAATTTCAATA | 52. | 22 | + | chr1:216248618-216248640 |
| in12_90 | GAAAAGCATTTCCTAAACTGGA | 53. | 22 | + | chr1:216248503-216248525 |
| in12_307 | GAATTTAAATAACTCACTGC | 54. | 20 | + | chr1:216248383-216248403 |
| in12_308 | GCTTTTCTACATATGAGTTC | 55. | 20 | − | chr1:216248490-216248510 |
| in12_309 | GATGATACGAACACAAAATA | 56. | 20 | + | chr1:216247308-216247328 |
| in12_310 | GGATTAAACCAAAAATTGCC | 57. | 20 | − | chr1:216248029-216248049 |

TABLE 1-continued

Exemplary Guide RNAs for approach 1: Intron 12

| gRNA Name | gRNA sequence | SEQ ID NO: | Length | Strand | hg38 coordinates |
|---|---|---|---|---|---|
| in12_311 | GGAGTACACATATACATTTT | 58. | 20 | + | chr1:216248204-216248224 |
| in12_312 | GTTAAAGAACTTGCCTTCAT | 59. | 20 | − | chr1:216248577-216248597 |
| in12_313 | GTGCTCATTTAAAATTATAG | 60. | 20 | + | chr1:216247551-216247571 |
| in12_314 | GCAGTGAGTTATTTAAATTC | 61. | 20 | − | chr1:216248383-216248403 |
| in12_315 | GATGTTTAATAAAAGGTTAAG | 62. | 21 | + | chr1:216247624-216247645 |
| in12_316 | GTGATGGATACATTAATTAGC | 63. | 21 | + | chr1:216247802-216247823 |
| in12_317 | GATAAAATATATTTAAAAGGT | 64. | 21 | + | chr1:216247231-216247252 |
| in12_318 | GTAAGGTTATTCTAAAAGATAA | 65. | 22 | + | chr1:216248271-216248293 |
| in12_319 | GAACTTGCCTTCATTGGAGTTC | 66. | 22 | − | chr1:216248569-216248591 |
| in12_320 | GGTGATGGATACATTAATTAGC | 67. | 22 | + | chr1:216247801-216247823 |
| in12_321 | GAAATTAAATGATATGCCTTAG | 68. | 22 | − | chr1:216248614-216248636 |
| in12_322 | GAAGGCAAGTTCTTTAACAGTG | 69. | 22 | + | chr1:216248579-216248601 |
| in12_323 | GATAAAATAGAGGAGCATACAA | 70. | 22 | − | chr1:216248051-216248073 |

TABLE 2

Exemplary Guide RNAs for approach 1: Intron 13

| gRNA Name | gRNA sequence | SEQ ID NO: | Length | Strand | hg38 coordinates |
|---|---|---|---|---|---|
| in13_73 | GTCCCCTTCTGAGAGAGAGA | 71. | 20 | + | chr1:216245460-216245480 |
| in13_74 | GGTCTATCCCTCTCCCAATT | 72. | 20 | + | chr1:216246017-216246037 |
| in13_75 | GGGGTCTATCCCTCTCCCAA | 73. | 20 | + | chr1:216246015-216246035 |
| in13_76 | GAAAGATAAGTTTGTATATA | 74. | 20 | + | chr1:216246049-216246069 |
| in13_77 | GCCATATACCCATGTAGAGA | 75. | 20 | + | chr1:216245426-216245446 |
| in13_78 | GAGGTAAAGTCCCCTTCTGA | 76. | 20 | + | chr1:216245452-216245472 |
| in13_79 | GGTGGCCATATACCCATGTA | 77. | 20 | + | chr1:216245422-216245442 |
| in13_80 | GGACCACTGCAGTCAGGACT | 78. | 20 | − | chr1:216245556-216245576 |
| in13_81 | GAAGCCACAAACCAGAAACA | 79. | 20 | + | chr1:216246494-216246514 |
| in13_82 | GAAGTTACCTAAGTTAACAA | 80. | 20 | + | chr1:216246518-216246538 |
| in13_83 | GTAGAAATTGAGTCTCAATT | 81. | 20 | + | chr1:216246324-216246344 |
| in13_84 | GTAATCAGTGTCAACCAGGT | 82. | 20 | − | chr1:216246582-216246602 |
| in13_85 | GTGGTAAGTATCCCAGAAGA | 83. | 20 | − | chr1:216245191-216245211 |
| in13_86 | GAGAGGTAAAGTCCCCTTCT | 84. | 20 | + | chr1:216245450-216245470 |
| in13_87 | GTAGAATTATAAACAATTTC | 85. | 20 | + | chr1:216245391-216245411 |
| in13_88 | GGTAAAGTCCCCTTCTGAGA | 86. | 20 | + | chr1:216245454-216245474 |
| in13_89 | GGGTCTATCCCTCTCCCAAT | 87. | 20 | + | chr1:216246016-216246036 |
| in13_90 | GAGAGAGGTAAAGTCCCCTT | 88. | 20 | + | chr1:216245448-216245468 |
| in13_91 | GTAAAGTCCCCTTCTGAGAGA | 89. | 21 | + | chr1:216245455-216245476 |

TABLE 2-continued

Exemplary Guide RNAs for approach 1: Intron 13

| gRNA Name | gRNA sequence | SEQ ID NO: | Length | Strand | hg38 coordinates |
|---|---|---|---|---|---|
| in13_92 | GGGTCTATCCCTCTCCCAATT | 90. | 21 | + | chr1:216246016-216246037 |
| in13_93 | GGGTGGCCATATACCCATGTA | 91. | 21 | + | chr1:216245421-216245442 |
| in13_94 | GCTATATGTTCTAGTTTTATA | 92. | 21 | - | chr1:216246135-216246156 |
| in13_95 | GATATAAATACAGTAATGATT | 93. | 21 | + | chr1:216246455-216246476 |
| in13_96 | GAGACAAATGAATATGTATCA | 94. | 21 | + | chr1:216245514-216245535 |
| in13_97 | GGCCATATACCCATGTAGAGA | 95. | 21 | + | chr1:216245425-216245446 |
| in13_98 | GAGTCAATTCGAATTTTCCTC | 96. | 21 | + | chr1:216245319-216245340 |
| in13_99 | GGTGGTAAGTATCCCAGAAGA | 97. | 21 | - | chr1:216245191-216245212 |
| in13_100 | GTAGAAGCCACAAACCAGAAA | 98. | 21 | + | chr1:216246491-216246512 |
| in13_101 | GGTAGAATTATAAACAATTTC | 99. | 21 | + | chr1:216245390-216245411 |
| in13_102 | GTCAATTTATTTTCCAGAGA | 100. | 21 | - | chr1:216246251-216246272 |
| in13_103 | GGAAAGATAAGTTTGTATATA | 101. | 21 | + | chr1:216246048-216246069 |
| in13_104 | GGGGTCTATCCCTCTCCCAAT | 102. | 21 | + | chr1:216246015-216246036 |
| in13_105 | GTGTAAGATCAAAGAGACAAG | 103. | 21 | - | chr1:216245696-216245717 |
| in13_106 | GTCCCCTTCTGAGAGAGAGA | 104. | 22 | + | chr1:216245460-216245482 |
| in13_107 | GATATAAATACAGTAATGATTT | 105. | 22 | + | chr1:216246455-216246477 |
| in13_365 | GGGGTCTATCCCTCTCCCAATT | 106. | 22 | + | chr1:216246015-216246037 |
| in13_393 | GGCTATATGTTCTAGTTTTATA | 107. | 22 | - | chr1:216246135-216246157 |
| in13_404 | GTGTAGAAATTGAGTCTCAATT | 108. | 22 | + | chr1:216246322-216246344 |
| in13_405 | GAGAGAGGTAAAGTCCCCTTCT | 109. | 22 | + | chr1:216245448-216245470 |
| in13_408 | GGTAAAGTCCCCTTCTGAGAGA | 110. | 22 | + | chr1:216245454-216245476 |
| in13_417 | GCCGATCGGATTTATTTCATAA | 111. | 22 | - | chr1:216246342-216246364 |
| in13_421 | GATTTTTAAAAAACTGTTAAAA | 112. | 22 | + | chr1:216246284-216246306 |
| in13_437 | GCCATATACCCATGTAGAGAAA | 113. | 22 | + | chr1:216245426-216245448 |
| in13_438 | GAGAAGTTACCTAAGTTAACAA | 114. | 22 | + | chr1:216246516-216246538 |
| in13_452 | GTGTAATCAGTGTCAACCAGGT | 115. | 22 | - | chr1:216246582-216246604 |
| in13_454 | GTCAATTTATTTTCCAGAGAA | 116. | 22 | - | chr1:216246250-216246272 |
| in13_460 | GAGAGGTAAAGTCCCCTTCTGA | 117. | 22 | + | chr1:216245450-216245472 |
| in13_466 | GAGGTAAAGTCCCCTTCTGAGA | 118. | 22 | + | chr1:216245452-216245474 |
| in13_472 | GTATATGGCCACCCTATGTCCC | 119. | 22 | - | chr1:216245413-216245435 |
| in13_478 | GTCTCCATAATCTTCCTGTCTT | 120. | 22 | + | chr1:216245173-216245195 |
| in13_314 | GTTAAATAGTTATATATGTG | 121. | 20 | + | chr1:216246426-216246446 |
| in13_315 | GACCACTGCAGTCAGGACTC | 122. | 20 | - | chr1:216245555-216245575 |
| in13_316 | GTAAGATCAAAGAGACAAGA | 123. | 20 | - | chr1:216245695-216245715 |

TABLE 2-continued

Exemplary Guide RNAs for approach 1: Intron 13

| gRNA Name | gRNA sequence | SEQ ID NO: | Length | Strand | hg38 coordinates |
|---|---|---|---|---|---|
| in13_317 | GGGTGTCACGTACTTATAAA | 124. | 20 | − | chr1:216245254-216245274 |
| in13_318 | GAGACAAGAAGGAATTGATG | 125. | 20 | − | chr1:216245684-216245704 |
| in13_319 | GATTTACTTCAAGTGTAGAAA | 126. | 21 | + | chr1:216246310-216246331 |
| in13_320 | GTCCTTCTCCTTAGGTTTTA | 127. | 21 | + | chr1:216245572-216245593 |
| in13_321 | GCATGGCCCAATTATCCTAGG | 128. | 21 | + | chr1:216245739-216245760 |
| in13_322 | GTGTGATTTGCTTGCCAGAGA | 129. | 21 | − | chr1:216245802-216245823 |
| in13_323 | GAAGTTACCTAAGTTAACAAA | 130. | 21 | + | chr1:216246518-216246539 |
| in13_324 | GGACCACTGCAGTCAGGACTC | 131. | 21 | − | chr1:216245555-216245576 |
| in13_325 | GGGGTGTCACGTACTTATAAA | 132. | 21 | − | chr1:216245254-216245275 |
| in13_326 | GTTAATTGATTGCAAATTTGA | 133. | 21 | + | chr1:216245088-216245109 |
| in13_327 | GAGGTAACCAACCAAACAAAA | 134. | 21 | + | chr1:216245296-216245317 |
| in13_328 | GTGTAAGATCAAAGAGACAAGA | 135. | 22 | − | chr1:216245695-216245717 |
| in13_329 | GGTCCTTCTCCTTAGGTTTTA | 136. | 22 | + | chr1:216245571-216245593 |
| in13_379 | GTTATAATTTCTAGAGGAAAAT | 137. | 22 | − | chr1:216245331-216245353 |
| in13_384 | GTACGTGACACCCCTGGCCACA | 138. | 22 | + | chr1:216245261-216245283 |
| in13_392 | GTTTTTTAAAAATCAGATCAAC | 139. | 22 | − | chr1:216246276-216246298 |
| in13_463 | GTCCTGTCAGCCAATATTAGCT | 140. | 22 | − | chr1:216245869-216245891 |
| in13_469 | GCCAATATTAGCTCTGAGTTAT | 141. | 22 | − | chr1:216245860-216245882 |
| in13_480 | GATTAACCTGAAGGTAAAAGA | 142. | 22 | + | chr1:216245112-216245134 |

In some embodiments of these methods, any of the intron 12 gRNAs in Table 1 can be used with any of the intron 13 gRNAs in Table 2, though certain combinations may be more suitable for certain applications. It should be noted, notwithstanding the use of "first" and "second" as nomenclature for gRNAs, that any guide in a pair, in intron 12 or intron 13, can be placed in either one of the gRNA coding sequence positions illustrated in FIG. 9.

In some embodiments, one of the combinations of gRNAs in the following table is used; each row shows a preferred combination (e.g., In12_307 with In12_318).

| Intron 12 gRNA | Intron 13 gRNA |
|---|---|
| In12_307 | In13_318 |
| In12_307 | In13_322 |
| In12_307 | In13_323 |
| In12_307 | In13_327 |
| In12_307 | In13_328 |
| In12_321 | In13_318 |
| In12_321 | In13_322 |
| In12_321 | In13_323 |
| In12_321 | In13_327 |
| In12_321 | In13_328 |

In any of the methods described herein, the engineered CRISPR from Prevotella and Francisella 1 (Cpf1, also known as Cas12a) nuclease can also be used, e.g., as described in Zetsche et al., Cell 163, 759-771 (2015); Schunder et al., Int J Med Microbiol 303, 51-60 (2013); Makarova et al., Nat Rev Microbiol 13, 722-736 (2015); Fagerlund et al., Genome Biol 16, 251 (2015). Unlike SpCas9, Cpf1/Cas12a requires only a single 42-nt crRNA, which has 23 nt at its 3' end that are complementary to the protospacer of the target DNA sequence (Zetsche et al., 2015). Furthermore, whereas SpCas9 recognizes an NGG PAM sequence that is 3' of the protospacer, AsCpf1 and LbCpf1 recognize TTTN PAMs that are found 5' of the protospacer (Id.). In some embodiments, the Cas12a is, e.g., Acidaminococcus sp. BV3L6 Cpf1 (AsCpf1, UniProt U2UMQ6.1) or Lachnospiraceae bacterium ND2006 (LbCpf1, UniProt A0A182DWE3.1), with corresponding gRNAs.

Method Two: Single gRNA Deletion of Exon 13 Splice Acceptor

The second approach makes use of a single gRNA for destruction of the exon 13 splice acceptor. Non-homologous end joining (NHEJ)-mediated indels destroy the splice acceptor, thus preventing exon 13 from being spliced into mRNA.

Preferably, this method uses Staphylococcus aureus wild type or KKH variant SaCas9 (See Kleinstiver et al., Nat Biotechnol. 2015 December; 33 (12): 1293-1298; WO 2016/141224) or Cas12a and corresponding gRNAs. Table 3 provides exemplary target sites in the splice acceptor.

TABLE 3

Guide RNAs for approach 2:

| gRNA Name | Target Site | SEQ ID NO: | Enzyme | Length |
|---|---|---|---|---|
| SA_1 | TATTTTATCTTTAGGGCTTAGG | 143. | SaCas9-KKH | 22 |
| SA_2 | AAATATATTTTATCTTTAGGGC | 144. | SaCas9-KKH | 22 |
| SA_3 | TAAATATATTTTATCTTTAGGG | 145. | SaCas9-KKH | 22 |
| SA_4 | CCTTTTAAATATATTTTATCTT | 146. | SaCas9-KKH | 22 |
| SA_5 | ACCTTTTAAATATATTTTATCT | 147. | SaCas9-KKH | 22 |
| SA_6 | CACCTTTTAAATATATTTTATC | 148. | SaCas9-KKH | 22 |
| SA_7 | GATCACACCTAAGCCCTAAAGA | 149. | SaCas9-KKH | 22 |
| SA_8 | TGATCACACCTAAGCCCTAAAG | 150. | SaCas9-KKH | 22 |
| SA_9 | ATGATCACACCTAAGCCCTAAA | 151. | SaCas9-KKH | 22 |
| SA_10 | GCAATGATCACACCTAAGCCCT | 152. | SaCas9-KKH | 22 |
| SA_11 | TGCAATGATCACACCTAAGCCC | 153. | SaCas9-KKH | 22 |
| SA_12 | TTGCAATGATCACACCTAAGCC | 154. | SaCas9-KKH | 22 |
| SA_13 | ATTGCAATGATCACACCTAAGC | 155. | SaCas9-KKH | 22 |
| SA_14 | CCTTTTAAATATATTTTATCTT | 156. | SaCas9 | 22 |
| SA_18 | ATTTTATCTTTAGGGCTTAGG | 157. | SaCas9-KKH | 21 |
| SA_19 | AATATATTTTATCTTTAGGGC | 158. | SaCas9-KKH | 21 |
| SA_20 | AAATATATTTTATCTTTAGGG | 159. | SaCas9-KKH | 21 |
| SA_21 | CTTTTAAATATATTTTATCTT | 160. | SaCas9-KKH | 21 |
| SA_22 | CCTTTTAAATATATTTTATCT | 161. | SaCas9-KKH | 21 |
| SA_23 | ACCTTTTAAATATATTTTATC | 162. | SaCas9-KKH | 21 |
| SA_24 | ATCACACCTAAGCCCTAAAGA | 163. | SaCas9-KKH | 21 |
| SA_25 | GATCACACCTAAGCCCTAAAG | 164. | SaCas9-KKH | 21 |
| SA_26 | TGATCACACCTAAGCCCTAAA | 165. | SaCas9-KKH | 21 |
| SA_27 | CAATGATCACACCTAAGCCCT | 166. | SaCas9-KKH | 21 |
| SA_28 | GCAATGATCACACCTAAGCCC | 167. | SaCas9-KKH | 21 |
| SA_29 | TGCAATGATCACACCTAAGCC | 168. | SaCas9-KKH | 21 |
| SA_30 | TTGCAATGATCACACCTAAGC | 169. | SaCas9-KKH | 21 |
| SA_31 | CTTTTAAATATATTTTATCTT | 170. | SaCas9 | 21 |
| SA_32 | TTTTATCTTTAGGGCTTAGG | 171. | SaCas9-KKH | 20 |
| SA_33 | ATATATTTTATCTTTAGGGC | 172. | SaCas9-KKH | 20 |
| SA_34 | AATATATTTTATCTTTAGGG | 173. | SaCas9-KKH | 20 |
| SA_35 | TTTTAAATATATTTTATCTT | 174. | SaCas9-KKH | 20 |
| SA_36 | CTTTTAAATATATTTTATCT | 175. | SaCas9-KKH | 20 |
| SA_37 | CCTTTTAAATATATTTTATC | 176. | SaCas9-KKH | 20 |
| SA_38 | TCACACCTAAGCCCTAAAGA | 177. | SaCas9-KKH | 20 |
| SA_39 | ATCACACCTAAGCCCTAAAG | 178. | SaCas9-KKH | 20 |
| SA_40 | GATCACACCTAAGCCCTAAA | 179. | SaCas9-KKH | 20 |
| SA_41 | AATGATCACACCTAAGCCCT | 180. | SaCas9-KKH | 20 |

TABLE 3-continued

Guide RNAs for approach 2:

| gRNA Name | Target Site | SEQ ID NO: | Enzyme | Length |
|---|---|---|---|---|
| SA_42 | CAATGATCACACCTAAGCCC | 181. | SaCas9-KKH | 20 |
| SA_43 | GCAATGATCACACCTAAGCC | 182. | SaCas9-KKH | 20 |
| SA_44 | TGCAATGATCACACCTAAGC | 183. | SaCas9-KKH | 20 |
| SA_45 | TTTTAAATATATTTTATCTT | 184. | SaCas9 | 20 |
| SA_46 | TTTTATCTTTAGGGCTTAGG | 185. | AsCpf1 RVR | 20 |
| SA_47 | AATATATTTTATCTTTAGGG | 186. | LbCpf1 | 20 |
| SA_48 | AAATTGCAATGATCACACCT | 187. | AsCpf1 | 20 |

AAV Delivery Systems

The methods include delivery of a CRISPR/Cas9 genome editing system, including a Cas9 nuclease and one or two guide RNAs, to a subject in need thereof. The delivery methods can include, e.g., viral delivery, e.g., preferably using an adeno-associated virus (AAV) vector that comprises sequences encoding the Cas9 and guide RNA(s). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro and Immunol. 158:97-129 (1992)). AAV vectors efficiently transduce various cell types and can produce long-term expression of transgenes in vivo. AAV vectors have been extensively used for gene augmentation or replacement and have shown therapeutic efficacy in a range of animal models as well as in the clinic; see, e.g., Mingozzi and High, Nature Reviews Genetics 12, 341-355 (2011); Deyle and Russell, Curr Opin Mol Ther. 2009 August; 11 (4): 442-447; Asokan et al., Mol Ther. 2012 April; 20 (4): 699-708. AAV vectors containing as little as 300 base pairs of AAV can be packaged and can produce recombinant protein expression. For example, AAV2, AAV5, AAV2/5, AAV2/8 and AAV2/7 vectors have been used to introduce DNA into photoreceptor cells (see, e.g., Pang et al., Vision Research 2008, 48 (3): 377-385; Khani et al., Invest Ophthalmol Vis Sci. 2007 September; 48 (9): 3954-61; Allocca et al., J. Virol. 2007 81 (20): 11372-11380). In some embodiments, the AAV vector can include (or include a sequence encoding) an AAV capsid polypeptide described in PCT/US2014/060163; for example, a virus particle comprising an AAV capsid polypeptide having an amino acid sequence selected from the group consisting of SEQ ID NOs: 1, 3, 5, 7, 9, 11, 13, 15, and 17 of PCT/US2014/060163, and a Cas9 sequence and guide RNA sequence as described herein. In some embodiments, the AAV capsid polypeptide is an Anc80 polypeptide, e.g., Anc80L27; Anc80L59; Anc80L60; Anc80L62; Anc80L65; Anc80L33; Anc80L36; or Anc80L44. In some embodiments, the AAV incorporates inverted terminal repeats (ITRs) derived from the AAV2 serotype. Exemplary left and right ITRs are presented in Table 6 of WO 2018/026976. It should be noted, however, that numerous modified versions of the AAV2 ITRs are used in the field, and the ITR sequences shown below are exemplary and are not intended to be limiting. Modifications of these sequences are known in the art, or will be evident to skilled artisans, and are thus included in the scope of this disclosure.

Cas9 expression is driven by a promoter known in the art. In some embodiments, expression is driven by one of three promoters: cytomegalovirus (CMV), elongation factor-1 (EFS), or human g-protein receptor coupled kinase-1 (hGRK1), which is specifically expressed in retinal photoreceptor cells. Nucleotide sequences for each of these promoters are provided in Table 5 of WO 2018/026976. Modifications of these sequences may be possible or desirable in certain applications, and such modifications are within the scope of this disclosure.

Expression of the gRNAs in the AAV vector is driven by a promoter known in the art. In some embodiments, a polymerase III promoter, such as a human U6 promoter. An exemplary U6 promoter sequence is presented below:

(SEQ ID NO: 188)
AAGGTCGGGCAGGAAGAGGGCCTATTTCCCATGATTCCTTCATATTTGCA

TATACGATACAAGGCTGTTAGAGAGATAATTAGAATTAATTTGACTGTAA

ACACAAAGATATTAGTACAAAATACGTGACGTAGAAAGTAATAATTTCTT

GGGTAGTTTGCAGTTTTAAAATTATGTTTTAAAATGGACTATCATATGCT

TACCGTAACTTGAAAGTATTTCGATTTCTTGGCTTTATATATCTTGTGGA

AAGGACGAAACACC.

In some embodiments, the nucleic acid or AAV vector shares at least 80%, 85%, 90%, 95%, 96%, 97%, 98%, 99% or greater sequence identity with one of the nucleic acids or AAV vectors recited above The AAV genomes described above can be packaged into AAV capsids (for example, AAV5 capsids), which capsids can be included in compositions (such as pharmaceutical compositions) and/or administered to subjects. An exemplary pharmaceutical composition comprising an AAV capsid according to this disclosure can include a pharmaceutically acceptable carrier such as balanced saline solution (BSS) and one or more surfactants (e.g., TWEEN® 20) and/or a thermosensitive or reverse-thermosensitive polymer (e.g., pluronic). Other pharmaceutical formulation elements known in the art may also be suitable for use in the compositions described here.

Compositions comprising AAV vectors according to this disclosure can be administered to subjects by any suitable means, including without limitation injection, for example, subretinal injection or injection through the round window. The concentration of AAV vector within the composition is selected to ensure, among other things, that a sufficient AAV dose is administered to the retina or inner ear of the subject, taking account of dead volume within the injection apparatus and the relatively limited volume that can be safely administered. Suitable doses may include, for example, $1\times10^{11}$ viral genomes (vg)/mL, $2\times10^{11}$ viral genomes (vg)/mL, $3\times10^{11}$ viral genomes (vg)/mL, $4\times10^{11}$ viral genomes (vg)/mL, $5\times10^{11}$ viral genomes (vg)/mL, $6\times10^{11}$ viral genomes (vg)/mL, $7\times10^{11}$ viral genomes (vg)/mL, $8\times10^{11}$ viral genomes (vg)/mL, $9\times10^{11}$ viral genomes (vg)/mL, $1\times10^{12}$ vg/mL, $2\times10^{12}$ viral genomes (vg)/mL, $3\times10^{12}$ viral genomes (vg)/mL, $4\times10^{12}$ viral genomes (vg)/mL, $5\times10^{12}$ viral genomes (vg)/mL, $6\times10^{12}$ viral genomes (vg)/mL, $7\times10^{12}$ viral genomes (vg)/mL, $8\times10^{12}$ viral genomes (vg)/mL, $9\times10^{12}$ viral genomes (vg)/mL, $1\times10^{13}$ vg/mL, $2\times10^{13}$ viral genomes (vg)/mL, $3\times10^{13}$ viral genomes (vg)/mL, $4\times10^{13}$ viral genomes (vg)/mL, $5\times10^{13}$ viral genomes (vg)/mL, $6\times10^{13}$ viral genomes (vg)/mL, $7\times10^{13}$ viral genomes (vg)/mL, $8\times10^{13}$ viral genomes (vg)/mL, or $9\times10^{13}$ viral genomes (vg)/mL. Any suitable volume of the composition may be delivered to the subretinal or cochlear space. In some instances, the volume is selected to form a bleb in the subretinal space, for example 1 microliter, 10 microliters, 50 microliters, 100 microliters, 150 microliters, 200 microliters, 250 microliters, 300 microliters, etc.

Any region of the retina may be targeted, though the fovea (which extends approximately 1 degree out from the center of the eye) may be preferred in certain instances due to its role in central visual acuity and the relatively high concentration of cone photoreceptors there relative to peripheral regions of the retina. Alternatively or additionally, injections may be targeted to parafoveal regions (extending between approximately 2 and 10 degrees off center), which are characterized by the presence of all three types of retinal photoreceptor cells. In addition, injections into the parafoveal region may be made at comparatively acute angles using needle paths that cross the midline of the retina. For instance, injection paths may extend from the nasal aspect of the sclera near the limbus through the vitreal chamber and into the parafoveal retina on the temporal side, from the temporal aspect of the sclera to the parafoveal retina on the nasal side, from a portion of the sclera located superior to the cornea to an inferior parafoveal position, and/or from an inferior portion of the sclera to a superior parafoveal position. The use of relatively small angles of injection relative to the retinal surface may advantageously reduce or limit the potential for spillover of vector from the bleb into the vitreous body and, consequently, reduce the loss of the vector during delivery. In other cases, the macula (inclusive of the fovea) can be targeted, and in other cases, additional retinal regions can be targeted, or can receive spillover doses.

For delivery to the inner ear, injection to the cochlear duct, which is filled with high potassium endolymph fluid, could provide direct access to hair cells. However, alterations to this delicate fluid environment may disrupt the endocochlear potential, heightening the risk for injection-related toxicity. The perilymph-filled spaces surrounding the cochlear duct, scala tympani and scala vestibuli, can be accessed from the middle ear, either through the oval or round window membrane (RWM). The RWM, which is the only non-bony opening into the inner ear, is relatively easily accessible in many animal models and administration of viral vector using this route is well tolerated. Administration through the oval window or across the tympanic membrane can also be used. See, e.g., WO2017100791 and U.S. Pat. No. 7,206,639.

For pre-clinical development purposes, systems, compositions, nucleotides and vectors according to this disclosure can be evaluated ex vivo using a retinal explant system, or in vivo using an animal model such as a mouse, rabbit, pig, nonhuman primate, etc. Retinal explants are optionally maintained on a support matrix, and AAV vectors can be delivered by injection into the space between the photoreceptor layer and the support matrix, to mimic subretinal injection. Tissue for retinal explanation can be obtained from human or animal subjects, for example mouse.

Explants are particularly useful for studying the expression of gRNAs and/or Cas9 following viral transduction, and for studying genome editing over comparatively short intervals. These models also permit higher throughput than may be possible in animal models, and can be predictive of expression and genome editing in animal models and subjects. Small (mouse, rat) and large animal models (such as rabbit, pig, nonhuman primate) can be used for pharmacological and/or toxicological studies and for testing the systems, nucleotides, vectors and compositions of this disclosure under conditions and at volumes that approximate those that will be used in clinic. Because model systems are selected to recapitulate relevant aspects of human anatomy and/or physiology, the data obtained in these systems will generally (though not necessarily) be predictive of the behavior of AAV vectors and compositions according to this disclosure in human and animal subjects.

Genetically Modified Animals and Cells Lacking Exon 13

Also provided herein are non-human genetically modified animals comprising a mutation in exon 13 (or the equivalent exon, for example, exon 12 in the mouse) in the USH2A gene. Such animals are useful as models of disease, e.g., of Usher syndrome or arRP, for studying the function and/or activity of USH2A protein and for identifying and/or evaluating potential therapeutic compounds for treating conditions associated with mutations in exon 13 of the USH2A gene. As used herein, a "genetically modified animal" is a non-human animal, preferably a mammal, more preferably a rodent such as a rat or mouse, in which one or more of the cells of the animal includes a modified gene. Other examples of genetically modified animals include non-human primates, sheep, dogs, cows, goats, chickens, amphibians, and the like.

The genetically modified animals can have a complete deletion of exon 13, an inversion of exon 13, or a mutation that disrupts the exon 13 splice acceptor site, integrated into or occurring in the genome of the cells of a genetically modified animal (e.g., in one or both alleles of the gene in the genome). In preferred embodiments, the animal has had both endogenous USH2A alleles replaced with a human USH2A gene, or has had part of both endogenous USH2A alleles containing the relevant exon and flanking intronic regions replaced with a human USH2A exon 13 and flanking intronic regions, with a complete deletion of exon 13, an inversion of exon 13, or a mutation that disrupts the exon 13 splice acceptor site.

Methods for making genetically modified animals are known in the art; see, e.g., WO2016049024; WO201604925; WO2017124086; WO2018009562; and U.S. Pat. No. 9,901,080. Such techniques include, without limitation, pronuclear microinjection (See, e.g., U.S. Pat. No. 4,873,191), retrovirus mediated gene transfer into germ lines (Van der Putten et al., Proc. Natl. Acad. Sci. USA, 82:6148-1652 (1985)), gene targeting into embryonic stem cells (Thompson et al., Cell 56:313-321 (1989)), electroporation of embryos (Lo, Mol. Cell. Biol., 3:1803-1814 (1983)), and in vitro transformation of somatic cells, such as cumulus or mammary cells, followed by nuclear transplantation (Wilmut et al., Nature, 385:810-813 (1997); and Wakayama et al., Nature, 394:369-374 (1998)); these methods can be modified to use CRISPR as described herein. For example, fetal fibroblasts can be genetically modified using CRISPR as described herein, and then fused with enucleated oocytes. After activation of the oocytes, the eggs are cultured to the blastocyst stage. See, for example, Cibelli et al., Science, 280:1256-1258 (1998)

A founder animal can be identified based upon the presence of a mutation in exon 13 of USH2A in its genome and/or expression of USH2A mRNA lacking exon 13 in tissues or cells of the animals. A genetically modified founder animal can then be used to breed additional animals carrying the modified gene. Moreover, animals carrying a modified encoding an Ush2A protein lacking exon 13 can further be bred to Ush2a knockout animals.

The invention also includes a population of cells isolated from an animal as described herein, as well as primary or cultured cells, e.g., isolated cells, engineered to include a mutation in exon 13 of human USH2A gene or a deletion of exon 12 in the mouse Ush2a gene. The cells can have a complete deletion of exon13, an inversion of exon 13, or a mutation that disrupts the exon 13 splice acceptor site, integrated into or occurs in the genome of the cells. The cells can be from any mammal, e.g., a human or non-human mammal, or other animal.

Further provided herein are nucleic acids (e.g., isolated nucleic acids) that comprise or encode an USH2A mRNA that lacks exon 13, e.g., that have a complete deletion of exon13, an inversion of exon 13, or a mutation that disrupts the exon 13 splice acceptor site, as well as expression and delivery vectors (including viral and non-viral vectors) comprising the nucleic acids, and usherin proteins lacking exon 13. Preferably the sequences are generated using a human USH2A sequence, but they can also be generated from other mammals, including mouse (mRNA: NM_021408.3; syntenic exon: 12) rat (mRNA: NM_001302219.1; syntenic exon 13); chimpanzee (mRNA: XM_016938662.1; syntenic exon: 12); Cynomolgus macaque (macaca fasicularis, mRNA: XM_005540847.2 or XM_005540848.1) and african green monkey (chlorocebus sabeus, mRNA: XM_007988447.1).

EXAMPLES

The invention is further described in the following examples, which do not limit the scope of the invention described in the claims.

Example 1. USH2A In Vitro Model

This Examiner describes the generation of an USH2A knockout cell line.
1. Characterization of OC-k1 Cells.

Figure 1C:
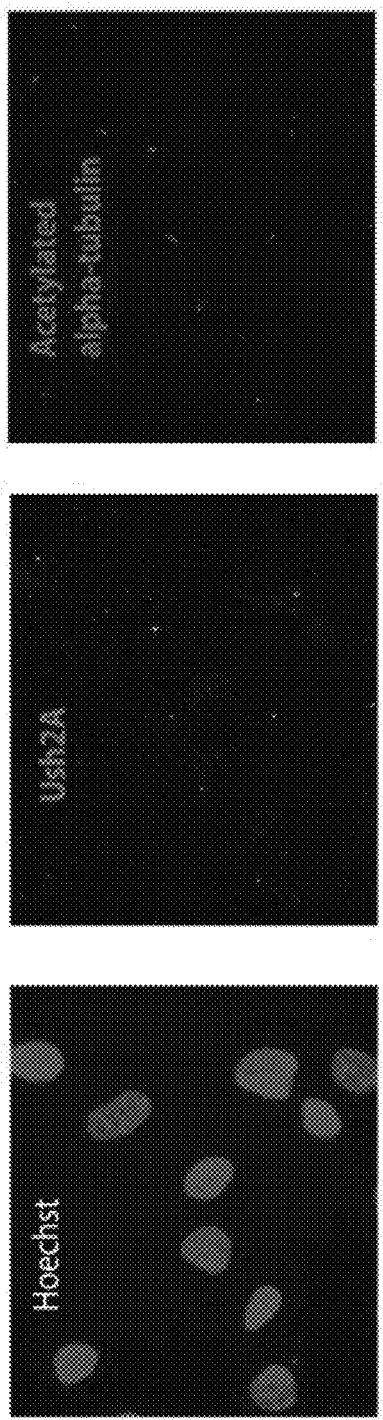
Figure 1D:
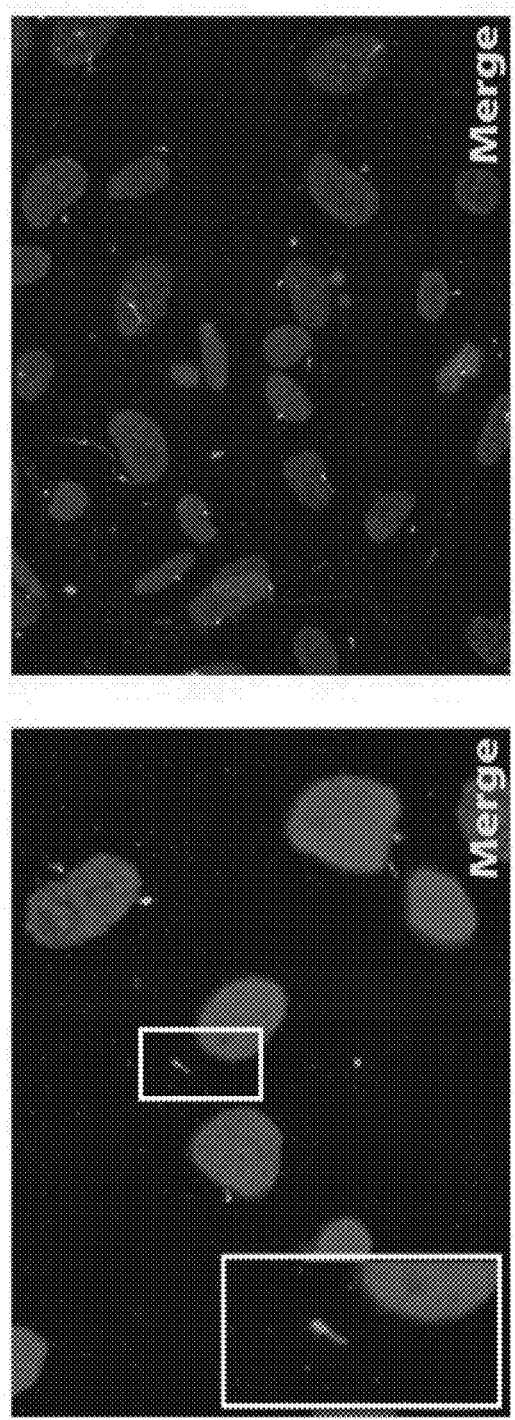
Figures 2A, 2B:
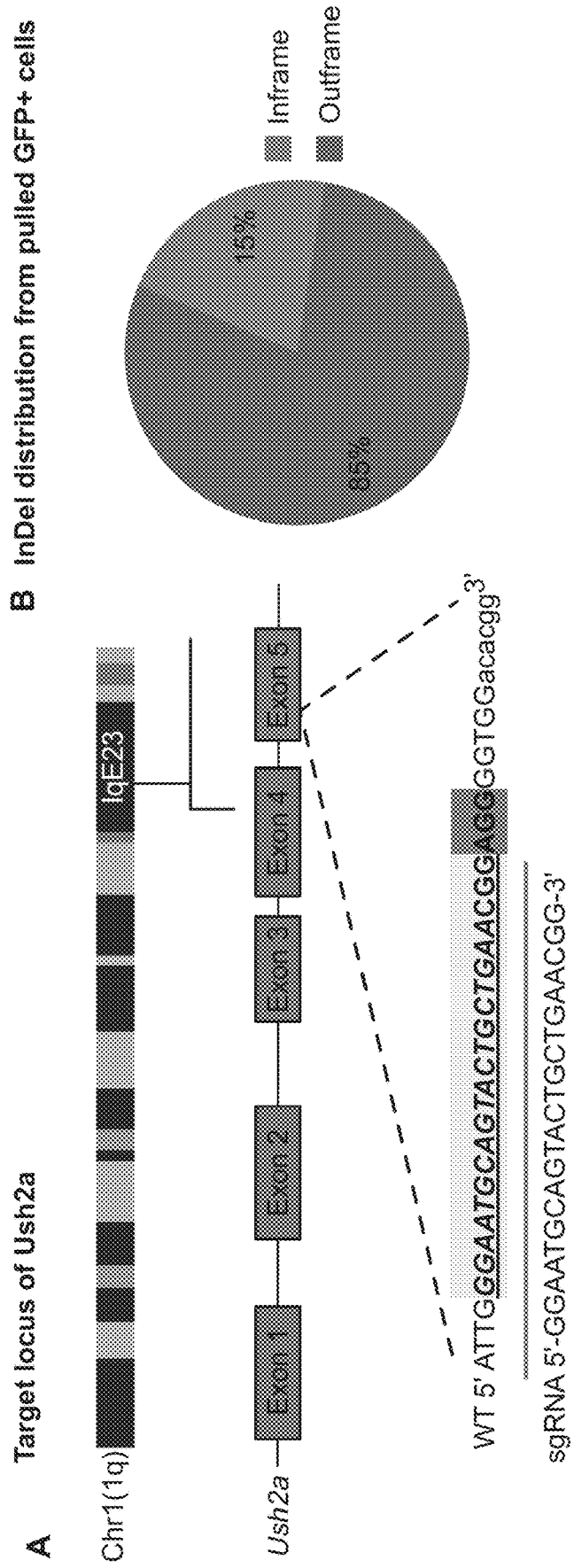
Figure 2C:
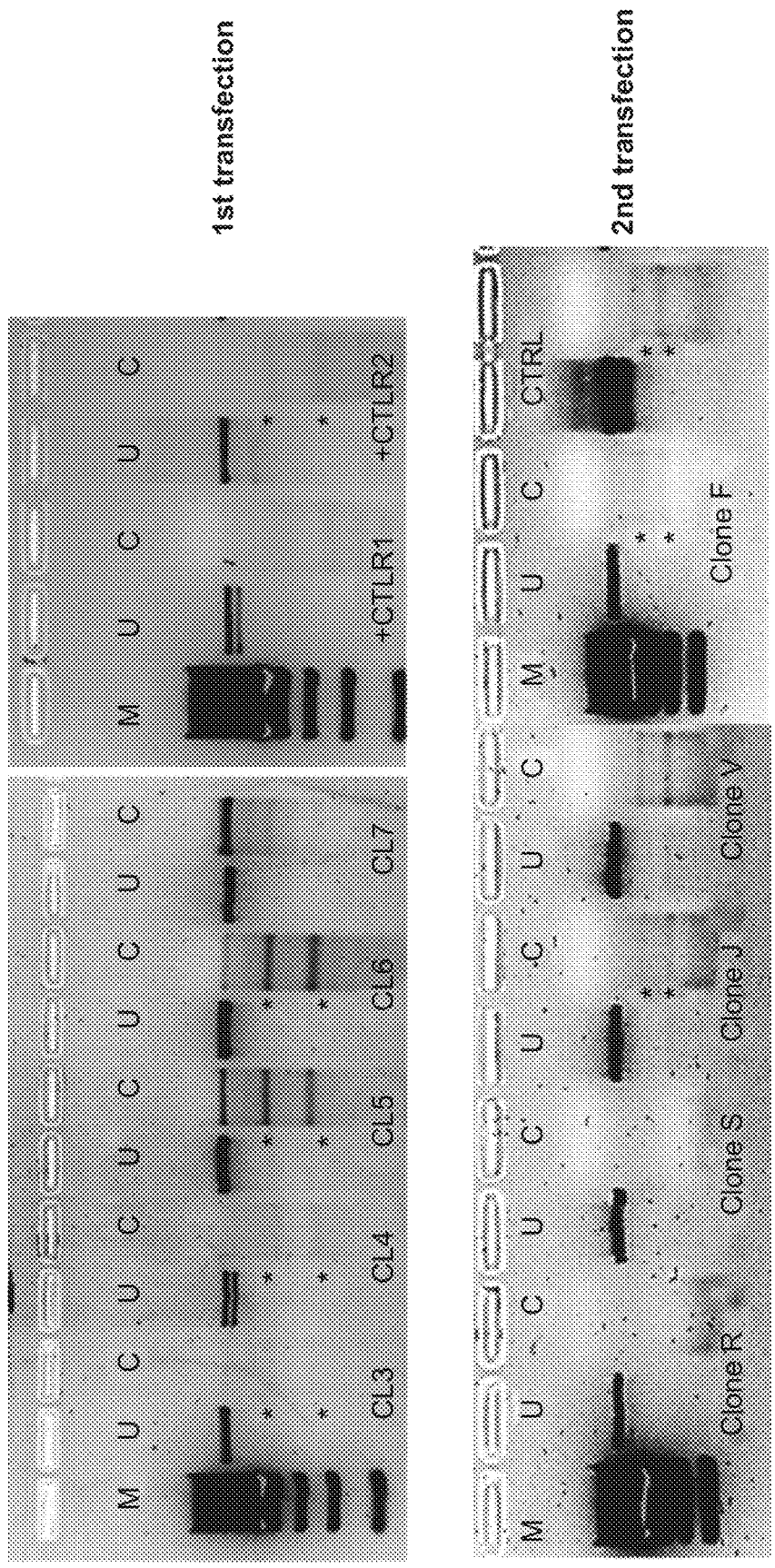
Figure 3A:
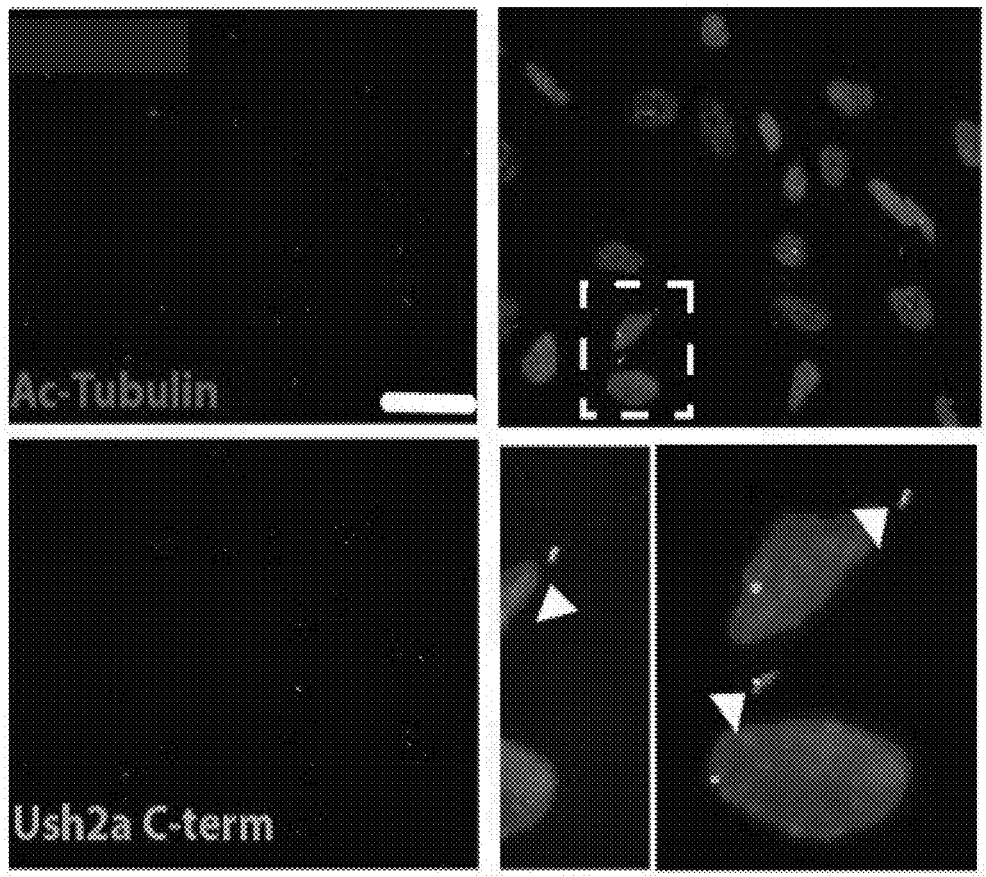
FIGS. 3A-3D: Ciliogenesis in wild-type and Ush2a null OC-K1 cell lines. Immunostaining for ciliary markers for clone 4 (3A), 17 (3B) and J (3C). Ac-Tub appears in red stains the ciliary axoneme, ush2a appears in green that co-localizes at the base of cilia. The length of cilia in clone 17 and clone J is significantly shorter (3D).
Figure 3B:
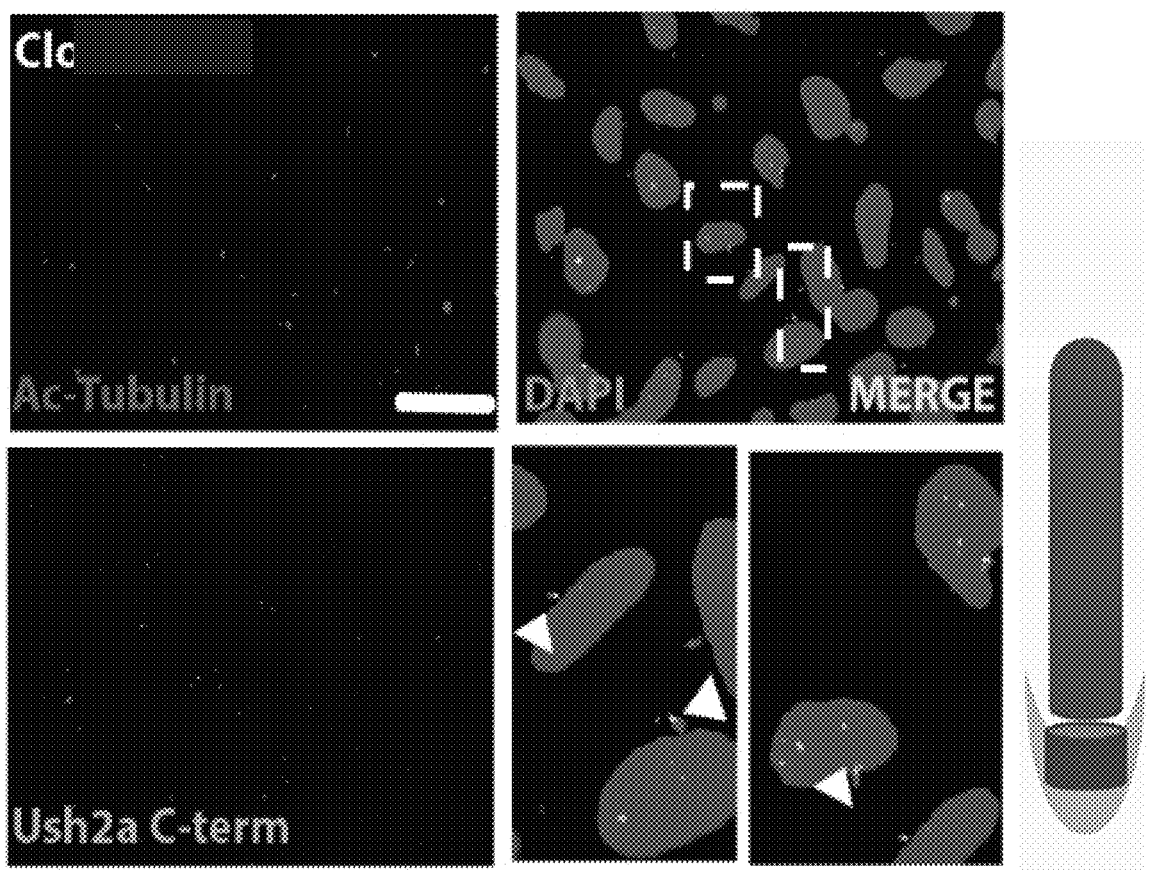
Figure 3C:
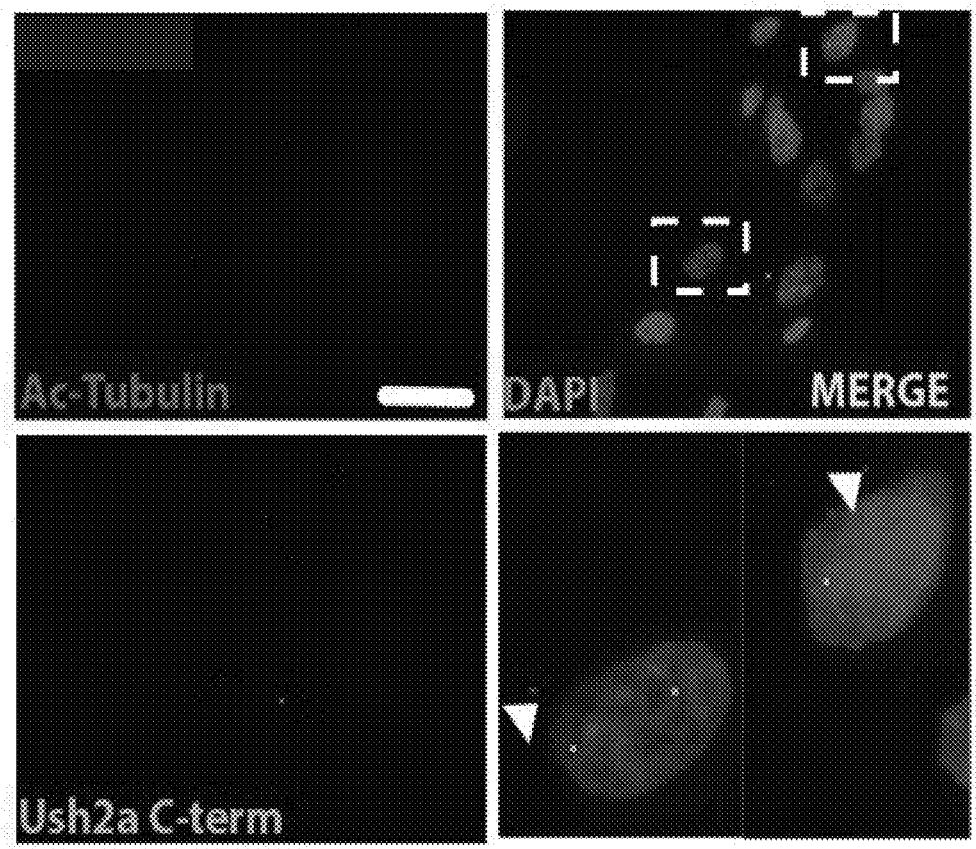
Figure 3D:
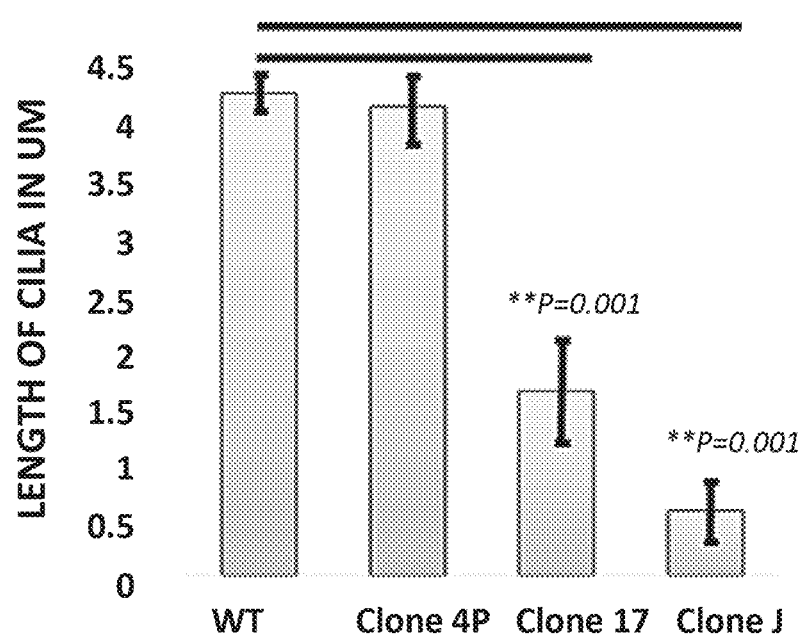
Figures 4A, 4B, 4C, 4D:
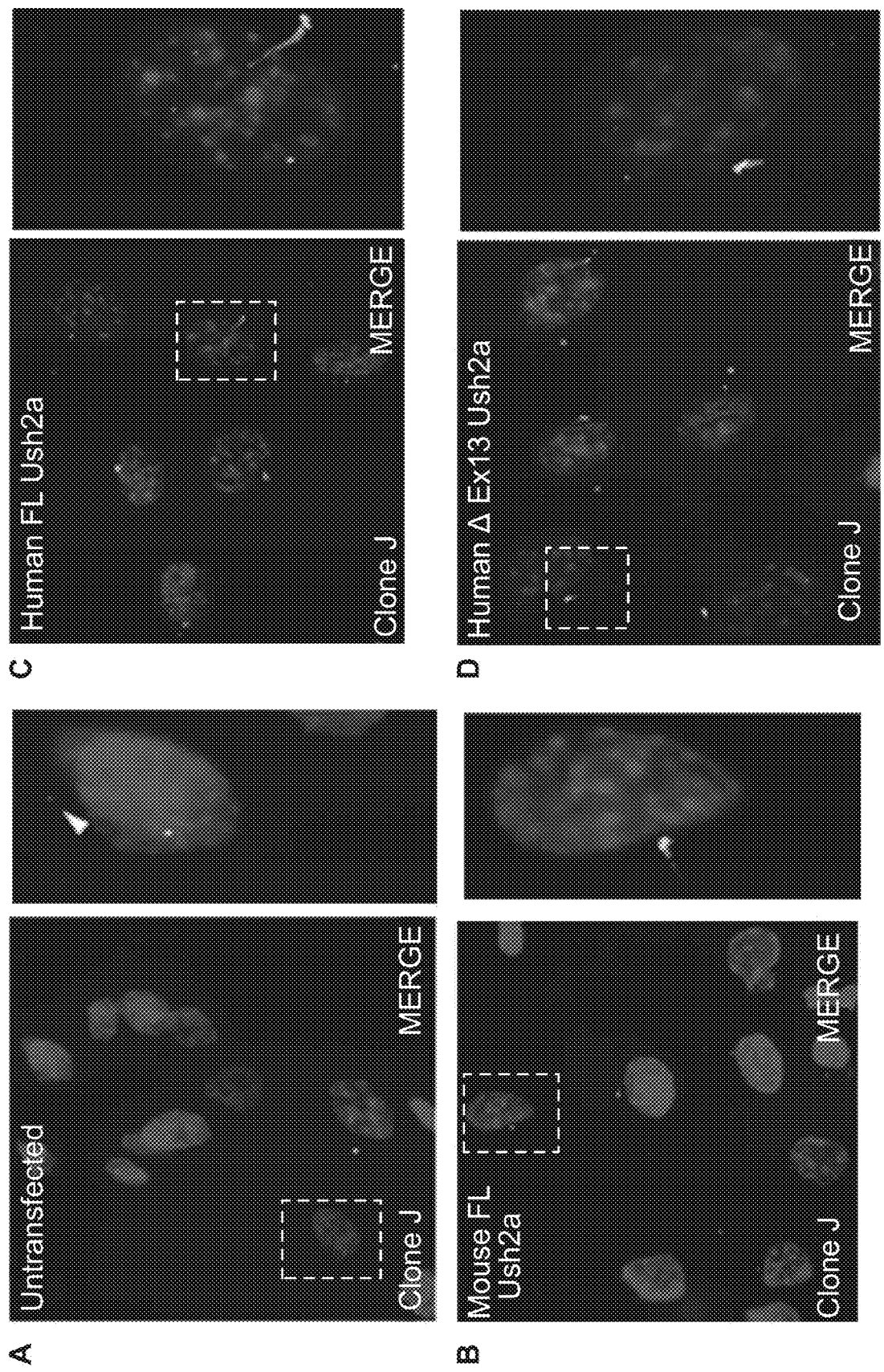
FIGS. 4A-E: Expression of USH2A-ΔEx13 cDNA rescues the ciliogenesis in Ush2a null cells. Ush2a null cells from clone J transfected with mouse full-length Ush2a cDNA (4B), human wild-type full length USH2A cDNA (4C) and human USH2A-ΔEx13 cDNAs (4D). Non-transfected cell used as control (4A). Cilia were labeled with Ac-tubulin and the expression of Ush2a is detected by C-term anti-Ush2a antibody in green. 4E. The cilia length was significantly increased in cells transfected with wild-type and human USH2A-ΔEx13 cDNAs as compared to the knockout.
Figure 4E:
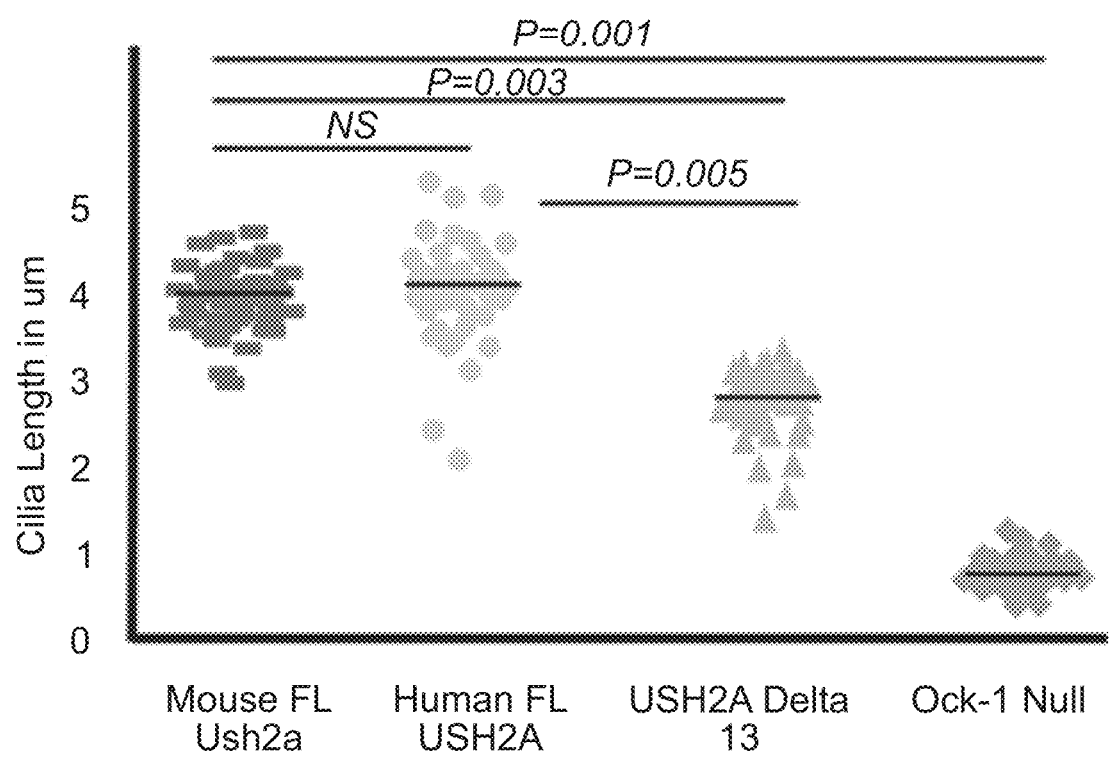

OC-k1 cells were selected as a model system for this study. OC-k1 cells are derived from mouse cochlea (Kalinec et al. (1999) Cell biology international 23 (3): 175-184; Kelley et al. (1993) Development 119 (4): 1041-1053). These are tri allelic, expressing Ush2a protein and its interacting proteins such as Whrn, Vlgr1 in the Usher 2 complex (FIGS. 1A, 1B), making these cells particularly appropriate for these studies. The preliminary results illustrated that the OC-k1 wild type cells stably expressed the Ush2a protein at the base of primary cilia. (FIGS. 1C, 1D).
2. Generation of Ush2A Knockout Cell Line in OC-k1 Cells CRISPR/Cas9 technology was used to create the Ush2a null cell model in OC-k1 cells. Guide RNA 5'-GGAATGCAGTACTGCTGAACGG-3' (SEQ ID NO:3) for wild-type SpCas9 was designed to target the exon 5 of mouse Ush2a gene (FIG. 2A). U6-sgRNA and CAG-Sp-Cas9-P2A-GFP plasmids were CO-transfected into OC-k1 cells using lipofectamine 3000. Two days post-transfection, the GFP positive cells were collected by sorting, plated at low density, and grown to mature colonies. Post genomic DNA isolation from these cells, the region spanning the sgRNA target site was PCR amplified and deep sequencing analysis was performed to get insights into the frequency of NHEJ-induced insertion-deletions (Indels) in Ush2a alleles. A cleavage efficiency of ~69% was observed with a wide variety of indels with 85% of out-of-frame indels (FIG. 2B). A total of 328 clones were screened with T7E1 assay (FIG. 2C) and found that the clone 4 obtained from first attempt of transfections resulted in a mixed pattern of indels including in-frame, out-of-frame and uncut alleles (FIG. 2D). In order to knockout all three Ush2a alleles in a single clone, clone 4 was re-transfected with the same SpCas9-sgRNA pair and serial dilution of the culture was performed. Of many different single clones analyzed with both T7E1 and NGS analysis, clone J was confirmed to be completely null for Ush2a (two alleles with 7 bp and remaining one allele with 1 bp out of frame deletions, based on ratios of NGS paired reads) as shown in FIG. 2D. Other clones, for example clone 17, showed in-frame deletion for one allele and out-of-frame deletion for other two alleles.
3. Characterization of Ush2A Knockout Cell Lines Ush2a is expressed at the base of cilia. This experiment investigated whether depletion of Ush2a would affect ciliogenesis. Cells were serum starved and stained for Ush2a and acetylated alpha-tubulin, a ciliary marker. As illustrated in FIG. 3, clone 4 and clone 17 produced cilia as shown by Ace-tubulin staining (FIGS. 3A and 3B). They also expressed Ush2a protein at base of cilium, detected by anti-C-term Ush2a antibody (Zou et al., Hum Mol Genet. 2015 Dec. 15; 24 (24): 6944-57). The null clone J failed to produce any detectable cilia (FIG. 3C). However, a stunted basal body look-like structure was observed in clone J. Cilia length was further measured from the basal body to the tip of cilia using an acetylated tubulin antibody. (FIG. 3D, n=50). Significant shortening of cilia in clone 17 and J, compared to the wild-type cells was observed, indicating that ciliogenesis is hampered in the Ush2a null OC-k1 cells.
4. Expression of USH2A-ΔEx13 cDNA Rescued the Ciliogenesis in Ush2a Null Cells In order to determine whether the Ush2a protein that lacks portion of the reparative Laminin EGF like domain (encoded by exon 13) will retain partial or complete biologic function of USH2A protein, full-length and USH2A-ΔEx13 cDNAs were transfected into the Ush2a null line and their effect on ciliogenesis was evaluated. It was observed that both the mouse and human wild-type full length USH2A cDNAs were able to rescue ciliogenesis (FIGS. 4B and 4C). In addition, the expression of human USH2A-ΔEx13 was able to increase the length of cilia to 63% of the wild-type cilia (FIGS. 4D and 4E). These results indicate that the product of the aberrant USH2A-ΔEx13 retains at least partial biological function of USH2A.

Example 2. Targeted Ush2a-ΔEx12 Mouse Model

Figures 5A, 5B:
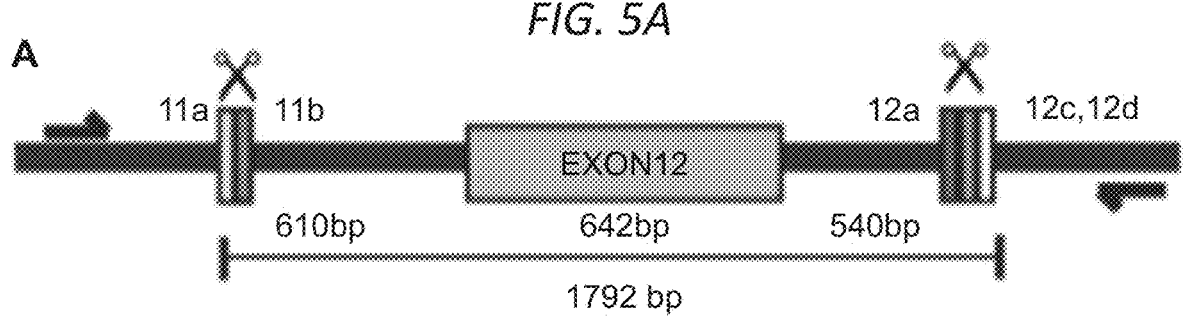
FIGS. 5A-D: Generation of Ush2a-ΔEx12 mouse lines using CRISPR/Cas9. 5A. Schematic illustration of approach for knocking out exon 12 in mouse Ush2a gene. 5B. sgRNA sequences to target intron 11 (11A (SEQ ID NO:12), 11B (SEQ ID NO:13) and 11C (SEQ ID NO:14)) and intron 12 (12A (SEQ ID NO: 15), 12C (SEQ ID NO:16) and 12D (SEQ ID NO:17)). 5C. Cleavage efficiencies of selected sgRNAs on a DNA template derived from Ush2a genomic region surrounding exon 12. 5D. Schematic illustration of deletion of exon12 and surrounding intronic sequence in 9 Ush2a-ΔEx12 found mice.
Figure 5C:
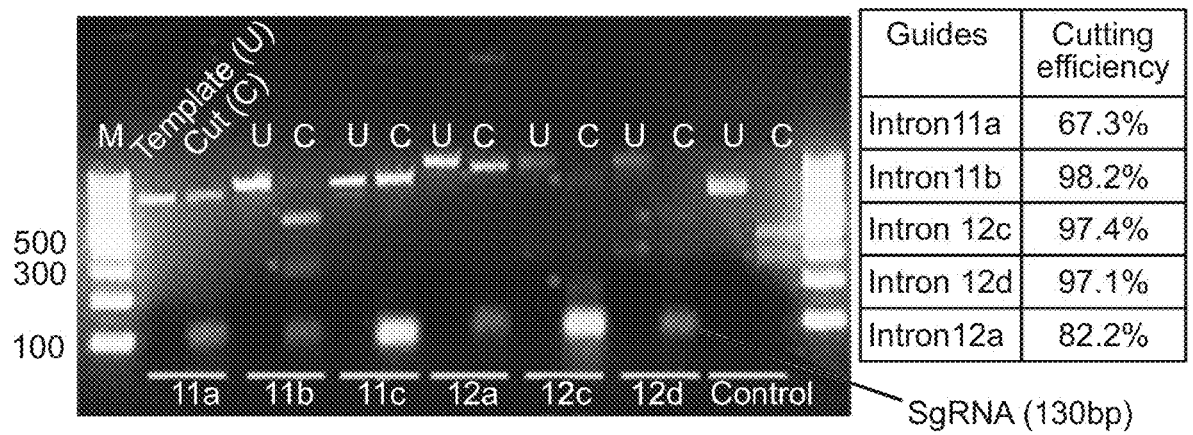
Figure 5D:
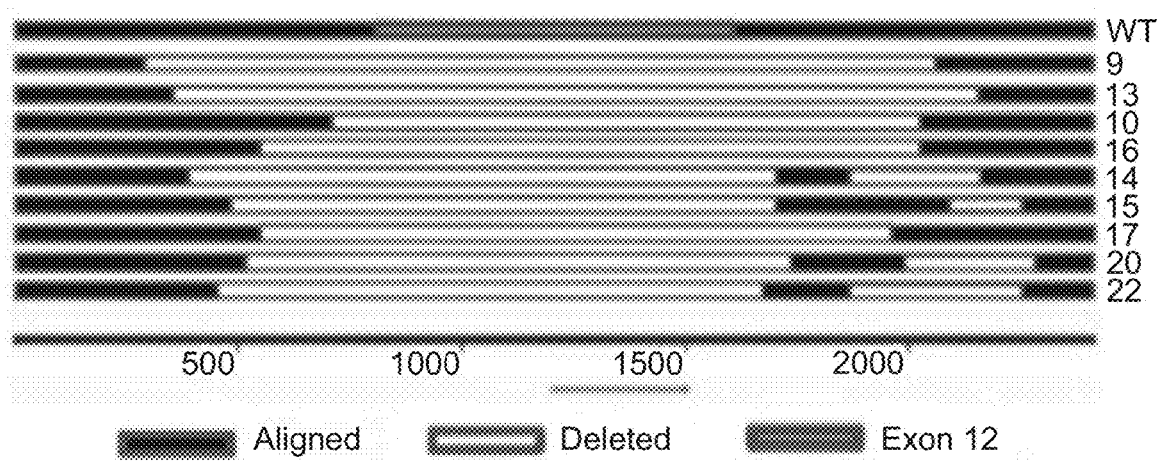

To further assess the cell-based findings in Ush2a null cells in vivo, Ush2a-ΔEx12 mouse lines were generated using CRISPR/Cas9 technology. Pairs of sgRNAs that target the flanking intron 11 (11A, 11B and 11C) and intron 12 (12A, 12C and 12D) (FIG. 5A, 5B) were designed. All guides were synthesized and in vitro transcribed and tested for cleavage efficiency using an in-vitro cleavage assay. FIG. 5C illustrates the selected sgRNAs are active and cleaved PCR template derived from Ush2a genomic region surrounding exon 12 with efficiencies of 67.3% to 98.2%. All three pairs of sgRNAs were microinjected together with SpCas9 protein into the pronuclei of mouse zygotes to generate the Ush2a-ΔEx12 mouse lines in the Genome Modification Facility at Harvard University. A total of 40 pups were obtained from the pronuclear injections. With initial genotyping and sequencing, it was confirmed that 29 mice (71%) carry deletion of exon 12 and flanking introns with different sizes. Sanger sequence verified 9 founders of mice (FIG. 5D). The male founders were further backcrossed with C57BL6/J females and F1 generations were obtained.

Figure 5E:
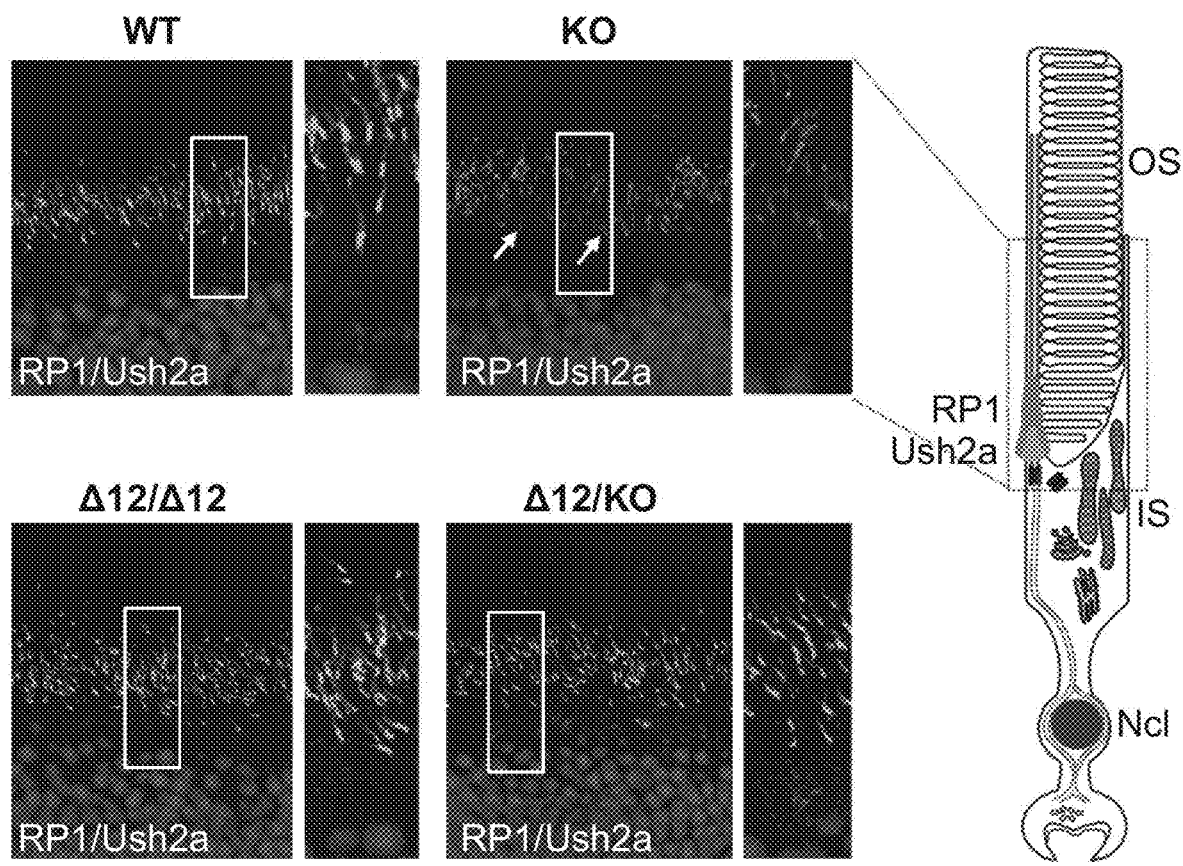
FIGS. 5E-K: Phenotypic rescue by Ush2a-ΔEx12. 5E, both the wild type and exon 12-skippped Ush2a proteins were localized at the transition zone of photoreceptor sensory cilia in ΔEx12/ΔEx12, ΔEx12/ko, and wt mice. 5F, Cochleas isolated from P3 ΔEx12/ΔEx12 and wt mice and stained for phalloidin (top panel), and Ush2a, FM1-43, and phalloidin. 5G, Inner and outer hair cell structures in ΔEx12/ΔEx12, ΔEx12/ko, and wt mice on staining with Ush2a, as compared with the knockout. 5H, Auditory brain stem recordings showing restoration of the ABR response in the Ush2a ko/ko mice by the Ush2a-Ex12 allele as compared to the knockout. 5I, Phalloidin staining showed disrupted bundles in the ko/ko mice, but not in ΔEx12/ΔEx12, ΔEx12/ko, or wt mice. 5J, Arrows indicate the accumulation of GFAP protein in ko retina but not in ΔEx12/ΔEx12, ΔEx12/ko, or wt retina. 5K, Normal cone opsin localization in ΔEx12/ΔEx12 and ΔEx12/ko mice, as compared to ko/ko mice.

The phenotype of the resulting Ush2a-ΔEx12 mouse lines was characterized histologically and functionally. The localization of the Ush2a-ΔEx12 protein and its interaction with other Usher2 complex proteins at two months of age was determined by immunostaining, and showed that both the wild type and exon 12-skipped Ush2a proteins were localized at the transition zone of photoreceptor sensory cilia in ΔEx12/ΔEx12, ΔEx12/ko, and wt mice (FIG. 5E).

The therapeutic potential of Ush2a-ΔEx12 was evaluated by transferring this Ush2a-ΔEx12 allele onto an Ush2a null background in Ush2a$^{-/-}$ knockout mice (Liu, X., et al., Proc Natl Acad Sci USA, 2007. 104 (11): p. 4413-8.) The phenotypes observed in these Ush2a/-mice include progressive disruption of inner hair cells in the cochlea after 4 months of age and diminished inner hair cells at 7 months of age; a detectable accumulation of GFAP and mis-localization of cone opsin at 3 months of age; gradual outer nuclear layer thinning and photoreceptor abnormalities after 10 months of age; 50% loss of photoreceptors and 60% or greater reduction of ERG amplitudes for a- and b-waves by the age of 20 months (Liu, X., et al., Proc Natl Acad Sci USA, 2007. 104 (11): p. 4413-8; Lu, B., et al., Invest Ophthalmol Vis Sci, 2010. 51 (4): p. 2269-76.

Figure 5F:
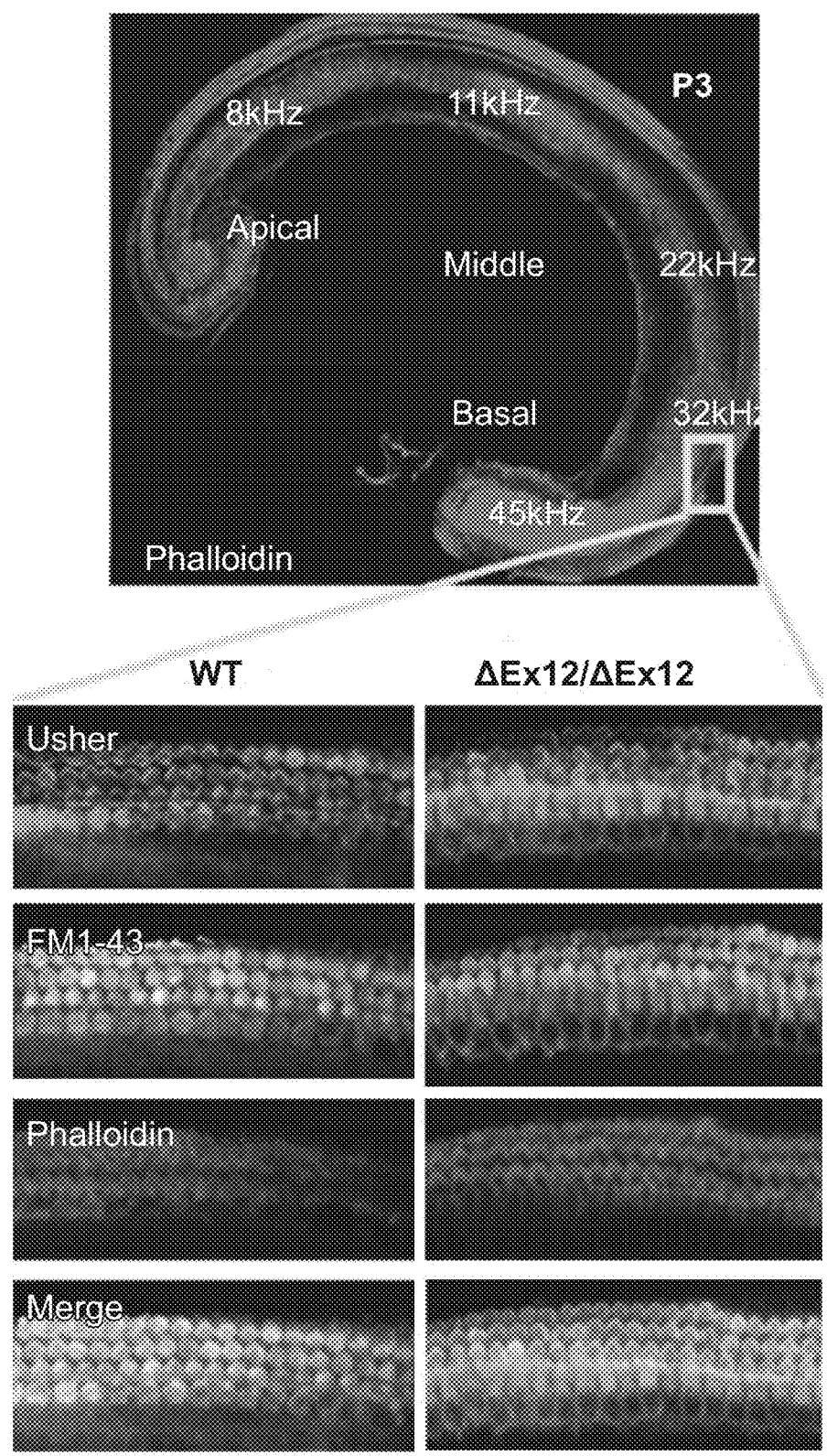
Figure 5G:
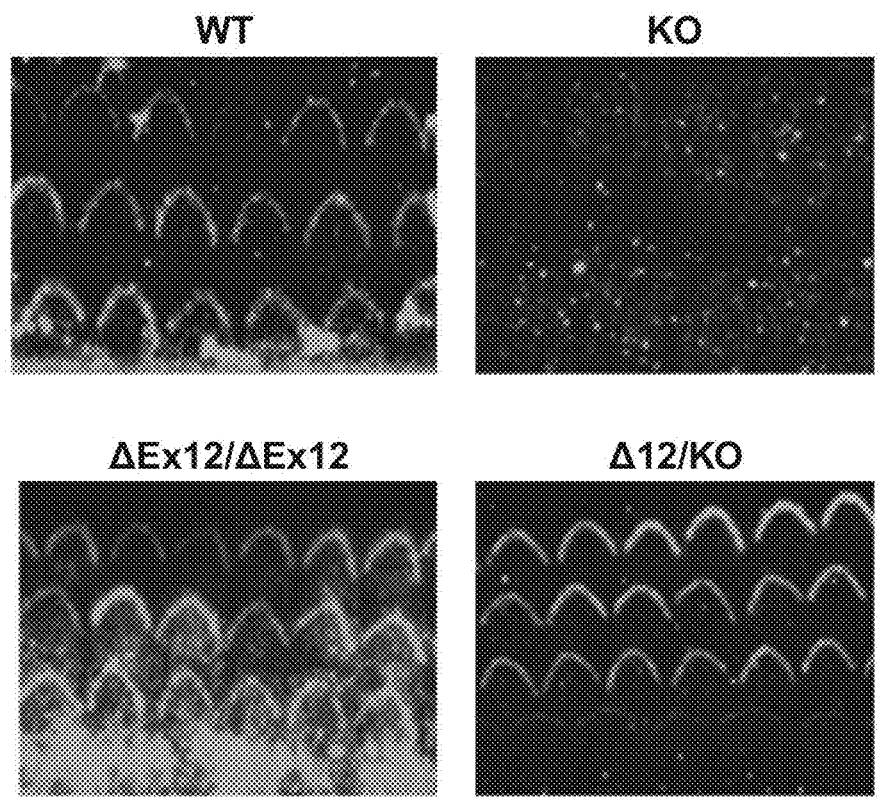
Figure 5H:
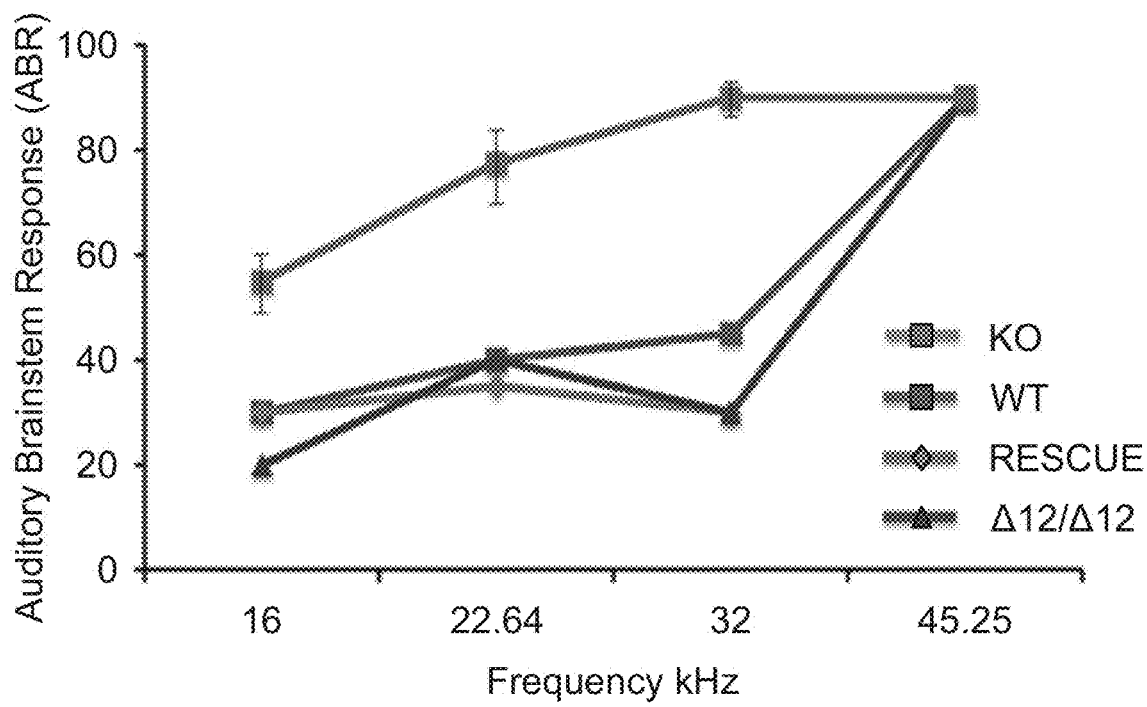
Figure 5I:
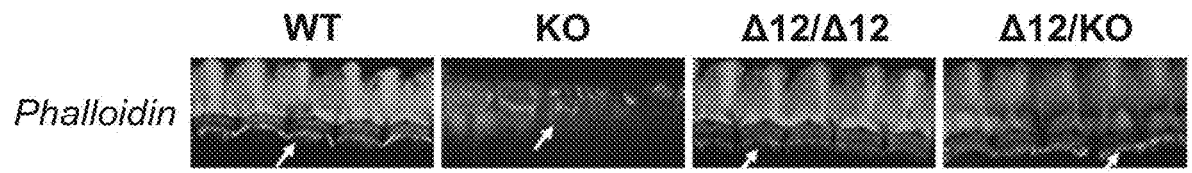

Cochleas were isolated from P3 ΔEx12/ΔEx12 and wt mice and stained for phalloidin (top panel), and Ush2a, FM1-43, and phalloidin (FIG. 5F), showing essentially normal morphology in the ΔEx12/ΔEx12 mice. Inner and outer hair cell structures were grossly normal in ΔEx12/ΔEx12, ΔEx12/ko, and wt mice on staining with Ush2a, as compared with the knockout (FIG. 5G). Auditory brain stem recordings showed improved hearing as determined by ABR in the Ush2a ko/ko mice by the Ush2a-Ex12 allele (FIG. 5H). Phalloidin staining showed disrupted bundles in the ko/ko mice, but not in ΔEx12/ΔEx12, ΔEx12/ko, or wt mice (FIG. 5I).

Figure 5J:
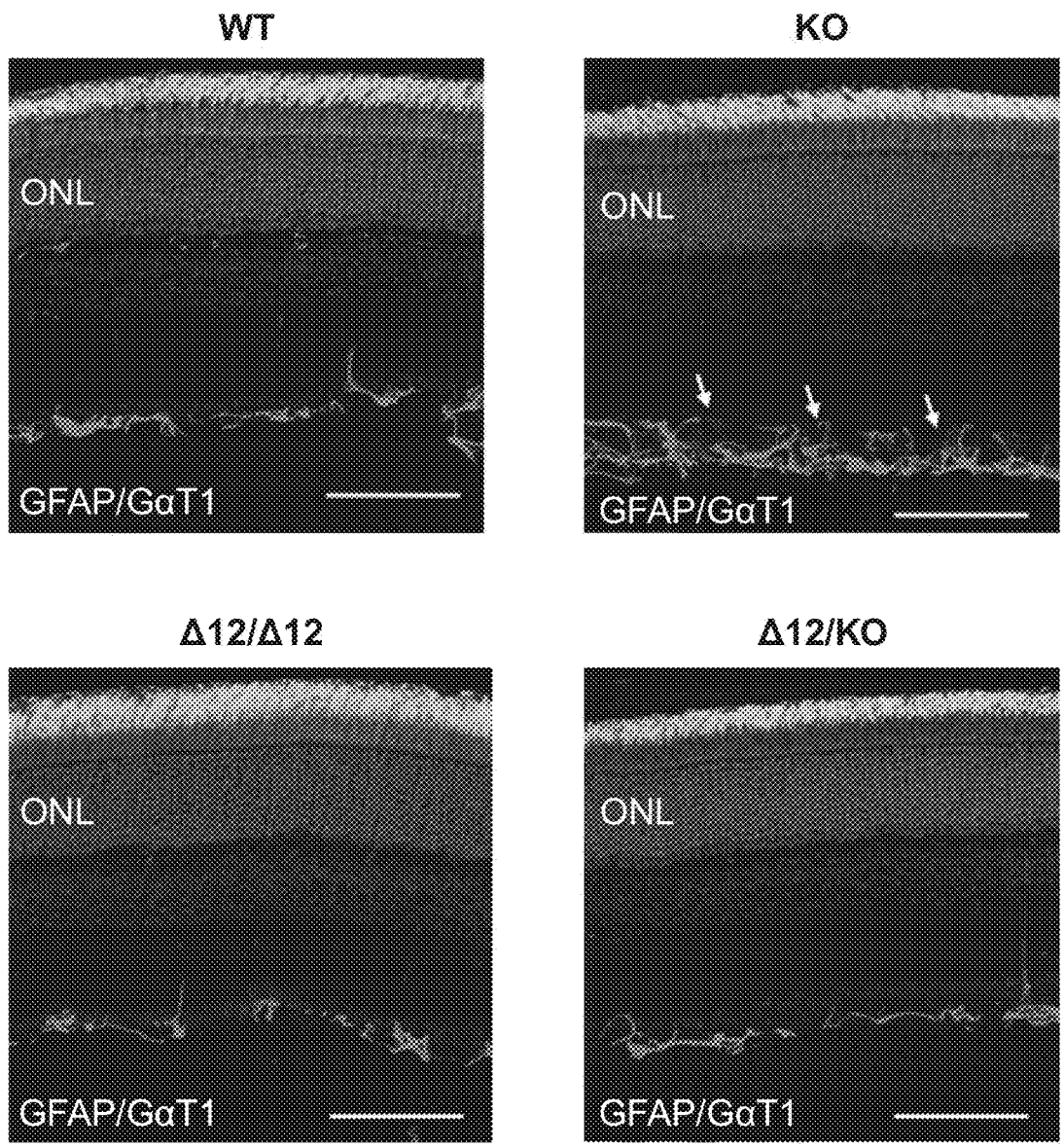
Figure 5K:
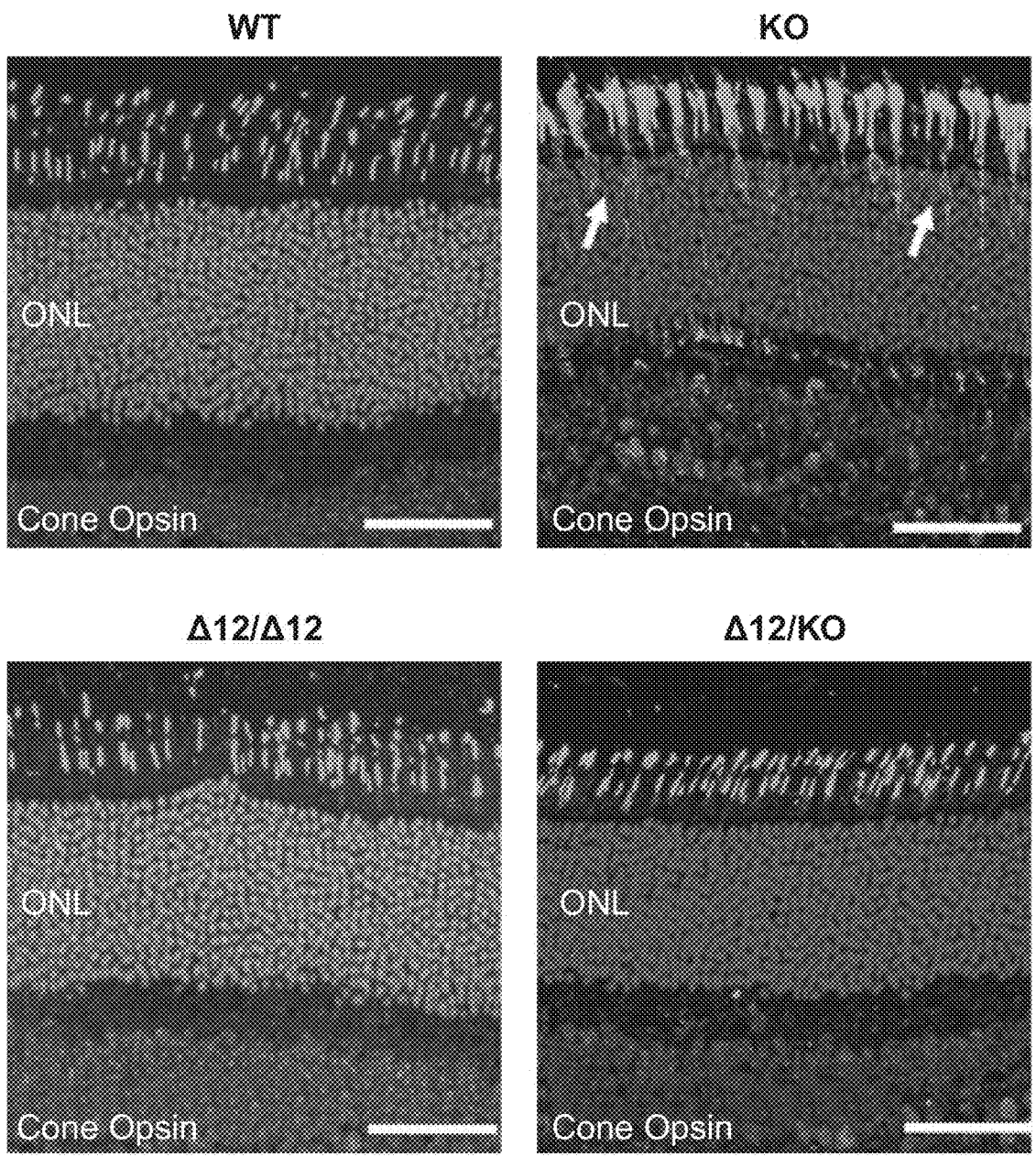
Figure 6:
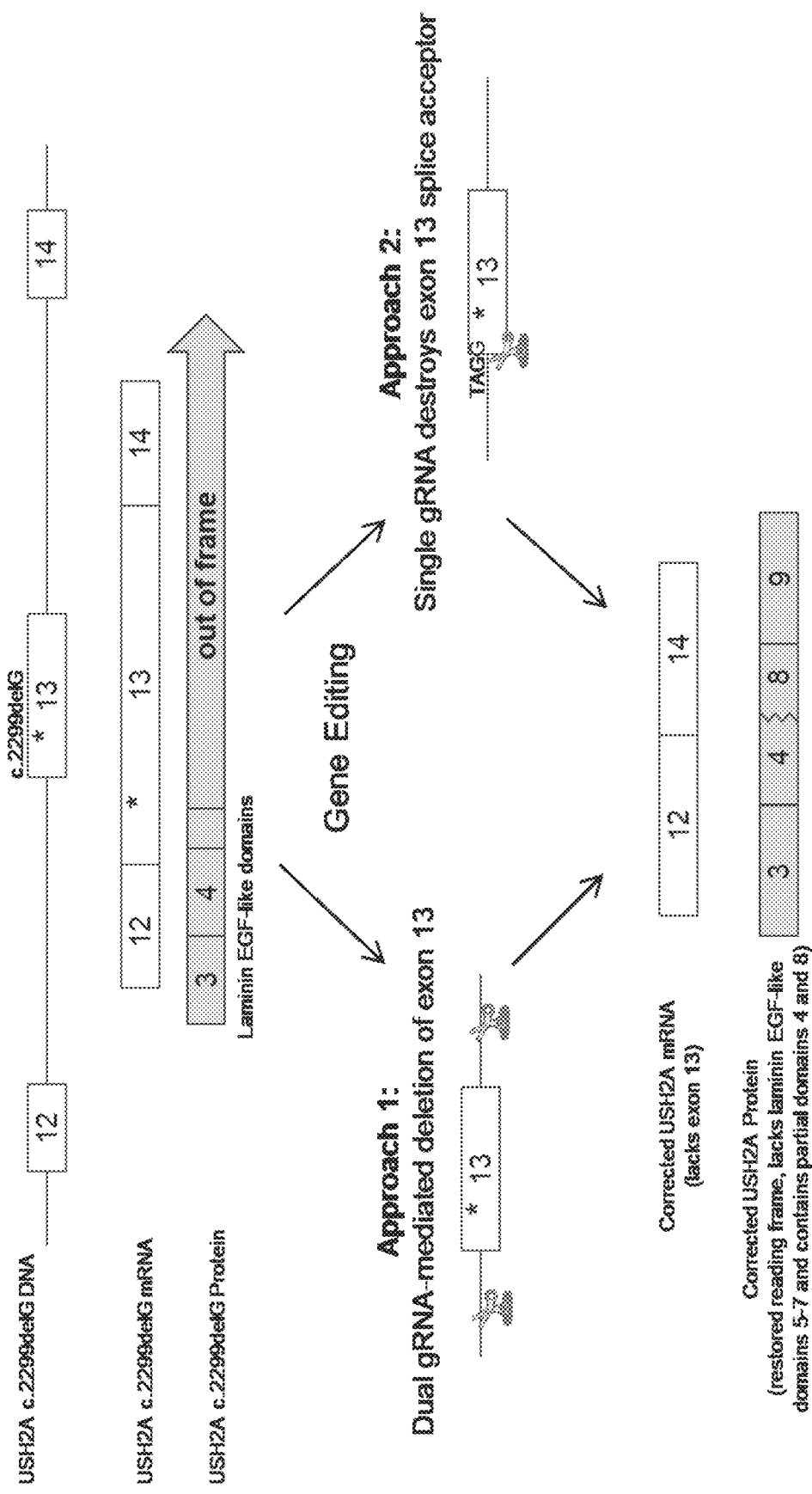
FIG. 6. Schematic illustration of two approaches to USH2A gene editing. Exons 12 and 14 are in frame with each other, so the goal of both approaches is to generate USH2A mRNA without exon 13 and thereby restore reading frame. The skipping of exon 13 results in the formation of a novel domain composed of the n-terminus of Laminin EGF-like (LE) domain repeat 4 and the C-terminus of LE repeat 8.
Figure 7:
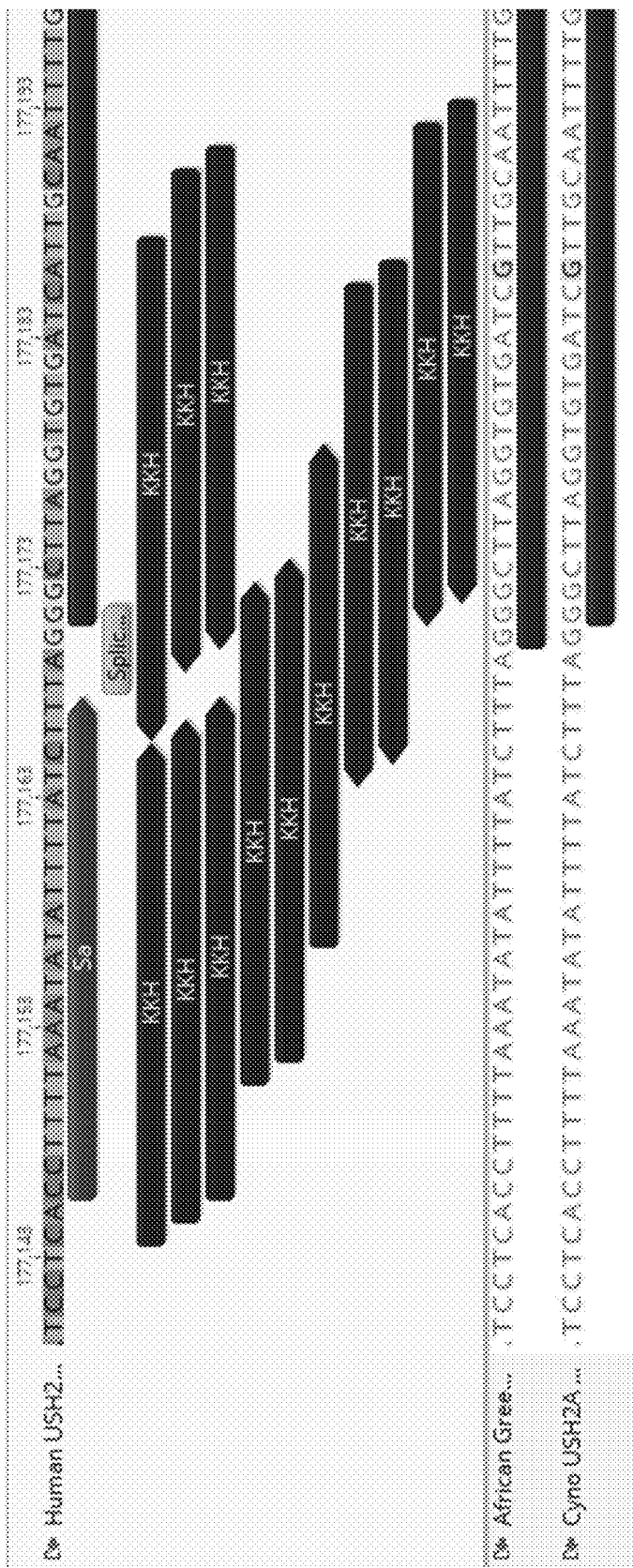
FIG. 7. The splice acceptor sequence is well-conserved across humans (SEQ ID NO:18), African Green monkeys (SEQ ID NO:19), and cynomolgus monkeys (SEQ ID NO: 20). The target site of SaCas9-KKH sgRNAs for disrupting the splicing acceptor of exon 13 in human USH2A gene.

In the retina, abnormal accumulation of GFAP in Ush2a ko/ko mice was reduced in the ΔEx12/ko mice at 3 months of age, and cone opsin localization was normalized in ΔEx12/ko mice at 3 months of age, as compared to ko/ko mice (FIGS. 5J-K).

These results showed that the protein encoded by Ush2a-ΔEx12 allele rescued the cochlear and retinal phenotypes observed in Ush2a$^{-/-}$ knockout mice.

Example 3. Humanized USH2A Mouse Models

A humanized USH2A mouse models is developed. Exon 12 of the mouse Ush2a gene, along with up to 1500 bp of the flanking introns, is replaced with the syntenic human exon 13 and up to 1500 bp of flanking introns. Two models are generated-one in which the wildtype human exon 13 is used and one in which the human exon 13 contains the c.2299delG mutation.

The expectation is that the mouse containing the wildtype human exon 13 will be phenotypically normal. This is supported by the high level of similarity between the amino acids encoded by mouse exon 12 and human exon 13 (74.8% exact sequence identity match and 86.9% sequence similarity match based on amino acid properties).

The expectation is that the mouse containing the c.2299delG mutation will exhibit an Usher Syndrome disease phenotype. As in Usher Syndrome patients, the c.2299delG mutation will result in a frameshift and premature stop codon, leading to a prematurely truncated, and non-functional protein. This is therefore expected to mimic the phenotype of the Ush2a knockout mouse (Ush2a$^{-/-}$) as described above The humanized Ush2a mouse models enable pharmacology PK/PD studies with human USH2A-targeted therapeutic guides. In addition, they enable demonstration of correction of disease phenotype. Lead gRNAs, along with Cas9 will be packaged in AAV. An example of what the configuration of this vector could look like is given in FIG. 9. Several AAV serotypes could be used, for example, AAV5, AAV8, AAV9 and AAV-Anc80 have all been demonstrated to show strong tropism for photoreceptors. 1 ul of AAV will be delivered to mice subretinally at doses ranging from 1E+11 to 1E+13 viral genomes/mL. Mice may be treated at different ages to assess ability to reverse pathology at various stages in disease. Mice will be evaluated at several time points to assess functional and structural rescue of retinal and cochlear phenotypes. Molecular analysis will determine expression levels of Cas9 and gRNAs as well as quantify targeted gene editing rates. ERG will measure photoreceptor function in the retina. Optical coherence tomography (OCT) and histology will examine retinal structure.

Example 4. sgRNAs for Exon13 Skipping in Humanized USH2A Mice

A comprehensive list of sgRNAs for SaCas9, SpCas9, their variants, and Cpf1 were generated to target the flanking intron 12 and 13 in the humanized USH2A mice. Those guides are individually screened in the human cell lines. Optimal pairs of sgRNAs are further evaluated for skipping the exon 13 in the humanized mice.

TABLE 4

Guide RNAs for flanking Intronic sequences of humanized exon 13

| Cas9 | PAM | Designed sgRNAs Intron 12 | Designed sgRNAs Intron 13 | selected for testing Intron 12 | selected for testing Intron 13 |
|---|---|---|---|---|---|
| SpCas9 | 5'-NGG-3' | 81 | 133 | 27 | 21 |
| SpCas9-VQR | 5'-NGA-3' | 186 | 248 | 21 | 23 |
| SpCas9-VRER | 5'-NGCG-3' | 3 | 1 | 0 | 0 |
| SaCas9 | 5'-NNGRRT-'3 | 52 | 54 | 12 | 24 |
| SaCas9-KKH | 5'-NNNRRT-'3 | 298 | 296 | 19 | 23 |
| AsCpf1 or LbCpf1 | 5'-TTTN-3' | 208 | 182 | 22 | 11 |
|  |  | 828 | 914 | 101 | 101 |

Example 5: Screening of gRNA

Guide RNAs were screened within human USH2A intron 12 and intron 13 to find the best cutting gRNAs. To this end, ability of 41 gRNAs within intron 12 and 72 gRNAs within intron 13 to generate indels in HEK293 cells was evaluated. The cells were transfected with RNPs, gDNA was isolated 48 hours later and subjected to PCR amplification and high-throughput sequencing and analysis to determine the editing rates for each gRNA (Table 5).

Figure 10A:
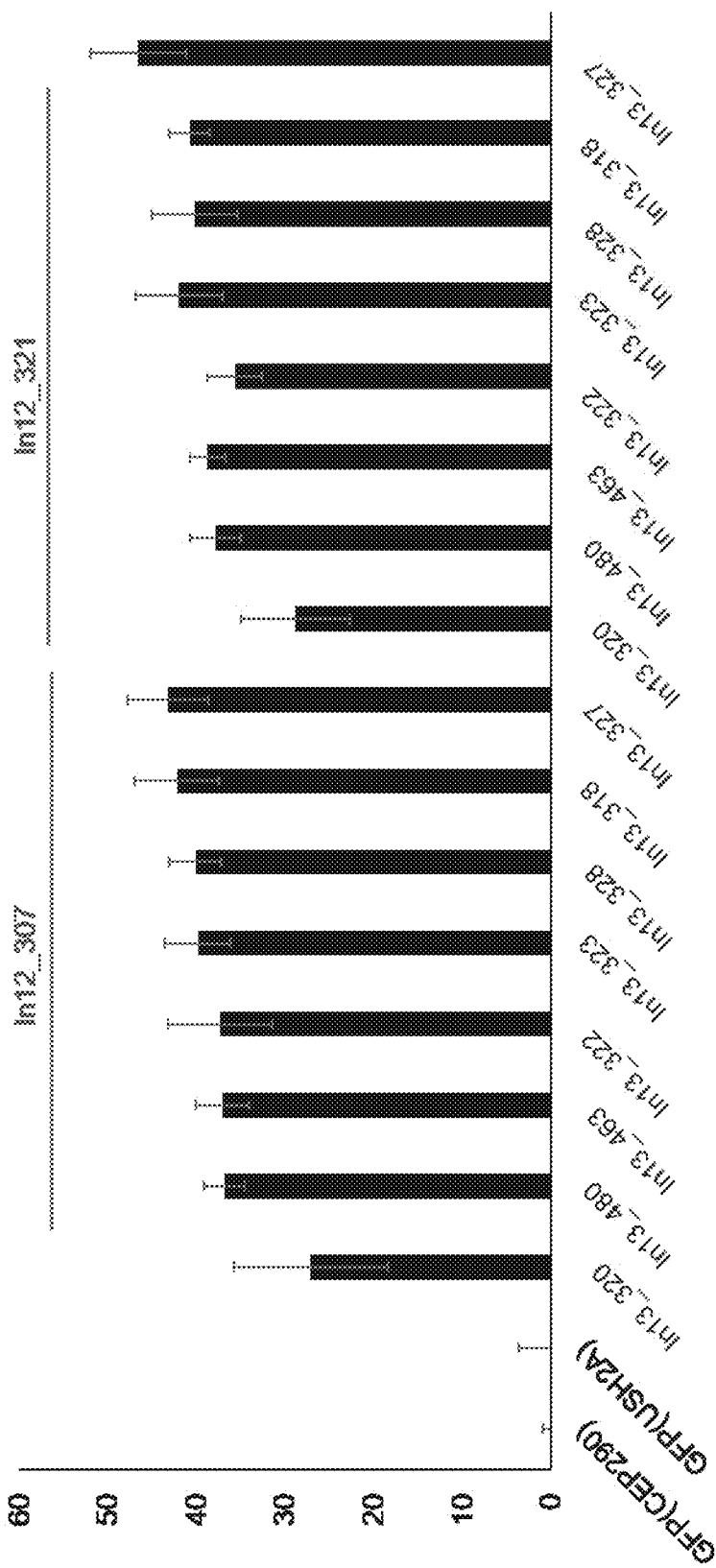
FIGS. 10A-B. Screening of top dual gRNA pairs and single splice acceptor gRNA. 10A: Editing of top 16 gRNA pairs for complete removal of USH2A exon 13 as determined by a ddPCR assay. 10B: Total editing of identified single gRNA that fall near the USH2A exon 13 splice acceptor.

Following this initial screen, a second screen focused on 2 intron 12 gRNAs and 8 intron 13 gRNAs which were identified from the initial screen. All the possible gRNA combinations were screened to determine which worked together to give the highest loss of exon 13. U2OS cells were transfected with plasmids that expressed *S. aureus* Cas9 and the gRNAs of interest and gDNA was isolated 48 hours later for analysis. Editing was determined with a ddPCR assay that measures the presence or absence of USH2A exon 13. Results are shown in FIG. 10A (N=3) for all gRNA combinations as well as negative controls (GFP).

Figure 10B:
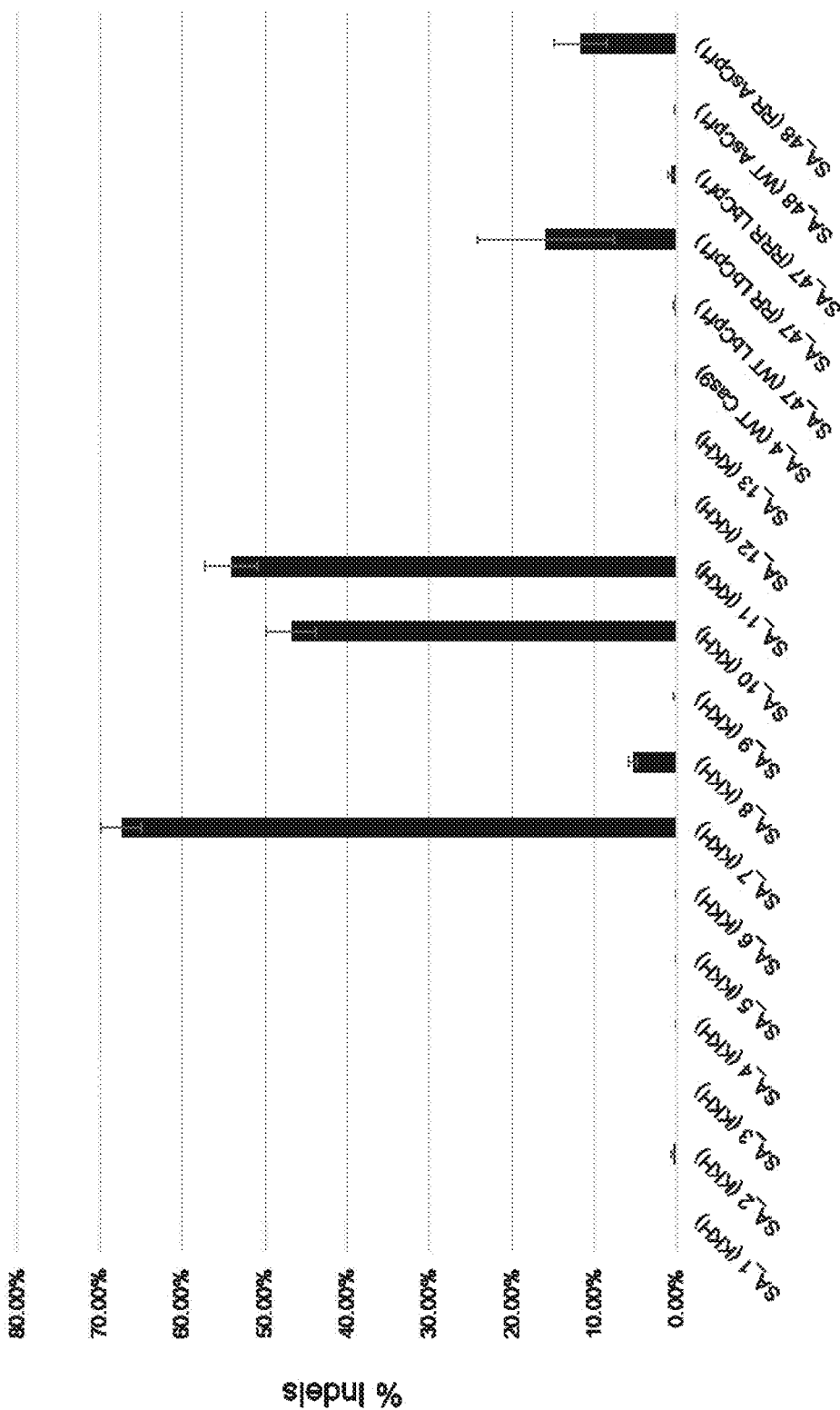

For the single gRNA approach, where the aim is to disrupt the exon 13 splice acceptor, gRNA that cut near the exon 13 splice acceptor were identified (Table 3). The ability of these gRNA to cut and form indels in U2OS cells was tested through plasmid transfection of CRISPR Cas9 or Cpf1 and the associated gRNA. The genomic DNA was extracted and subject to PCR amplification and sequencing to determine the percentage of indels (FIG. 10B).

TABLE 5

| Guide | Editing |
|---|---|
| in12_67 | 0.11% |
| in12_68 | 0.68% |
| in12_69 | 0.39% |
| in12_70 | 1.68% |
| in12_71 | 0.15% |
| in12_72 | 0.34% |
| in12_73 | 0.17% |
| in12_74 | 0.16% |
| in12_75 | 0.26% |
| in12_76 | 0.15% |
| in12_77 | 0.36% |
| in12_78 | 0.09% |
| in12_79 | 0.07% |
| in12_80 | 0.11% |
| in12_81 | 0.39% |
| in12_82 | 0.68% |
| in12_83 | 0.38% |
| in12_84 | 1.66% |
| in12_85 | 0.07% |
| in12_86 | 0.13% |
| in12_87 | 1.78% |
| in12_88 | 0.64% |
| in12_89 | 0.35% |
| in12_90 | 0.57% |
| in12_307 | 17.10% |
| in12_308 | 0.30% |
| in12_309 | 11.50% |
| in12_310 | 0.26% |
| in12_311 | 1.65% |
| in12_312 | 1.90% |
| in12_313 | 0.07% |
| in12_314 | 0.20% |
| in12_315 | 7.31% |
| in12_316 | 1.70% |
| in12_317 | 0.24% |
| in12_318 | 4.26% |
| in12_319 | 0.39% |
| in12_320 | 1.69% |
| in12_321 | 6.33% |
| in12_322 | 0.42% |
| in12_323 | 1.62% |
| in13_73 | 72.91% |
| in13_74 | 0.14% |
| in13_75 | 0.12% |
| in13_76 | 0.07% |
| in13_77 | 0.26% |
| in13_78 | 73.31% |
| in13_79 | 0.09% |
| in13_80 | 1.06% |
| in13_81 | 0.33% |
| in13_82 | 0.38% |
| in13_83 | 0.25% |
| in13_84 | 0.67% |
| in13_85 | 0.21% |
| in13_86 | 73.04% |
| in13_87 | 0.10% |
| in13_88 | 73.09% |
| in13_89 | 0.32% |
| in13_90 | 73.13% |
| in13_91 | 73.07% |
| in13_92 | 0.17% |
| in13_93 | 0.20% |
| in13_94 | 0.16% |
| in13_95 | 0.17% |
| in13_96 | 1.38% |

TABLE 5-continued

| Guide | Editing |
|---|---|
| in13_97 | 0.18% |
| in13_98 | 0.09% |
| in13_99 | 0.42% |
| in13_100 | 0.78% |
| in13_101 | 2.17% |
| in13_102 | 0.12% |
| in13_103 | 0.51% |
| in13_104 | 0.11% |
| in13_105 | 1.33% |
| in13_106 | 73.74% |
| in13_107 | 0.20% |
| in13_314 | 0.16% |
| in13_315 | 1.99% |
| in13_316 | 4.89% |
| in13_317 | 0.18% |
| in13_318 | 9.29% |
| in13_319 | 1.75% |
| in13_320 | 11.78% |
| in13_321 | 1.95% |
| in13_322 | 10.90% |
| in13_323 | 8.37% |
| in13_324 | 1.74% |
| in13_325 | 5.81% |
| in13_326 | 1.84% |
| in13_327 | 14.96% |
| in13_328 | 7.75% |
| in13_329 | 7.98% |
| in13_330 | 0.11% |
| in13_379 | 0.20% |
| in13_384 | 0.54% |
| in13_392 | 0.97% |
| in13_393 | 0.30% |
| in13_404 | 0.84% |
| in13_405 | 73.28% |
| in13_408 | 73.14% |
| in13_417 | 2.82% |
| in13_421 | 0.79% |
| in13_437 | 1.24% |
| in13_438 | 0.84% |
| in13_452 | 0.53% |
| in13_454 | 0.13% |
| in13_460 | 73.84% |
| in13_463 | 16.13% |
| in13_466 | 73.58% |
| in13_469 | 4.02% |
| in13_472 | 0.23% |
| in13_478 | 0.09% |
| in13_480 | 18.54% |

Example 6: Specificity of Top gRNA

The specificity of the top cutting gRNA for the dual gRNA approach was assessed using three different analyses. First, an in silico screen was conducted to identify all sites in the human genome where the particular guide could potentially cut, allowing for up to 3 mismatches or gaps in the protospacer sequence (Tables 6a and 6b).

Next, two different unbiased screens to identify off-target cut sites were completed. Guide-Seq was performed to assess the number and location of all editing events that occurred following treatment of cells with RNPs containing the one of the top gRNA. Guide-Seq was performed in primary human T cells after activation and expansion of the cells. The cells were nucleofected with RNPs and a short double-stranded oligo (Nat. Biotech. 2015, 33:187-197). gDNA was isolated, sheared, and adapters for PCR amplification were added before PCR amplification. DNA sequences adjacent to the Guide-Seq oligo were aligned to the genome to identify the location where the double-strand oligo was inserted.

Finally, Digenome-Seq was used as a second unbiased method to locate off-target cut sites. In this method, purified genomic DNA is mixed with RNP in a cell-free system (Nat. Methods 2015, 12:237-243). The DNA is then isolated, undergoes high-throughput sequencing, and is aligned to the human genome to identify locations where the DNA was cut (Tables 6a and 6b).

TABLE 6a

| | gRNA | # Digenome Off-Targets | # GUIDE-Seq Off-Targets | # In Silico Off-Targets |
|---|---|---|---|---|
| Intron 12 | In12_307 | 1 | 0 | 208 |
| | In12_321 | 1 | 0 | 14 |

TABLE 6b

| | gRNA | # Digenome Off-Targets | # GUIDE-Seq Off-Targets | # In Silico Off-Targets |
|---|---|---|---|---|
| Intron 13 | In13_318 | 9 | 0 | 400 |
| | In13_322 | 1 | 1 | 53 |
| | In13_323 | 1 | 0 | 42 |
| | In13_327 | 1 | 0 | 50 |
| | In13_328 | 2 | 1 | 47 |

Example 7: Human Model of USH2A Editing and Exon 13 Skipping in Cells

Figure 11A:
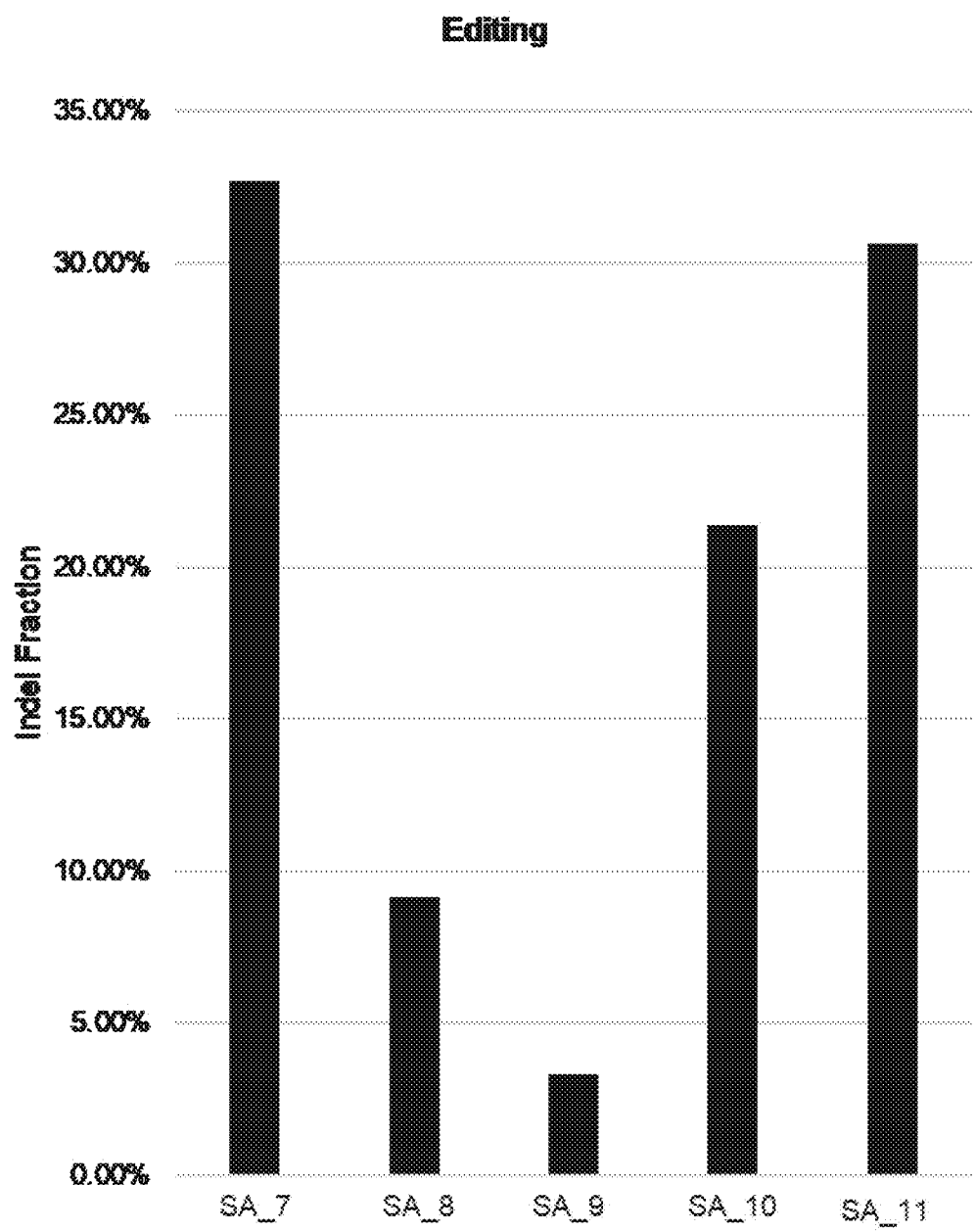
FIGS. 11A-D. Editing of USH2A human cells and measurement of USH2A delta exon 13 transcripts. 11A: Total editing of CRL-5923 cells with single gRNA targeting the exon 13 splice acceptor. 11B: Delta 13 USH2A transcripts compared to WT USH2A after editing with single gRNA as shown in 10A. 11C: Percent deletion of exon 13 after editing of CRL-5923 cells with the dual gRNA approach as determined by ddPCR. 11D. Delta 13 USH2A transcripts as a fraction of WT USH2A transcripts after editing with dual gRNAs as shown in 11C.

An RTddPCR assay to measure the amount of delta exon 13 USH2A transcript relative to WT USH2A was established. The WT assay amplifies the RNA junction between exons 13 and 14 while the delta 13 assay amplifies the junction between exon 12 and exon 14, which will only occur if exon 13 is precisely skipped (FIG. 11A). Another transcript ubiquitously expressed from Chromosome 1 (C1orf43) was used as a reference in this assay. The assay was validated with plasmids to check the linearity against expected inputs.

Figure 11B:
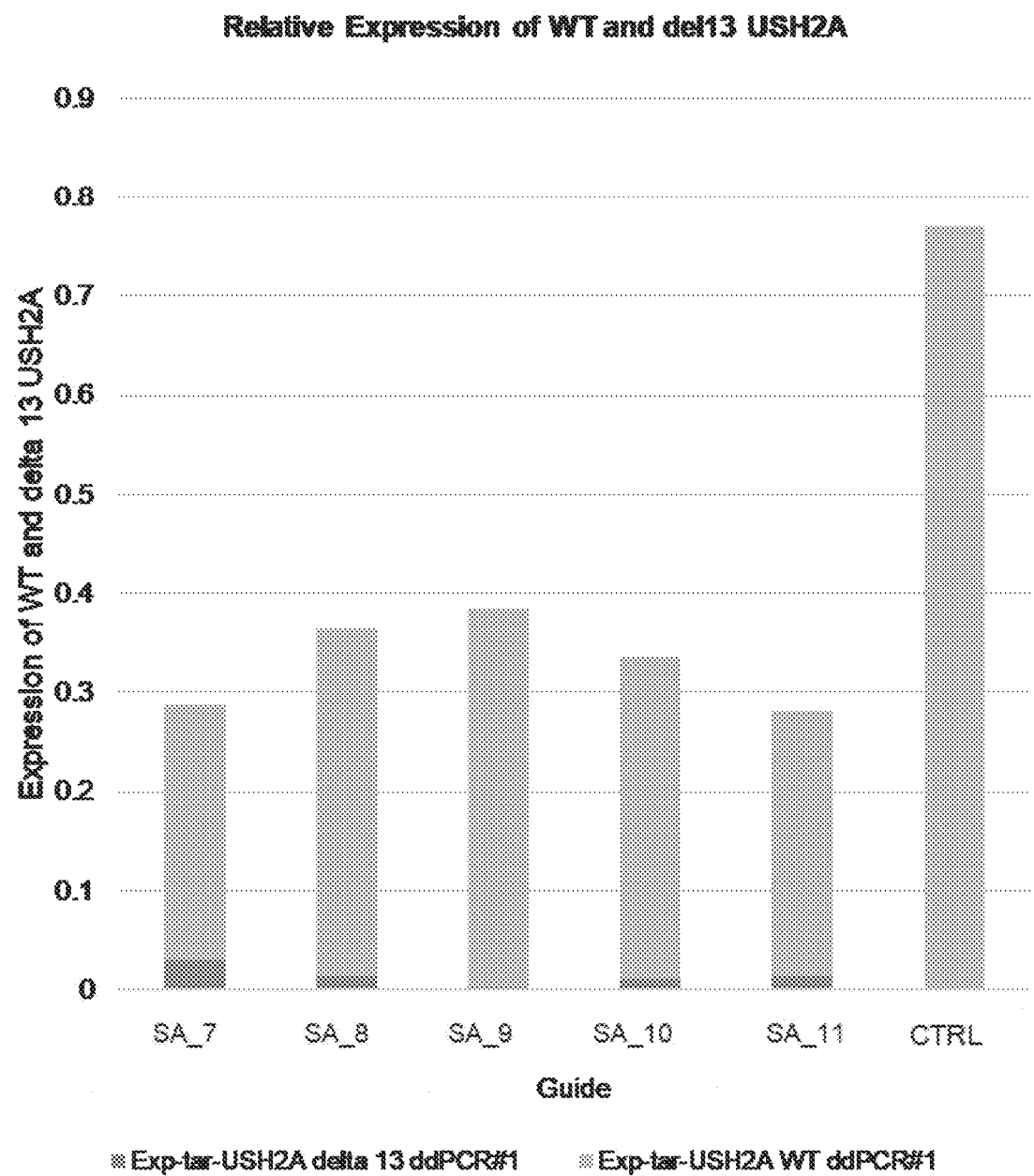
Figure 11C:
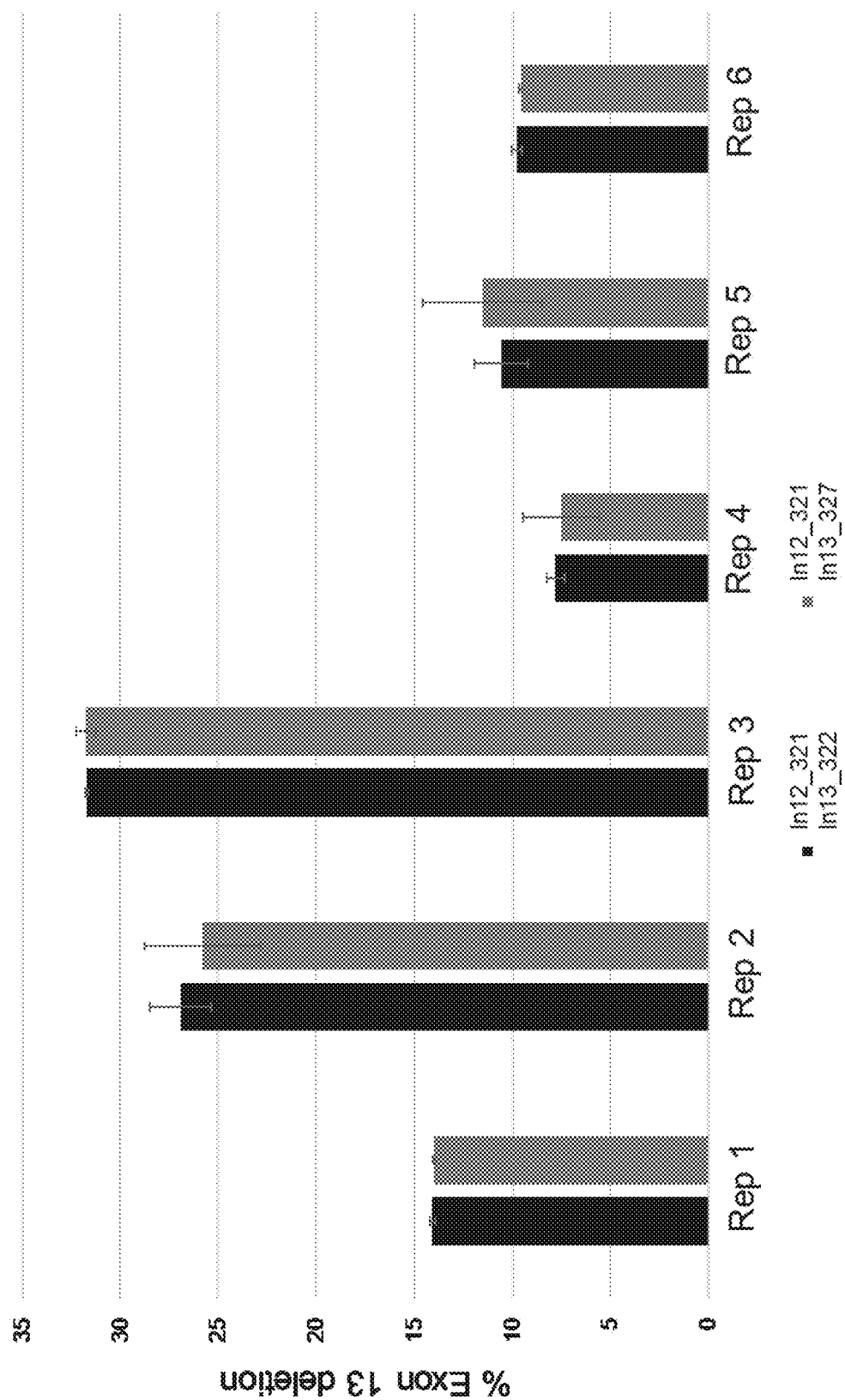

The ability of the assay to detect delta exon 13 USH2A transcripts after CRISPR/Cas9 mediated editing was tested in human CRL-5923 cells, which have been shown to express USH2A. CRL-5923 cells were transfected with plasmids expressing Cas9 and gRNA for the single guide approach and DNA and RNA were isolated from the cells 4 days after transfection. The DNA was assessed for genomic editing by high-throughput sequencing. RNA was used in the RTddPCR assay to measure the level of WT and delta exon 13 USH2A transcripts (FIGS. 11B-C).

Figure 11D:
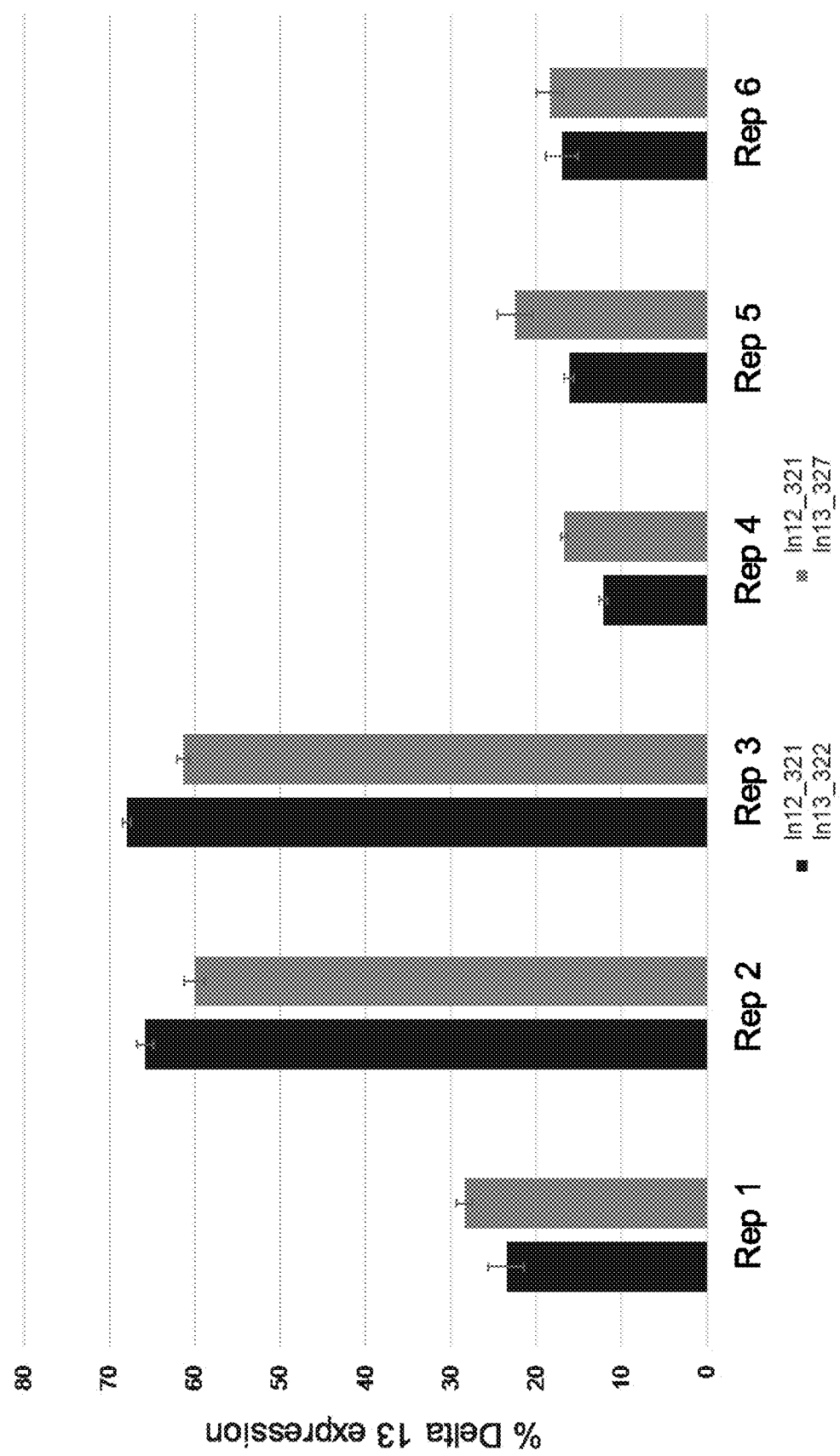

Editing and delta 13 USH2A expression was compared with two top pairs of gRNAs. CRL-5923 cells were nucleofected with RNPs containing the two gRNA and then DNA and RNA were isolated 4 days later (6 biological replicates). Loss of genomic USH2A exon 13 was measured by a ddPCR assay (FIG. 11D) and levels of WT and delta exon 13 USH2A transcripts were measured by RTddPCR (FIG. 11E).

Example 8: Editing of USH2A in Human Retinal Explants

Figure 12:
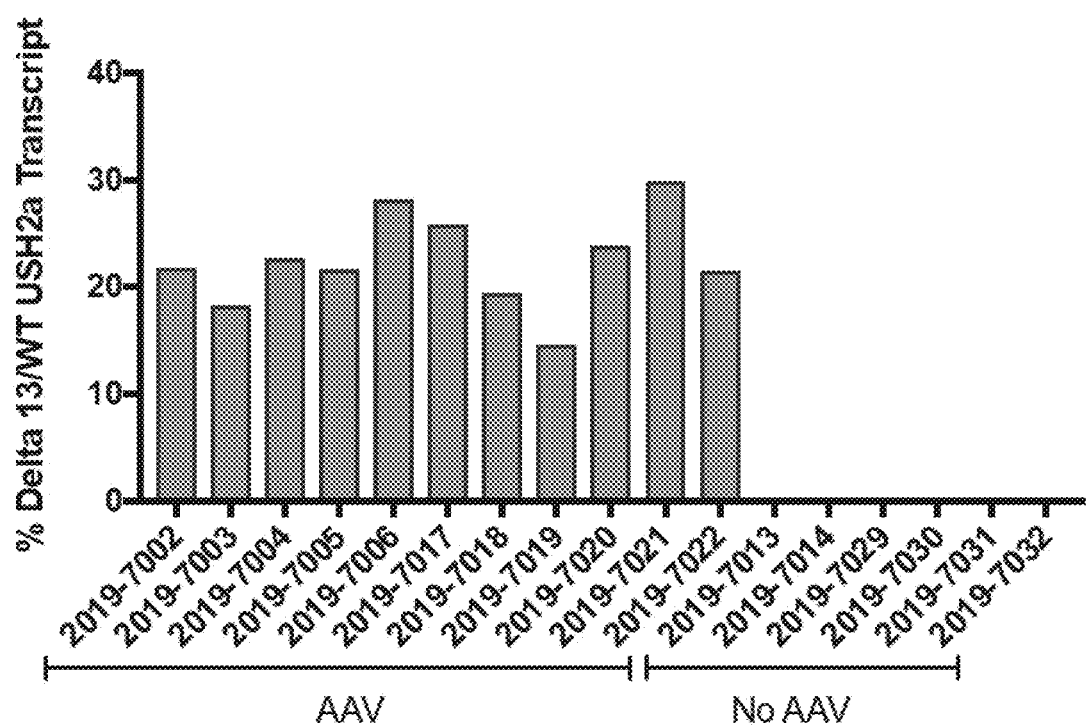
FIG. 12. Percent expression of delta 13 USH2A transcripts in human retinal explants after editing with dual guide approach delivered as an AAV5.

AAV5 vectors were cloned and produced to express in12_321 and in13_322 as depicted in FIG. 9. Retinal explant punches (3 millimeters) were taken from cadaver eyes within 5 hours post-mortem and individually cultured on membranes. 10 µL of AAV at a titer of 5e13 vg/mL was added between the neural retina and the membrane such that it created a viral bleb under the retinal tissue. Tissue was incubated for 28 days at which point the punches were collected. Each punch was split in half, one half for gDNA and the other half for RNA isolation. PCR amplification and sequencing showed that the punches treated with AAV had between 5-40% total editing, while untreated control punches had background levels of editing. RNA was used for RTddPCR analysis to determine whether editing had caused production of USH2A delta exon 13 transcripts. Analysis showed that between 14-30% of USH2A transcripts were lacking exon 13 (FIG. 12).

SEQUENCES

Human USH2A mRNA lacking exon 13: (exon 12 in bold, exon 14 double underlined)

```
(SEQ ID NO: 1)
TGTTTGCTCTGCAGAATACTTTACCTGGGCACCCAAGTCTTCCTTCCAGCATTCCTGCTGCTA

CAGCCTATTTGCTGAGTAACCAGGGGTTACAGCAGCGTTGCCAGGCAACGAGGGACAGCG

GTCCTGTTGAAGAGCCATTTGTCACACTGAGGGGACTGGTTGAAATGCAATAAAGAAATGA

TACCAGCAGCTACTCATGTCTTCGCCATTGCTAAGAACGTCGTTGGTATTACCTTACTCTGAG

AACGTGTCTGCAGTTTCCAGAAAATGGAGTATCGCAACATCACTTAAAGTACCCTGCTTCAA

AGTATTGCTGGCAAGTGGCGTGGGCCTGATTATTTATTTAGAAATGCTTTATCAGGAGGAG

AATGCTTTTTTGTAAACATGAATTGCCCAGTTCTTTCATTGGGCTCTGGCTTCTTGTTTCAGG

TCATTGAAATGTTGATCTTTGCCTATTTTGCTTCAATATCCTTGACTGAGTCACGAGGTCTTTT

CCCAAGGCTGGAGAACGTGGGAGCTTTCAAGAAAGTTTCCATCGTGCCAACCCAAGCAGTA

TGTGGACTCCCAGACCGAAGCACTTTTTGTCACAGCTCTGCTGCTGCTGAAAGTATTCAGTT

CTGTACCCAGCGGTTTTGTATTCAGGATTGCCCATACAGATCTTCACACCCTACCTACACTGC

CCTTTTCTCAGCAGGCCTCAGTAGCTGCATCACACCAGACAAGAATGATCTGCATCCTAACG

CCCATAGCAATTCTGCAAGTTTTATTTTTGGAAATCACAAGAGCTGCTTTTCTTCTCCTCCTTC

TCCAAAGCTGATGGCATCATTTACCTTAGCTGTATGGCTGAAACCTGAGCAACAAGGTGTAA

TGTGTGTTATAGAAAAGACAGTAGATGGGCAGATTGTGTTCAAACTTACAATATCTGAGAA

AGAGACCATGTTTTATTATCGCACAGTAAATGGTTTGCAACCTCCAATAAAAGTAATGACAC

TGGGGAGAATTCTTGTGAAGAAATGGATTCATCTTAGTGTGCAGGTGCATCAGACAAAAAT

CAGCTTCTTTATCAATGGCGTGGAGAAGGATCATACACCTTTCAATGCAAGAACTCTAAGTG

GTTCAATTACAGATTTTGCATCTGGTACTGTGCAAATAGGACAGAGTTTAAATGGTTTAGAG

CAGTTTGTCGGAAGAATGCAAGATTTTCGATTATACCAAGTGGCACTTACAAACAGAGAGA

TTCTGGAAGTCTTCTCTGGAGATCTTCTCAGATTGCATGCCCAATCACATTGCCGTTGCCCTG

GCAGCCACCCGCGGGTCCACCCTTTGGCACAGCGGTACTGCATTCCTAATGATGCAGGAGA

CACAGCTGATAATAGAGTGTCACGGTTGAATCCTGAAGCCCATCCTCTCTCTTTTGTCAATG

ATAATGATGTTGGTACTTCATGGGTTTCAAATGTGTTTACAAACATTACACAGCTTAATCAA

GGAGTGACTATTTCAGTTGATTTGGAAAATGGACAGTATCAGGTGTTTTATATTATCATTCA

GTTCTTTAGTCCACAACCAACGGAAATAAGGATTCAAAGGAAGAAGGAAAATAGTTTAGAT

TGGGAGGACTGGCAATATTTTGCCAGGAATTGTGGTGCTTTTGGAATGAAAAACAATGGAG

ATTTGGAAAAACCTGATTCTGTCAACTGTCTTCAGCTTTCCAATTTTACTCCATATTCCCGTGG

CAATGTCACATTTAGCATCCTGACACCTGGACCAAATTATCGTCCTGGATACAATAACTTCTA

TAATACCCCATCTCTTCAAGAGTTCGTAAAAGCCACGCAAATAAGGTTTCATTTTCATGGGC

AGTACTATACAACTGAGACTGCTGTTAACCTCAGACACAGATATTATGCAGTGGACGAAATC

ACCATTAGTGGGAGATGTCAGTGCCATGGTCATGCCGATAACTGCGACACAACAAGCCAGC

CATATAGATGCCTCTGCTCCCAGGAGAGCTTCACTGAAGGACTTCATTGTGATCGCTGCTTG

CCTCTTTATAATGACAAGCCTTTCCGCCAAGGTGATCAAGTTTACGCTTTCAATTGTAAACCT

TGTCAATGCAACAGCCATTCCAAAAGCTGCCATTACAACATCTCTGTAGACCCATTTCCTTTT
```

-continued

```
GAGCACTTCAGAGGGGGAGGAGGAGTTTGTGATGATTGTGAGCATAACACTACAGGAAGG

AACTGTGAGCTGTGCAAGGATTACTTTTTCCGACAAGTTGGTGCAGATCCTTCGGCCATAGA

TGTTTGCAAACCCTGTGACTGTGATACAGTTGGCACTAGAAATGGTAGCATTCTTTGTGATC

AGATTGGAGGACAGTGTAATTGTAAGAGACACGTGTCTGGCAGGCAGTGCAATCAGTGC

CAGAATGGATTCTACAATCTACAAGAGTTGGATCCTGATGGCTGCAGTCCCTGTAACTGCA

ATACCTCTGGGACAGTGGATGGAGATATTACCTGTCACCAAAATTCAGGCCAGTGCAAGT

GCAAAGCAAACGTTATTGGTTTTTATATTTCTCCAGGCAATGCCACTGGCTGCCTGCCATGC

TCATGCCATACAACTGGTGCAGTTAATCACATCTGTAATAGCCTGACTGGTCAGTGTGTTTG

CCAAGATGCTTCCATTGCTGGGCAACGTTGTGACCAATGCAAAGACCATTACTTTGGATTTG

ATCCTCAGACTGGAAGATGTCAGCCTTGTAATTGTCATCTCTCAGGAGCCTTGAATGAAACC

TGTCACTTGGTCACAGGCCAGTGTTTCTGTAAACAATTTGTCACTGGCTCAAAGTGTGATGC

TTGTGTTCCCAGTGCAAGCCACTTGGATGTCAACAATCTATTGGGTTGCAGCAAAACTCCAT

TCCAGCAACCTCCGCCCAGAGGACAAGTTCAAAGTTCTTCTGCTATCAATCTCTCCTGGAGT

CCACCTGATTCTCCAAATGCCCACTGGCTTACTTACAGTTTACTCAGGGATGGTTTTGAAATC

TACACAACAGAGGATCAATACCCATACAGTATTCAATACTTCTTAGACACAGACCTGTTACC

ATATACCAAATATTCCTATTACATTGAGACCACCAATGTGCATGGTTCAACAAGGAGTGTAG

CTGTCACTTACAAGACAAAACCAGGGGTCCCAGAGGGAAACTTGACTTTAAGTTATATCATT

CCTATTGGCTCAGACTCTGTGACACTTACCTGGACAACACTCTCAAATCAATCTGGTCCCATA

GAGAAATATATTTTGTCCTGTGCCCCTTTGGCTGGTGGTCAGCCATGTGTTTCCTACGAAGG

TCATGAAACCTCAGCTACCATCTGGAATCTGGTTCCATTTGCCAAGTACGATTTTTCTGTACA

GGCGTGTACTAGCGGGGCTGTTTACACAGCTTGCCCATTACAGTGACCACAGCCCAGGCC

CCTCCCCAAAGACTAAGTCCACCTAAGATGCAGAAAATCAGTTCTACAGAACTTCATGTAGA

ATGGTCTCCACCAGCGGAACTAAATGGAATAATTATAAGATATGAACTATACATGAGAAGA

CTGAGATCTACTAAAGAAACCACATCTGAGGAAAGTCGAGTTTTTCAGAGCAGTGGTTGGC

TCAGTCCTCATTCATTTGTAGAATCGGCCAATGAAAATGCATTAAAACCTCCTCAAACAATG

ACAACCATCACTGGCTTGGAGCCATACACCAAGTATGAGTTCAGAGTCTTAGCTGTGAATAT

GGCTGGAAGTGTGTCTTCTGCCTGGGTCTCAGAAAGAACGGGAGAATCAGCACCTGTATTC

ATGATCCCTCCTTCAGTCTTTCCCCTCTCTTCGTACTCTCTCAATATCTCCTGGGAGAAGCCAG

CAGATAATGTTACAAGAGGAAAAGTTGTGGGGTATGACATCAATATGCTTTCTGAACAATC

ACCTCAACAGTCTATTCCCATGGCGTTTTCACAGCTGTTGCACACTGCTAAATCCCAAGAACT

ATCTTACACTGTAGAAGGACTGAAACCTTATAGGATATATGAGTTTACTATTACTCTCTGCAA

TTCAGTTGGTTGTGTGACCAGTGCTTCGGGAGCAGGACAAACTTTAGCAGCAGCACCAGCA

CAACTGAGGCCACCTCTGGTTAAAGGAATCAACAGCACAACAATCCATCTTAAGTGGTTTCC

ACCTGAAGAACTGAATGGACCCTCTCCTATATATCAGCTGGAAAGGAGAGAGTCATCTCTAC

CAGCTCTGATGACCACGATGATGAAAGGAATCCGTTTCATAGGAAATGGGTATTGTAAATTT

CCCAGCTCCACTCACCCAGTCAATACAGACTTCACTGGCATTAAGGCCAGCTTTCGAACAAA

AGTGCCTGAAGGTTTGATTGTCTTTGCAGCATCACCTGGCAATCAGGAAGAGTATTTTGCAC

TTCAGTTGAAGAAGGGACGTCTTTATTTTCTTTTTGATCCTCAGGGGTCACCAGTGGAAGTA

ACTACAACTAATGATCATGGCAAACAATATAGTGATGGAAAATGGCATGAAATAATTGCTA

TTAGGCATCAGGCTTTTGGCCAAATCACTCTGGATGGGATATATACAGGTTCCTCTGCCATC

CTGAATGGTAGTACTGTTATTGGAGATAACACAGGAGTCTTTCTGGGAGGGCTCCCGCGAA
```

-continued

```
GTTATACCATCCTCAGGAAGGATCCTGAGATAATCCAAAAAGGTTTTGTGGGCTGTCTCAAG

GATGTACATTTTATGAAGAATTACAATCCGTCAGCTATTTGGGAACCTCTGGATTGGCAGAG

TTCTGAAGAACAAATCAACGTGTATAACAGCTGGGAGGGATGTCCCGCTTCATTAAATGAG

GGAGCTCAGTTCCTAGGAGCAGGGTTCCTGGAACTTCATCCATATATGTTTCATGGTGGAAT

GAACTTTGAGATTTCCTTTAAGTTCAGAACTGACCAATTAAATGGATTGCTTCTTTTCGTTTA

TAACAAAGATGGACCTGATTTTCTTGCTATGGAGCTGAAAAGTGGAATATTGACCTTCCGGT

TAAATACCAGTCTTGCCTTTACACAAGTGGATCTATTGCTGGGGCTATCCTATTGTAATGGA

AAGTGGAATAAAGTCATTATTAAAAAGGAAGGCTCTTTCATATCAGCAAGTGTGAATGGAC

TGATGAAGCATGCATCGGAGTCCGGAGACCAGCCACTGGTGGTGAATTCACCAGTTTATGT

GGGAGGAATCCCACAGGAACTGCTGAACTCTTATCAACATTTGTGTTTGGAACAAGGTTTC

GGTGGTTGCATGAAGGATGTTAAATTTACACGGGGTGCTGTCGTTAACTTGGCATCTGTGTC

CAGCGGTGCTGTCAGAGTCAATCTGGATGGATGCCTATCAACTGACAGTGCTGTTAACTGC

AGGGGAAATGACTCCATCCTGGTTTACCAGGGAAAAGAGCAGAGTGTTTACGAGGGTGGT

CTCCAGCCTTTTACAGAATACCTGTATCGAGTGATAGCCTCGCATGAAGGAGGTTCAGTATA

TAGTGATTGGAGTCGAGGACGTACAACAGGAGCAGCTCCACAAAGTGTGCCAACTCCCTCA

AGAGTCCGCAGCTTAAATGGATACAGCATTGAGGTGACCTGGGATGAACCTGTTGTCAGAG

GTGTAATTGAGAAGTACATTCTGAAAGCCTATAGTGAGGACAGCACCCGTCCACCCCGCAT

GCCCTCTGCCAGTGCTGAATTTGTCAATACAAGCAACCTCACAGGCATATTGACAGGCTTGC

TACCCTTCAAAAACTATGCAGTAACCCTAACTGCTTGCACTTTGGCTGGCTGTACTGAGAGC

TCACATGCATTGAACATCTCTACTCCACAAGAAGCCCCACAAGAGGTTCAGCCACCAGTAGC

CAAATCCCTTCCCAGTTCTTTGCTGCTCTCCTGGAACCCACCCAAAAAGGCAAATGGTATTAT

AACTCAGTACTGTTTATACATGGATGGGAGGCTGATCTATTCAGGCAGTGAGGAGAACTAC

ACAGTCACAGATTTAGCAGTATTTACACCCCACCAGTTTCTACTAAGTGCATGCACACATGT

GGGCTGTACAAACAGTTCCTGGGTCCTACTGTACACAGCACAGCTGCCACCAGAACACGTG

GATTCCCCAGTTCTGACTGTCCTGGATTCTAGAACTATACACATACAGTGGAAACAACCAAG

AAAAATAAGTGGGATTCTGGAACGCTATGTATTATATATGTCAAACCATACACATGATTTTA

CAATTTGGAGTGTCATCTATAAACAGTACAGAACTTTTCCAGGATCATATGCTACAATACGTTT

TACCTGGTAATAAATATCTCATCAAGCTGGGAGCTTGCACAGGTGGTGGGTGCACAGTGAG

TGAGGCCAGTGAGGCCCTAACTGACGAGGACATACCCGAAGGCGTGCCAGCCCCCAAAGC

CCACTCATATTCACCTGACTCCTTTAATGTCTCCTGGACTGAGCCTGAATATCCGAATGGTGT

TATCACGAGTTATGGATTATATCTAGATGGTATATTAATCCACAATTCCTCAGAACTCAGCTA

TCGTGCTTACGGATTTGCTCCTTGGAGTTTACATTCCTTCAGAGTCCAAGCATGCACGGCCA

AAGGTTGTGCTCTGGGCCCACTGGTGGAAAATCGAACTCTAGAAGCTCCTCCTGAAGGAAC

AGTAAATGTGTTTGTCAAAACACAGGGATCCCGGAAAGCCCACGTGAGGTGGGAAGCACC

TTTTCGCCCTAATGGACTCTTAACACACTCAGTCCTTTTCACTGGGATATTCTATGTAGACCC

AGTAGGTAATAACTACACCCTTCTGAATGTCACAAAAGTCATGTACAGCGGAGAAGAGACA

AACCTTTGGGTGCTCATCGATGGGCTGGTTCCTTTTACCAACTATACTGTACAAGTGAATATT

TCAAATAGCCAAGGCAGCTTGATAACTGATCCTATAACAATTGCAATGCCTCCAGGAGCTCC

AGATGGCGTGCTGCCTCCCAGGCTTTCATCTGCCACTCCAACCAGTCTTCAGGTTGTCTGGT

CTACACCAGCTCGTAATAACGCTCCTGGCTCTCCCAGATACCAACTCCAGATGAGGTCTGGC
```

-continued

```
GACTCCACCCATGGATTTCTAGAGTTATTTTCCAATCCTTCTGCATCGTTAAGCTATGAAGTG

AGTGATCTCCAACCGTACACAGAGTATATGTTTCGGTTGGTTGCCTCCAATGGATTTGGCAG

TGCACATAGTTCTTGGATTCCATTCATGACCGCAGAGGACAAACCTGGACCTGTAGTTCCTC

CGATTCTTCTGGATGTGAAGTCAAGAATGATGTTGGTCACCTGGCAGCATCCTAGAAAATCC

AATGGGGTTATTACCCATTATAACATTTATCTACATGGCCGTCTATACTTGAGAACTCCTGGA

AATGTCACTAATTGCACAGTGATGCATTTACACCCATACACTGCCTATAAGTTTCAGGTAGA

AGCCTGCACTTCAAAAGGATGTTCCCTTTCACCAGAGTCCCAGACTGTATGGACACTCCCAG

GGGCACCGGAAGGGATCCCAAGTCCAGAGCTGTTCTCTGATACTCCAACATCTGTGATTATA

TCTTGGCAACCCCCTACCCACCCCAATGGCTTGGTGGAGAATTTCACAATTGAGAGAAGAGT

CAAAGGAAAGGAAGAAGTTACTACCCTGGTGACTCTCCCGAGGAGTCATTCCATGAGGTTT

ATTGACAAGACTTCTGCTCTTAGCCCATGGACAAAATATGAATATCGGGTACTGATGAGCAC

TCTTCATGGAGGCACAAACAGCAGTGCTTGGGTAGAAGTTACCACAAGACCCTCACGACCT

GCTGGGGTGCAGCCACCTGTGGTGACAGTGCTGGAACCCGATGCAGTCCAGGTCACTTGG

AAACCCCCACTCATCCAGAACGGAGACATACTTAGCTATGAGATTCACATGCCTGACCCTCA

CATCACTTTAACCAATGTGACTTCCGCAGTGTTAAGTCAAAAAGTTACTCATCTGATTCCTTT

CACTAATTATTCTGTCACCATTGTTGCTTGCTCAGGGGGTAATGGGTACCTTGGAGGGTGCA

CAGAGAGTTTACCTACCTATGTTACCACTCACCCCACCGTACCTCAGAATGTTGGCCCATTGT

CTGTGATTCCACTAAGTGAATCATATGTTGTGATTTCTTGGCAACCACCATCCAAGCCAAAT

GGACCTAATTTGAGATATGAGCTTCTGAGACGTAAAATCCAGCAGCCACTTGCATCAAATCC

CCCAGAAGATTTAAATCGGTGGCACAATATTTATTCAGGAACTCAGTGGCTTTATGAAGATA

AGGGTCTTAGCAGGTTTACAACCTATGAATATATGCTCTTCGTACACAACAGTGTGGGTTTT

ACACCGAGCCGAGAAGTGACTGTGACAACGTTAGCTGGTCTTCCAGAGAGAGGAGCCAAT

CTCACTGCGAGTGTCCTTAACCACACAGCCATCGACGTGAGGTGGGCTAAACCAACTGTTCA

AGACCTACAAGGTGAAGTTGAATATTACACACTTTTTTGGAGTTCTGCTACCTCAAACGACT

CTCTAAAAATCTTGCCAGATGTAAACTCTCATGTCATTGGCCACCTAAAGCCAAACACAGAG

TATTGGATCTTTATCTCTGTCTTCAATGGAGTCCACAGCATCAACAGTGCAGGACTTCATGCA

ACCACTTGCGATGGGGAGCCTCAGGGCATGCTTCCTCCAGAGGTTGTCATCATCAACAGTA

CAGCTGTACGTGTCATCTGGACATCTCCTTCAAACCCAAATGGTGTTGTCACTGAGTATTCTA

TCTATGTAAATAATAAGCTCTACAAGACTGGAATGAATGTGCCTGGGTCGTTTATTCTGAGA

GACCTGTCTCCCTTCACTATCTATGACATTCAGGTTGAAGTCTGCACAATATATGCCTGCGTG

AAAAGCAATGGAACCCAAATTACCACTGTGGAAGACACTCCAAGTGATATACCAACACCCA

CAATTCGTGGCATCACTTCAAGATCTCTTCAAATTGATTGGGTGTCTCCACGGAAGCCAAAT

GGCATCATTCTTGGATATGATCTCCTATGGAAAACATGGTATCCATGCGCTAAAACTCAAAA

GTTAGTGCAGGATCAGAGTGATGAGCTCTGCAAGGCAGTGAGGTGTCAAAAACCTGAATCT

ATCTGTGGACACATTTGCTATTCTTCTGAAGCTAAGGTTTGTTGTAACGGAGTGCTCTATAAC

CCCAAGCCTGGACATCGCTGTTGTGAAGAAAAGTATATCCCGTTTGTTCTGAATTCTACTGG

AGTTTGTTGTGGTGGCCGAATACAGGAGGCACAACCAAATCATCAGTGCTGCTCGGGTAT

TACGCTAGAATTCTACCAGGTGAAGTATGCTGTCCAGATGAACAGCACAATCGGGTTTCTGT

TGGCATTGGTGATTCCTGCTGTGGCAGAATGCCGTACTCCACCTCAGGAAACCAGATTTGCT

GTGCTGGGAGGCTTCATGATGCCATGGCCAGAAGTGCTGTGGCAGACAGATTGTGAGCA

ACGATTTAGAGTGTTGTGGTGGAGAAGAAGGAGTGGTGTACAATCGCCTTCCAGGTATGTT
```

-continued

```
CTGTTGTGGGCAGGATTATGTGAATATGTCAGATACCATATGCTGCTCAGCTTCCAGTGGAG

AGTCTAAAGCACATATTAAAAAGAATGACCCGGTGCCAGTAAAATGCTGTGAGACTGAACT

TATTCCAAAGAGCCAGAAATGCTGTAATGGAGTTGGATATAATCCTTTGAAATATGTTTGCT

CTGACAAGATTTCAACTGGAATGATGATGAAGGAAACCAAAGAGTGCAGGATCCTCTGCCC

AGCATCTATGGAAGCCACAGAACATTGTGGCAGGTGTGACTTCAACTTTACCAGCCACATTT

GCACTGTGATAAGAGGGTCTCACAATTCCACAGGGAAGGCATCAATTGAAGAAATGTGTTC

ATCTGCCGAAGAAACCATTCATACAGGGAGTGTAAACACGTACTCTTACACAGATGTGAAC

CTCAAGCCCTACATGACATATGAGTACAGGATTTCTGCCTGGAACAGCTATGGGCGAGGAC

TCAGCAAAGCTGTGAGAGCCAGAACAAAGAAGATGTGCCTCAAGGAGTGAGTCCCCCTA

CGTGGACCAAAATAGACAATCTTGAAGATACAATTGTCTTAAACTGGAGAAAACCTATACA

ATCAAATGGTCCTATTATTTACTACATCCTTCTTCGAAATGGAATTGAACGTTTTCGGGGAAC

ATCACTGAGCTTCTCTGATAAAGAGGGAATTCAACCATTTCAGGAATATTCATATCAGCTGA

AAGCTTGCACGGTTGCTGGCTGTGCCACCAGTAGCAAGGTAGTTGCAGCTACTACCCAAGG

AGTTCCGGAGAGCATCCTGCCACCAAGCATCACAGCCCTAAGTGCAGTGGCTCTGCATCTG

AGCTGGAGTGTCCCTGAGAAATCAAACGGCGTCATTAAAGAGTACCAGATCAGGCAGGTTG

GGAAAGGTCTCATCCACACTGACACCACTGACAGGAGACAGCATACGGTCACAGGTCTCCA

GCCATACACCAACTACAGCTTCACTCTTACAGCTTGTACATCTGCTGGGTGCACTTCAAGCG

AGCCTTTTCTAGGTCAGACACTGCAGGCAGCTCCTGAAGGAGTTTGGGTGACACCTCGACA

CATTATCATCAATTCTACAACAGTGGAATTATATTGGAGTCTGCCAGAAAAGCCCAATGGCC

TCGTTTCTCAATATCAATTGAGTCGTAATGGAAACTTGCTTTTCCTGGGTGGCAGTGAGGAG

CAGAATTTCACTGATAAAAACCTGGAGCCCAATAGCAGATACACTTACAAGTTAGAAGTCA

AAACTGGAGGTGGCAGCAGTGCTAGTGATGATTACATTGTTCAAACACCTATGTCAACACC

AGAAGAAATCTATCCTCCATATAATATCACAGTAATTGGGCCTTATTCTATATTTGTAGCTTG

GATACCACCAGGGATCCTCATCCCCGAAATTCCTGTGGAGTACAATGTCTTACTCAATGATG

GAAGTGTAACACCTCTGGCCTTCTCCGTTGGTCATCATCAATCCACCCTTCTGGAAAATTTGA

CTCCATTCACACAGTATGAGATAAGGATACAAGCATGTCAAAATGGAAGTTGTGGAGTTAG

CAGTAGGATGTTTGTCAAAACACCTGAAGCAGCCCCAATGGATCTTAATTCTCCTGTTCTTA

AGGCACTGGGGTCAGCTTGCATAGAGATTAAGTGGATGCCACCTGAAAAACCAAATGGAAT

CATCATCAACTACTTTATTTACAGACGCCCTGCTGGCATTGAAGAGGAGTCTGTTTTATTTGT

CTGGTCAGAAGGAGCCCTTGAATTTATGGATGAAGGAGACACCCTGAGGCCTTTCACACTC

TACGAATATCGGGTCAGAGCCTGTAACTCCAAGGGTTCAGTGGAGAGTCTGTGGTCATTAA

CACAAACTCTGGAAGCTCCACCTCAAGATTTTCCAGCTCCTTGGGCTCAAGCCACGAGTGCT

CATTCAGTTCTGTTGAATTGGACAAAGCCAGAATCTCCCAATGGCATTATCTCCCATTACCGT

GTGGTCTACCAGGAGAGACCCGACGATCCTACATTTAACAGCCCTACCGTGCATGCTTTCAC

AGTGAAGGGAACAAGCCATCAAGCCCACCTGTACGGGTTAGAACCATTCACAACATATCGC

ATTGGTGTTGTGGCTGCAAACCATGCAGGAGAAATTTTAAGCCCTTGGACTCTGATTCAAAC

CTTAGAATCTTCCCCAAGTGGACTGAGAAACTTTATAGTAGAACAGAAAGAGAATGGCCGG

GCATTGCTACTACAGTGGTCAGAACCTATGAGAACCAATGGTGTGATTAAGACATACAACA

TCTTCAGTGACGGGTTCCTGGAGTACTCTGGTTTGAATCGTCAGTTTCTCTTCCGCCGCCTGG

ATCCTTTCACTCTCTACACACTGACCCTGGAGGCCTGCACCAGAGCAGGTTGTGCACACTCG
```

-continued

```
GCGCCTCAGCCTCTGTGGACAGATGAAGCCCTCCAGACTCTCAGCTGGCTCCTACTGTCCA

CTCTGTGAAGTCCACCAGTGTTGAGCTGAGCTGGTCTGAGCCTGTTAACCCAAATGGAAAA

ATAATTCGCTATGAAGTGATTCGCAGATGCTTCGAGGGAAAAGCTTGGGGAAATCAGACGA

TCCAGGCCGACGAGAAAATTGTTTTCACAGAATATAACACTGAAAGGAATACATTTATGTAT

AATGACACAGGTTTGCAACCATGGACGCAGTGTGAATATAAAATCTACACTTGGAATTCAG

CTGGGCATACCTGTAGCTCTTGGAATGTGGTGAGGACATTGCAAGCACCTCCAGAAGGTCT

CTCTCCACCTGTGATATCCTATGTTTCTATGAATCCCCAAAAACTGCTGATTTCCTGGATCCC

ACCAGAACAGTCTAATGGTATTATCCAGTCCTATAGGCTTCAAAGGAATGAAATGCTCTATC

CTTTTAGCTTTGATCCTGTGACTTTCAATTACACTGATGAAGAGCTTCTTCCTTTTTCCACCTA

TAGCTATGCACTCCAAGCCTGCACGAGTGGAGGATGCTCCACCAGCAAACCCACCAGCATC

ACAACTCTGGAGGCTGCTCCATCAGAAGTCAGCCCTCCAGATCTTTGGGCCGTCAGTGCCAC

TCAAATGAATGTATGTTGGTCACCGCCCACAGTGCAAAATGGAAAGATTACTAAATATTTAG

TTAGATATGATAATAAAGAGTCCCTTGCTGGCCAGGGCCTGTGCCTGCTGGTTTCCCACCTG

CAGCCTTACTCTCAGTATAACTTCTCCCTTGTAGCCTGCACGAATGGAGGTTGCACAGCTAG

TGTGTCAAAATCTGCCTGGACAATGGAGGCCCTGCCAGAGAACATGGACTCTCCAACATTG

CAAGTCACAGGCTCAGAATCAATAGAAATCACCTGGAAACCTCCAAGAAACCCAAATGGCC

AGATCAGAAGTTATGAACTTAGGAGGGATGGAACCATTGTATATACAGGCTTGGAAACACG

CTATCGTGATTTTACTCTCACCCCAGGTGTGGAGTATAGCTACACAGTAACTGCCAGCAACA

GCCAAGGGGTATTTTGAGTCCTCTTGTCAAAGATCGAACCAGCCCCTCAGCACCCTCAGG

GATGGAACCTCCAAAATTGCAGGCCAGGGTCCTCAGGAGATCTTAGTGAACTGGGACCCT

CCAGTGAGAACAAATGGTGATATCATCAATTATACCCTCTTCATCCGTGAACTATTTGAAAG

AGAAACTAAAATCATACACATAAACACAACTCATAATTCTTTTGGTATGCAGTCATATATAGT

AAACCAGCTGAAGCCATTTCACAGGTATGAAATACGAATTCAAGCGTGCACCACCCTGGGA

TGTGCATCAAGTGACTGGACATTCATACAGACCCCTGAGATTGCACCTTTGATGCAACCCCC

TCCACATCTGGAGGTACAAATGGCTCCAGGAGGATTCCAGCCAACTGTTTCTCTTTTGTGGA

CAGGACCGCTGCAGCCAAATGGAAAAGTTTTGTATTACGAATTATACAGAAGACAAATAGC

AACTCAGCCTAGAAAATCCAATCCAGTCCTAATCTATAACGGAAGCTCAACATCTTTTATAG

ATTCCGAACTATTGCCTTTCACAGAGTATGAGTATCAGGTCTGGGCAGTGAATTCTGCAGGA

AAAGCCCCCAGTAGCTGGACATGGTGCAGAACCGGGCCAGCCCCACCAGAAGGTCTCAGA

GCCCCCACGTTCCATGTGATCTCTTCTACCCAAGCAGTGGTCAACATCAGTGCCCCTGGGAA

GCCCAACGGGATCGTCAGTCTCTACAGGCTGTTCTCCAGCAGCGCCCATGGGGCTGAGACA

GTGCTATCCGAAGGCATGGCCACCCAGCAGACTCTCCATGGCCTTCAAGCCTTCACTAACTA

CTCTATTGGAGTAGAGGCCTGCACCTGCTTCAACTGTTGCAGCAAAGGACCGACAGCTGAA

CTGAGAACCCATCCTGCCCCACCCTCAGGACTGTCCTCTCCACAAATCGGGACGCTGGCCTC

AAGGACGGCCTCCTTCCGGTGGAGTCCCCCCATGTTCCCCAATGGTGTCATTCACAGCTATG

AACTCCAATTCCACGTGGCTTGCCCTCCTGACTCAGCCCTCCCCTGTACTCCCAGCCAAATAG

AAACAAAGTACACGGGGCTGGGGCAGAAAGCCAGCCTTGGGGGTCTCCAGCCCTACACCA

CATACAAGCTGAGAGTGGTGGCACACAACGAGGTGGGCAGTACGGCTTCCGAGTGGATCA

GTTTCACCACCCAAAAAGAATTGCCTCAGTACCGAGCCCCATTTTCGGTGGACAGCAATTTG

TCTGTGGTGTGTGTGAACTGGAGTGACACCTTCCTCCTGAACGGCCAACTGAAGGAGTACG

TGTTAACCGACGGAGGGCGACGCGTGTACAGCGGCTTGGACACCACCCTCTACATACCGAG
```

-continued

```
AACGGCGGACAAAACCTTCTTTTTCCAGGTCATCTGCACGACTGACGAAGGAAGTGTTAAG

ACGCCGTTGATCCAATATGATACCTCTACTGGACTTGGCTTGGTCCTAACAACTCCTGGGAA

AAAGAAGGGATCGCGGAGCAAAAGCACAGAGTTCTACAGCGAGCTGTGGTTCATAGTGTT

AATGGCGATGCTGGGCTTGATCTTGTTGGCCATTTTTCTGTCCCTGATACTACAAAGAAAAA

TCCACAAAGAGCCATATATCAGAGAAAGACCTCCCTTGGTACCTCTTCAGAAGAGGATGTCT

CCATTGAATGTTTACCCACCGGGGGAAAACCATATGGGGTTAGCCGATACCAAAATTCCCC

GGTCTGGGACACCTGTGAGTATCCGCAGCAACCGGAGTGCATGTGTCCTGCGCATCCCGAG

TCAAAACCAAACCAGCCTAACCTACTCCCAGGGTTCTCTTCACCGCAGCGTCAGCCAGCTCA

TGGACATTCAAGACAAGAAAGTCTTGATGGACAACTCACTGTGGGAAGCCATCATGGGCCA

CAACAGTGGACTGTATGTGGATGAAGAGGACCTGATGAACGCCATCAAGGATTTCAGCTCA

GTGACTAAGGAACGCACCACATTCACAGACACCCACCTGTAAAGGATGGAAACCCAGAAGA

CGTAACCCTGGAATGCAAGGTCTGCACCCATTTCCTCCTGGGTTATCACTCACACATCATAAA

TGCTGAAAAGCCATTGTTTATTATCCTATAATTCTTTAAAGAAATGATGACTGTTTTTGAAAG

TGTTCCTTCCTAATAGAGGTCTAAGAAATGATATTTTTCTCATCTTAAATGAGAGAGAATATT

CATATGAAAATACTTGATTTGCTCTTATTTTGTAGAAGACAAAGAAGTATGTAATTGTCACTT

GGTTCTGTTTGGCAGTGATGCTCCTGGTTAACTGAATAATCAGTGGCAATTTCAAGATGGCT

CACAGTTGTTAGAAGTAGTAAGTTAGTTACTGGCTCAAAAATGATTCTGTTGAAAGGATGTC

ACTGCTGTTCATTTCTATCTGCCATTTCTGTCAGGGTTGACACAATCCTGCAAGAATAGTTAT

TCTAATGATCACAGCTGCTAAATGAATCCCAAACTTTGCACCAGGTCGACAAACTTTTCTGA

AGGTTCTATTTATTTACCATACATAGGGTTACTTACCAAACTTTTTGACAAGGCTGAAGGTTC

TATTTATTTACAATACATAGGGTTACTCACCAAACTTTTTGACAAGGCAACACATAACTTACA

CATAAATGTCTCTGTTCTTGCATTTATGAATTTTCCAAAAATCTAAGGAGTAAACAGCTTATT

TATACATTTTGAGGAGAAAACAAAGTGTTTCACTAGGAACACCTCTACTTGAACCAATGTTT

TTATTTCATATATTTTATAGTTTTGAAACTAGTTTCTCATAAAATTCTGTCAATTCACTGAATA

TCAGAGAATACTGACATCTTCAACCTAGCACATTTCAAATGGAAACTACTGTTCTATTTGCAA

TATTAGGCTGCGTGAAATTTTAAAAGGAAAAATGTATCTGTTCCTTCTAGCATTAACATATAT

ACATGTAGAGACAAGACTATACCTATGTGTATATATATGTATATCATGTATATATTACTCTGC

ACTATATCCCTTCTTTTTGGAGAACTAGCCATTATTTTAGCCACAGAATCAGTAAGAACAGAT

GATATGCAACAGTACCAATTACGGTTCAAAAATGTCTGTCACCTGCTCTAGTTGGATTACAA

AGTCATTGGTGAAAGTCCTATGGCAAGAAAAATTTTCTTGCAAATCATCCACATAAAATCAG

ATATTTAAATTTGTTCTTCATGGAAAACAGAGTAAGAAAACCTCTTGTCTTCCTTCATCCTTA

AAGGTCTTTGTGACCCCAGGAAAATATTGACTCTGTCTAACACACAATAGTCACAATACTTTT

TGTGAATCTACAACCAGAGACAGGCAAAAACTTGTAAAGTAAGGGATAGTCTTACTTATTCT

GCCTGAAAACAATGTATTACCCCAGGGCCCAACAGTAAAAGATTGTGGACTTTTTGGGTATT

GAGATTTCATCTAGCTCTGTGAGAGAGCAGCTCCTCAGACTGACCAACTCCTAGACAAAGTT

TGCCAACCATAAGTGTCAAAAGCACAGGCCAGTATTAAGCAGAAGTTCTACCACCTTATTAG

AACTGCTATAAACAAAAGCATCTGAAATAATTGTGCACATCTGGCAGTGACTGTAGAAAAT

ACGAAATATATATTTCTCGCCAAGTTTTTATACTTTCTGAAATGAAAACATAGGATTGACTAG

TTTACTGGTTTTTATTCCCATATGCCGATTCTGGGACAATAAAGTTGTTTAAAGCTGGCACAA

ATAAGCATTAACCAAGGCTGTGTCCACCTTCTGTGAGCTACTTAAGGTATATAGGAAAGGA
```

-continued
```
GTGGTCACAAACTTGCATCCTAATCCTTGGTGGACTCTTCTAAGAATACAGTTTGCTAGTCAC

AAAGAATAGTCTACAAATATGCTTTGCTAGGTTCAGAAGATTGAGTTTATCCTGATTTTTGA

AAAATTAACCAGGTATCTTTATCACTGTGTATTTTTCCAAGCACAGTATAAAATTTTAACAAC

GCACAAAAAAATACAGAACTGCAGGGGATTTTATCTTGGATCATTATCCATTTAATCATCTA

ATTAGACATGAACTCAGTTAGCTGAATCATTTACATTTTGACTCCATAGCTTAGGGCAGACA

GAAGCCTGTATGGCTTCTGCCCAGAACTCTGTCCCCTGCTACATGTCTAAGTTTACTTGTATT

TATTTCAGAGAAGAACTCTAAGATGTTGCTTTGCTACTTTAAGTGGTATTGCGTGCCAAGCC

TCTATTATACAAACCATGCAGACTCGCCTCTAGAGATTCTGATTCGGTTGATCTGGGGTGTG

TGGCTGAGGCATCAGTACTTTTTAAAGCTTCCAGGTGTTCTAATGTTGAGACCCACTGATGT

TCCACAATCTGGAAGAAATCATGTACAGGAATAATATGCTATGCACAGGGACTATGCTCCTT

GGCTCACCCCTTCTCCCTTATAAACAATGAGCAGTTCTTGATGAACCTCTTTAAATTTAAATC

TCCTGACTCACATTTTACCAATTGTACATGCCACATTCTCAGCTTACGAACTACCATGTTTTGT

TATTCTTAATATCAACTGTTTGGTAAGAGTACAGTTGTTTTTATACACTCTAAGAAATGTGTT

TATAATCTACTGTAATTTCCACTAAATGGAACCCAAATATTAATGTTATGGTACCATATACTG

ATGTAAAAATCATGCTGGCATCCATGAACACACCGGTAAATAAAACATAGTCCAAGTGGAA

GAATTCATTAATAAGGAACTTTTAATTATGTCACAAATGAATAGTTGGTTTCCAATGCACAA

ATATCATGTAAACTAATCTAAAGATGGTTTGCTTAATAAATATTTGAATGTGACC
```

Translation of this mRNA is expected to result in expression of human Usherin protein lacking part of laminin EGF-like domain 4, all of domains 5, 6 and 7 and part of domain 8: (Partial domain 4 in bold, partial domain 8 double underlined)

(SEQ ID NO: 2)
```
MNCPVLSLGSGFLFQVIEMLIFAYFASISLTESRGLFPRLENVGAFKKVSIVPTQAVCGLPDRSTFC

HSSAAAESIQFCTQRFCIQDCPYRSSHPTYTALFSAGLSSCITPDKNDLHPNAHSNSASFIFGNHK

SCFSSPPSPKLMASFTLAVWLKPEQQGVMCVIEKTVDGQIVFKLTISEKETMFYYRTVNGLQPPI

KVMTLGRILVKKWIHLSVQVHQTKISFFINGVEKDHTPFNARTLSGSITDFASGTVQIGQSLNGLE

QFVGRMQDFRLYQVALTNREILEVFSGDLLRLHAQSHCRCPGSHPRVHPLAQRYCIPNDAGDT

ADNRVSRLNPEAHPLSFVNDNDVGTSWVSNVFTNITQLNQGVTISVDLENGQYQVFYIIIQFFS

PQPTEIRIQRKKENSLDWEDWQYFARNCGAFGMKNNGDLEKPDSVNCLQLSNFTPYSRGNVT

FSILTPGPNYRPGYNNFYNTPSLQEFVKATQIRFHFHGQYYTTETAVNLRHRYYAVDEITISGRCQ

CHGHADNCDTTSQPYRCLCSQESFTEGLHCDRCLPLYNDKPFRQGDQVYAFNCKPCQCNSHSK

SCHYNISVDPFPFEHFRGGGGVCDDCEHNTTGRNCELCKDYFFRQVGADPSAIDVCKPCDCDT

VGTRNGSILCDQIGGQCNCKRHVSGRQCNQCQNGFYNLQELDPDGCSPCNCNTSGTVDGDIT

CHQNSGQCKCKANVI<u>GFYISPGNATGCLP</u>CSCHTTGAVNHICNSLTGQCVCQDASIAGQRCDQ

CKDHYFGFDPQTGRCQPCNCHLSGALNETCHLVTGQCFCKQFVTGSKCDACVPSASHLDVNNL

LGCSKTPFQQPPPRGQVQSSSAINLSWSPPDSPNAHWLTYSLLRDGFEIYTTEDQYPYSIQYFLD

TDLLPYTKYSYYIETTNVHGSTRSVAVTYKTKPGVPEGNLTLSYIIPIGSDSVTLTWTTLSNQSGPIE

KYILSCAPLAGGQPCVSYEGHETSATIWNLVPFAKYDFSVQACTSGGCLHSLPITVTTAQAPPQR

LSPPKMQKISSTELHVEWSPPAELNGIIRYELYMRRLRSTKETTSEESRVFQSSGWLSPHSFVESA

NENALKPPQTMTTITGLEPYTKYEFRVLAVNMAGSVSSAWVSERTGESAPVFMIPPSVFPLSSYS
```

-continued

LNISWEKPADNVTRGKVVGYDINMLSEQSPQQSIPMAFSQLLHTAKSQELSYTVEGLKPYRIYEF

TITLCNSVGCVTSASGAGQTLAAAPAQLRPPLVKGINSTTIHLKWFPPEELNGPSPIYQLERRESSL

PALMTTMMKGIRFIGNYCKFPSSTHPVNTDFTGIKASFRTKVPEGLIVFAASPGNQEEYFALQL

KKGRLYFLFDPQGSPVEVTTTNDHGKQYSDGKWHEIIAIRHQAFGQITLDGIYTGSSAILNGSTVI

GDNTGVFLGGLPRSYTILRKDPEIIQKGFVGCLKDVHFMKNYNPSAIWEPLDWQSSEEQINVYN

SWEGCPASLNEGAQFLGAGFLELHPYMFHGGMNFEISFKFRTDQLNGLLLFVYNKDGPDFLAM

ELKSGILTFRLNTSLAFTQVDLLLGLSYCNGKWNKVIIKKEGSFISASVNGLMKHASESGDQPLVV

NSPVYVGGIPQELLNSYQHLCLEQGFGGCMKDVKFTRGAVVNLASVSSGAVRVNLDGCLSTDS

AVNCRGNDSILVYQGKEQSVYEGGLQPFTEYLYRVIASHEGGSVYSDWSRGRTTGAAPQSVPTP

SRVRSLNGYSIEVTWDEPVVRGVIEKYILKAYSEDSTRPPRMPSASAEFVNTSNLTGILTGLLPFKN

YAVTLTACTLAGCTESSHALNISTPQEAPQEVQPPVAKSLPSSLLLSWNPPKKANGIITQYCLYMD

GRLIYSGSEENYTVTDLAVFTPHQFLLSACTHVGCTNSSWVLLYTAQLPPEHVDSPVLTVLDSRTI

HIQWKQPRKISGILERYVLYMSNHTHDFTIWSVIYNSTELFQDHMLQYVLPGNKYLIKLGACTGG

GCTVSEASEALTDEDIPEGVPAPKAHSYSPDSFNVSWTEPEYPNGVITSYGLYLDGILIHNSSELSY

RAYGFAPWSLHSFRVQACTAKGCALGPLVENRTLEAPPEGTVNVFVKTQGSRKAHVRWEAPFR

PNGLLTHSVLFTGIFYVDPVGNNYTLLNVTKVMYSGEETNLWVLIDGLVPFTNYTVQVNISNSQ

GSLITDPITIAMPPGAPDGVLPPRLSSATPTSLQVVWSTPARNNAPGSPRYQLQMRSGDSTHGF

LELFSNPSASLSYEVSDLQPYTEYMFRLVASNGFGSAHSSWIPFMTAEDKPGPVVPPILLDVKSR

MMLVTWQHPRKSNGVITHYNIYLHGRLYLRTPGNVTNCTVMHLHPYTAYKFQVEACTSKGCSL

SPESQTVWTLPGAPEGIPSPELFSDTPTSVIISWQPPTHPNGLVENFTIERRVKGKEEVTTLVTLPR

SHSMRFIDKTSALSPWTKYEYRVLMSTLHGGTNSSAWVEVTTRPSRPAGVQPPVVTVLEPDAV

QVTWKPPLIQNGDILSYEIHMPDPHITLTNVTSAVLSQKVTHLIPFTNYSVTIVACSGGNGYLGG

CTESLPTYVTTHPTVPQNVGPLSVIPLSESYVVISWQPPSKPNGPNLRYELLRRKIQQPLASNPPE

DLNRWHNIYSGTQWLYEDKGLSRFTTYEYMLFVHNSVGFTPSREVIVTTLAGLPERGANLTASV

LNHTAIDVRWAKPTVQDLQGEVEYYTLFWSSATSNDSLKILPDVNSHVIGHLKPNTEYWIFISVF

NGVHSINSAGLHATTCDGEPQGMLPPEVVIINSTAVRVIWTSPSNPNGVVTEYSIYVNNKLYKT

GMNVPGSFILRDLSPFTIYDIQVEVCTIYACVKSNGTQITTVEDTPSDIPTPTIRGITSRSLQIDWVS

PRKPNGIILGYDLLWKTWYPCAKTQKLVQDQSDELCKAVRCQKPESICGHICYSSEAKVCCNGVL

YNPKPGHRCCEEKYIPFVLNSTGVCCGGRIQEAQPNHQCCSGYYARILPGEVCCPDEQHNRVSV

GIGDSCCGRMPYSTSGNQICCAGRLHDGHGQKCCGRQIVSNDLECCGGEEGVVYNRLPGMFC

CGQDYVNMSDTICCSASSGESKAHIKKNDPVPVKCCETELIPKSQKCCNGVGYNPLKYVCSDKIS

TGMMMKETKECRILCPASMEATEHCGRCDFNFTSHICTVIRGSHNSTGKASIEEMCSSAEETIHT

GSVNTYSYTDVNLKPYMTYEYRISAWNSYGRGLSKAVRARTKEDVPQGVSPPTWTKIDNLEDTI

VLNWRKPIQSNGPIIYYILLRNGIERFRGTSLSFSDKEGIQPFQEYSYQLKACTVAGCATSSKVVAA

TTQGVPESILPPSITALSAVALHLSWSVPEKSNGVIKEYQIRQVGKGLIHTDTTDRRQHTVTGLQP

YTNYSFTLTACTSAGCTSSEPFLGQTLQAAPEGVWVTPRHIIINSTTVELYWSLPEKPNGLVSQYQ

LSRNGNLLFLGGSEEQNFTDKNLEPNSRYTYKLEVKTGGGSSASDDYIVQTPMSTPEEIYPPYNIT

VIGPYSIFVAWIPPGILIPEIPVEYNVLLNDGSVTPLAFSVGHHQSTLLENLTPFTQYEIRIQACQNG

SCGVSSRMFVKTPEAAPMDLNSPVLKALGSACIEIKWMPPEKPNGIIINYFIYRRPAGIEEESVLF

VWSEGALEFMDEGDTLRPFTLYEYRVRACNSKGSVESLWSLTQTLEAPPQDFPAPWAQATSAH

SVLLNWTKPESPNGIISHYRVVYQERPDDPTFNSPTVHAFTVKGTSHQAHLYGLEPFTTYRIGVV

-continued

```
AANHAGEILSPWTLIQTLESSPSGLRNFIVEQKENGRALLLQWSEPMRTNGVIKTYNIFSDGFLEY

SGLNRQFLFRRLDPFTLYTLTLEACTRAGCAHSAPQPLWIDEAPPDSQLAPTVHSVKSTSVELSW

SEPVNPNGKIIRYEVIRRCFEGKAWGNQTIQADEKIVFTEYNTERNTFMYNDTGLQPWTQCEYK

IYTWNSAGHTCSSWNVVRTLQAPPEGLSPPVISYVSMNPQKLLISWIPPEQSNGIIQSYRLQRNE

MLYPFSFDPVTFNYTDEELLPFSTYSYALQACTSGGCSTSKPTSITTLEAAPSEVSPPDLWAVSAT

QMNVCWSPPTVQNGKITKYLVRYDNKESLAGQGLCLLVSHLQPYSQYNFSLVACINGGCTASV

SKSAWTMEALPENMDSPTLQVTGSESIEITWKPPRNPNGQIRSYELRRDGTIVYTGLETRYRDFT

LTPGVEYSYTVTASNSQGGILSPLVKDRTSPSAPSGMEPPKLQARGPQEILVNWDPPVRINGDII

NYTLFIRELFERETKIIHINTTHNSFGMQSYIVNQLKPFHRYEIRIQACTTLGCASSDWTFIQTPEIA

PLMQPPPHLEVQMAPGGFQPTVSLLWTGPLQPNGKVLYYELYRRQIATQPRKSNPVLIYNGSS

TSFIDSELLPFTEYEYQVWAVNSAGKAPSSWTWCRTGPAPPEGLRAPTFHVISSTQAVVNISAP

GKPNGIVSLYRLFSSSAHGAETVLSEGMATQQTLHGLQAFTNYSIGVEACTCFNCCSKGPTAELR

THPAPPSGLSSPQIGTLASRTASFRWSPPMFPNGVIHSYELQFHVACPPDSALPCTPSQIETKYT

GLGQKASLGGLQPYTTYKLRVVAHNEVGSTASEWISFTTQKELPQYRAPFSVDSNLSVVCVNWS

DTFLLNGQLKEYVLTDGGRRVYSGLDTTLYIPRTADKTFFFQVICTTDEGSVKTPLIQYDTSTGLGL

VLTTPGKKKGSRSKSTEFYSELWFIVLMAMLGLILLAIFLSLILQRKIHKEPYIRERPPLVPLQKRMS

PLNVYPPGENHMGLADTKIPRSGTPVSIRSNRSACVLRIPSQNQTSLTYSQGSLHRSVSQLMDIQ

DKKVLMDNSLWEAIMGHNSGLYVDEEDLMNAIKDFSSVTKERTTFTDTHL
```

REFERENCES

1. Hartong, D. T., E. L. Berson, and T. P. Dryja, Retinitis pigmentosa. Lancet, 2006. 368 (9549): p. 1795-809.
2. Saihan, Z., et al., Update on Usher syndrome. Curr Opin Neurol, 2009. 22 (1): p. 19-27.
3. Lentz, J. and B. Keats, Usher Syndrome Type II, in GeneReviews®, R. A. Pagon, et al., Editors. 1993, University of Washington, Seattle: Seattle WA.
4. Sandberg, M. A., et al., Disease course in patients with autosomal recessive retinitis pigmentosa due to the USH2A gene. Invest Ophthalmol Vis Sci, 2008. 49 (12): p. 5532-9.
5. Maguire, A. M., et al., Safety and efficacy of gene transfer for Leber's congenital amaurosis. The New England journal of medicine, 2008. 358 (21): p. 2240-8.
6. Bainbridge, J. W., et al., Effect of gene therapy on visual function in Leber's congenital amaurosis. N. Engl. J. Med., 2008. 358 (21): p. 2231-2239.
7. Cideciyan, A. V., et al., Human gene therapy for RPE65 isomerase deficiency activates the retinoid cycle of vision but with slow rod kinetics. Proc. Nat. Acad. Sci., 2008. 105 (39): p. 15112-7.
8. Maguire, A. M., et al., Age-dependent effects of RPE65 gene therapy for Leber's congenital amaurosis: a phase 1 dose-escalation trial. Lancet, 2009. 374 (9701): p. 1597-605.
9. Jacobson, S. G., et al., Gene therapy for leber congenital amaurosis caused by RPE65 mutations: safety and efficacy in 15 children and adults followed up to 3 years. Archives of Ophthalmology, 2012. 130 (1): p. 9-24.
10. Bennett, J., et al., AAV2 gene therapy readministration in three adults with congenital blindness. Science translational medicine, 2012. 4 (120): p. 120ra15.
11. Bowles, D. E., et al., Phase 1 gene therapy for Duchenne muscular dystrophy using a translational optimized AAV vector. Molecular therapy: the journal of the American Society of Gene Therapy, 2012. 20 (2): p. 443-55.
12. Maclachlan, T. K., et al., Preclinical safety evaluation of AAV2-sFLT01-a gene therapy for age-related macular degeneration. Molecular therapy: the journal of the American Society of Gene Therapy, 2011. 19 (2): p. 326-34.
13. Nathwani, A. C., et al., Adenovirus-associated virus vector-mediated gene transfer in hemophilia B. The New England journal of medicine, 2011. 365 (25): p. 2357-65.
14. Ran, F. A., et al., In vivo genome editing using *Staphylococcus aureus* Cas9. Nature, 2015. 520 (7546): p. 186-91.
15. Swiech, L., et al., In vivo interrogation of gene function in the mammalian brain using CRISPR-Cas9. Nat Biotechnol, 2015. 33 (1): p. 102-6.
16. van Wijk, E., et al., Identification of 51 novel exons of the Usher syndrome type 2A (USH2A) gene that encode multiple conserved functional domains and that are mutated in patients with Usher syndrome type II. Am J Hum Genet, 2004. 74 (4): p. 738-44.
17. Grati, M., et al., Localization of PDZD7 to the stereocilia ankle-link associates this scaffolding protein with the Usher syndrome protein network. J Neurosci, 2012. 32 (41): p. 14288-93.
18. Liu, X., et al., Usherin is required for maintenance of retinal photoreceptors and normal development of cochlear hair cells. Proc Natl Acad Sci U SA, 2007. 104 (11): p. 4413-8.
19. Aller, E., et al., The USH2A c.2299delG mutation: dating its common origin in a Southern European population. Eur J Hum Genet, 2010. 18 (7): p. 788-93.

20. Yan, D., et al., Mutation analysis in the long isoform of USH2A in American patients with Usher Syndrome type II. J Hum Genet, 2009. 54 (12): p. 732-8.
21. Kemaladewi, D. U. and R. D. Cohn, Exon Snipping in Duchenne Muscular Dystrophy. Trends Mol Med, 2016. 22 (3): p. 187-9.
22. Long, C., et al., Postnatal genome editing partially restores dystrophin expression in a mouse model of muscular dystrophy. Science, 2016. 351 (6271): p. 400-3.
23. Nelson, C. E., et al., In vivo genome editing improves muscle function in a mouse model of Duchenne muscular dystrophy. Science, 2016. 351 (6271): p. 403-7.
24. Tabebordbar, M., et al., In vivo gene editing in dystrophic mouse muscle and muscle stem cells. Science, 2016. 351 (6271): p. 407-11.
25. Young, C. S., et al., A Single CRISPR-Cas9 Deletion Strategy that Targets the Majority of DMD Patients Restores Dystrophin Function in hiPSC-Derived Muscle Cells. Cell Stem Cell, 2016. 18 (4): p. 533-40.
26. Kalinec, F., et al., Establishment and characterization of conditionally immortalized organ of corti cell lines. Cell Biol Int, 1999. 23 (3): p. 175-84.
27. Millan, J. M., et al., An update on the genetics of usher syndrome. J Ophthalmol, 2011. 2011: p. 417217.
28. Lenassi, E., et al., A detailed clinical and molecular survey of subjects with nonsyndromic USH2A retinopathy reveals an allelic hierarchy of disease-causing variants. Eur J Hum Genet, 2015. 23 (10): p. 1318-27.
29. Suzuki, K., et al., In vivo genome editing via CRISPR/Cas9 mediated homology-independent targeted integration. Nature, 2016. 540 (7631): p. 144-149.
30. Zou, J., et al., Whirlin replacement restores the formation of the USH2 protein complex in whirlin knockout photoreceptors. Invest Ophthalmol Vis Sci, 2011. 52 (5): p. 2343-51.
31. Zou, J., et al., Deletion of PDZD7 disrupts the Usher syndrome type 2 protein complex in cochlear hair cells and causes hearing loss in mice. Hum Mol Genet, 2014. 23 (9): p. 2374-90.
32. Davis, E. E., et al., TTC21B contributes both causal and modifying alleles across the ciliopathy spectrum. Nat Genet, 2011. 43 (3): p. 189-96.
33. Zhang, Q., et al., Knockdown of ttc26 disrupts ciliogenesis of the photoreceptor cells and the pronephros in zebrafish. Mol Biol Cell, 2012. 23 (16): p. 3069-78.
34. Wang, H., et al., One-step generation of mice carrying mutations in multiple genes by CRISPR/Cas-mediated genome engineering. Cell, 2013. 153 (4): p. 910-8.
35. Inui, M., et al., Rapid generation of mouse models with defined point mutations by the CRISPR/Cas9 system. Sci Rep, 2014. 4: p. 5396.
36. Mashiko, D., et al., Feasibility for a large scale mouse mutagenesis by injecting CRISPR/Cas plasmid into zygotes. Dev Growth Differ, 2014. 56 (1): p. 122-9.
37. Lu, B., et al., Cell transplantation to arrest early changes in an ush2a animal model. Invest Ophthalmol Vis Sci, 2010. 51 (4): p. 2269-76.
38. Liu, Q., J. Zuo, and E. A. Pierce, The retinitis pigmentosa 1 protein is a photoreceptor microtubule-associated protein. J Neurosci, 2004. 24 (29): p. 6427-36.
39. Cheng, A. W., et al., Multiplexed activation of endogenous genes by CRISPR-on, an RNA-guided transcriptional activator system. Cell Res, 2013. 23 (10): p. 1163-71.
40. Ousterout, D. G., et al., Multiplex CRISPR/Cas9-based genome editing for correction of dystrophin mutations that cause Duchenne muscular dystrophy. Nat Commun, 2015. 6: p. 6244.
41. Platt, R. J., et al., CRISPR-Cas9 knockin mice for genome editing and cancer modeling. Cell, 2014. 159 (2): p. 440-55.
42. Senis, E., et al., CRISPR/Cas9-mediated genome engineering: an adeno-associated viral (AAV) vector toolbox. Biotechnol J, 2014. 9 (11): p. 1402-12.
43. Tsai, S. Q., et al., GUIDE-seq enables genome-wide profiling of off-target cleavage by CRISPR-Cas nucleases. Nat Biotechnol, 2015. 33 (2): p. 187-97.
44. Tsai, S. Q., et al., Open-source guideseq software for analysis of GUIDE-seq data. Nat Biotechnol, 2016. 34 (5): p. 483.
45. Matsuda, T. and C. L. Cepko, Controlled expression of transgenes introduced by in vivo electroporation. Proc Natl Acad Sci USA, 2007. 104 (3): p. 1027-32.
46. Jelcick, A. S., et al., Genetic variations strongly influence phenotypic outcome in the mouse retina. PLOS One, 2011. 6 (7): p. e21858.
47. Liu, Q., A. Saveliev, and E. A. Pierce, The severity of retinal degeneration in Rplh gene-targeted mice is dependent on genetic background. Invest Ophthalmol Vis Sci, 2009. 50 (4): p. 1566-74.
48. Vijayakumar S, Depreux F F, Jodelka F M, et al. Rescue of peripheral vestibular function in Usher syndrome mice using a splice-switching antisense oligonucleotide. Hum Mol Genet. 2017 Sep. 15; 26 (18): 3482-3494.
49. Slijkerman RW, Vaché C, Dona M, et al. Antisense Oligonucleotide-based Splice Correction for USH2A-associated Retinal Degeneration Caused by a Frequent Deep-intronic Mutation. Mol Ther Nucleic Acids. 2016 Nov. 1; 5 (10): e381.
50. Annemieke Aartsma-Rus, et al. Theoretic applicability of antisense-mediated exon skipping for Duchenne muscular dystrophy. Hum Mutat. 2009 March; 30 (3): 293-9.
51. Béroud C, et al. Multiexon skipping leading to an artificial DMD protein lacking amino acids from exons 45 through 55 could rescue up to 63% of patients with Duchenne muscular dystrophy. Hum Mutat. 2007 February; 28 (2): 196-202.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid comprising:
   a sequence encoding a Cas9 protein, and sequences encoding:
      a first gRNA, and a second gRNA, wherein the first and second gRNAs comprise SEQ ID NO: 54 and SEQ ID NO: 125; SEQ ID NO: 54 and SEQ ID NO: 129; SEQ ID NO: 54 and SEQ ID NO: 130; SEQ ID NO: 54 and SEQ ID NO: 134; SEQ ID NO: 54 and SEQ ID NO: 135; SEQ ID NO: 68 and SEQ ID NO: 125; SEQ ID NO: 68 and SEQ ID NO: 129; SEQ ID NO: 68 and SEQ ID NO: 130; SEQ ID NO: 68 and SEQ ID NO: 134; or SEQ ID NO: 68 and SEQ ID NO: 135, respectively.

2. The nucleic acid of claim 1, wherein the nucleic acid encodes S. aureus Cas9.

3. The nucleic acid of claim 2, wherein the Cas9 comprises a nuclear localization signal, optionally a C-terminal nuclear localization signal and/or an N-terminal nuclear localization signal; and/or wherein the sequence encoding the Cas9 comprises a polyadenylation signal.

4. The nucleic acid of claim 1, wherein the gRNA is a unimolecular S. aureus gRNA, or a two-part modular S. aureus gRNA.

5. The nucleic acid of claim 1, wherein the nucleic acid further comprises a viral delivery vector.

6. The nucleic acid of claim 5, wherein the viral delivery vector comprises a promoter for Cas9.

7. The nucleic acid of claim 5, wherein the viral delivery vector comprises an adeno-associated virus (AAV) vector.

8. The nucleic acid of claim 5, which further comprises:
   (i) a first and a second inverted terminal repeat sequence (ITR); and
   (ii) a promoter for driving expression of the Cas9, wherein the promoter is selected from the group consisting of a CMV, an EFS, or an hGRK1 promoter.

9. A method of treating a subject who has Usher Syndrome type 2 or autosomal recessive retinitis pigmentosa (arRP) caused by a mutation in exon 13 of an USH2A gene, the method comprising administering a therapeutically effective amount of the nucleic acid of claim 7 to an affected cell in the subject.

10. The method of claim 9, wherein the nucleic acid is delivered to a retina of a subject by injection or is delivered to the inner ear of a subject by injection.

11. A method of altering the genome of a cell, the method comprising contacting the cell with a CRISPR-Cas9 nuclease and gRNAs to form a first double strand break within intron 12 of the human USH2A gene and a second double strand break within intron 13 of the human USH2A gene, wherein the first double strand break is formed between nucleotides 216,248,383 and 216,248,639 of human chromosome 1 and the second double strand break is formed between nucleotides 216,245,292 and 216,246,542 of human chromosome 1, wherein the first and second double strand breaks are then repaired by the cell, thereby removing exon 13 of the USH2A gene on human chromosome 1, and wherein the step of forming the first strand break comprises contacting the cell with a first gRNA and the step of forming the second strand break comprises contacting the cell with a second gRNA, and wherein the first gRNA and the second gRNA comprise SEQ ID NO: 54 and SEQ ID NO: 125; SEQ ID NO: 54 and SEQ ID NO: 129; SEQ ID NO: 54 and SEQ ID NO: 130; SEQ ID NO: 54 and SEQ ID NO: 134; SEQ ID NO: 54 and SEQ ID NO: 135; SEQ ID NO: 68 and SEQ ID NO: 125; SEQ ID NO: 68 and SEQ ID NO: 129; SEQ ID NO: 68 and SEQ ID NO: 130; SEQ ID NO: 68 and SEQ ID NO: 134; or SEQ ID NO: 68 and SEQ ID NO: 135, respectively.

12. The method of claim 11, wherein the cell is a cell of the eye or inner ear of a mammal.

13. The method of claim 11, wherein the cell is from a subject suffering from Usher syndrome type 2A.

14. The method of claim 11, wherein the cell is a retinal cell or a photoreceptor cell.

15. The method of claim 14, wherein the photoreceptor cell is a cone photoreceptor cell or a cone cell, a rod photoreceptor cell or a rod cell or a macular cone photoreceptor cell.

16. The method of claim 11, comprising contacting the cell with a recombinant viral particle comprising:
   a nucleotide sequence encoding the first gRNA molecule;
   a nucleotide sequence encoding the second gRNA molecule; and
   a nucleotide sequence encoding a Cas9 molecule;
   wherein said viral particle is capable of delivery to a non-dividing cell, and wherein said contacting results in removal of exon 13 of human USH2A gene.

17. The method of claim 16, wherein the viral particle is an adeno-associated virus (AAV) viral particle.

* * * * *